(12) United States Patent
Mun et al.

(10) Patent No.: US 11,882,763 B2
(45) Date of Patent: Jan. 23, 2024

(54) COMPOUND FOR ORGANIC ELECTRONIC ELEMENT, ORGANIC ELECTRONIC ELEMENT USING SAME AND ELECTRONIC DEVICE THEREFOR

(71) Applicant: DUK SAN NEOLUX CO., LTD., Cheonan-si (KR)

(72) Inventors: Soung Yun Mun, Cheonan-si (KR); Jae Wan Jang, Cheonan-si (KR); Yun Suk Lee, Seongnam-si (KR); Jong Gwang Park, Cheonan-si (KR); Yeon Hee Choi, Cheonan-si (KR); Chi Hyun Park, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 556 days.

(21) Appl. No.: 16/304,379

(22) PCT Filed: May 24, 2017

(86) PCT No.: PCT/KR2017/005414
§ 371 (c)(1),
(2) Date: Nov. 26, 2018

(87) PCT Pub. No.: WO2017/204557
PCT Pub. Date: Nov. 30, 2017

(65) Prior Publication Data
US 2019/0296244 A1 Sep. 26, 2019

(30) Foreign Application Priority Data

May 26, 2016 (KR) .................. 10-2016-0065005
Jul. 4, 2016 (KR) .................. 10-2016-0084282
May 23, 2017 (KR) .................. 10-2017-0063537

(51) Int. Cl.
*H10K 85/60* (2023.01)
*C07D 307/91* (2006.01)
(Continued)

(52) U.S. Cl.
CPC .......... *H10K 85/636* (2023.02); *C07C 211/54* (2013.01); *C07D 209/82* (2013.01);
(Continued)

(58) Field of Classification Search
CPC ............. H01L 51/0061; H01L 51/0073; H01L 51/0074; H10K 85/636; H10K 85/6574; H10K 85/6576
See application file for complete search history.

(56) References Cited

U.S. PATENT DOCUMENTS

2014/0353646 A1 12/2014 Mizuki et al.
2015/0155524 A1* 6/2015 Liu ..................... H01L 51/0096
257/40
(Continued)

FOREIGN PATENT DOCUMENTS

JP      2001043979 A * 2/2001
KR    10-2004-0086249 A    10/2004
(Continued)

OTHER PUBLICATIONS

The Japanese Office Action dated Jan. 7, 2020 by the Japanese Patent Office (JPO) for Japanese Application No. 2019-513727; 6 pages.

*Primary Examiner* — Sean M DeGuire
(74) *Attorney, Agent, or Firm* — Vorys, Sater, Seymour and Pease LLP; Mih Suhn Koh

(57) ABSTRACT

Provided are an organic electronic element and an electronic device therefor, the organic electronic element having a mixture of a compound according to the present invention used as a material therefor, thereby enabling the achieve-
(Continued)

ment of high light-emitting efficiency and low driving voltage of the organic electronic element, and enabling the life of the element to be greatly extended.

6 Claims, 4 Drawing Sheets

(51) Int. Cl.
| | |
|---|---|
| C07D 333/76 | (2006.01) |
| C07D 409/12 | (2006.01) |
| C07D 209/82 | (2006.01) |
| C07C 211/54 | (2006.01) |
| C09K 11/06 | (2006.01) |
| H10K 50/00 | (2023.01) |
| H10K 50/11 | (2023.01) |
| H10K 99/00 | (2023.01) |
| H10K 50/15 | (2023.01) |
| H10K 50/17 | (2023.01) |
| H10K 101/10 | (2023.01) |

(52) U.S. Cl.
CPC ......... *C07D 307/91* (2013.01); *C07D 333/76* (2013.01); *C07D 409/12* (2013.01); *C09K 11/06* (2013.01); *H10K 50/00* (2023.02); *H10K 50/11* (2023.02); *H10K 85/622* (2023.02); *H10K 85/626* (2023.02); *H10K 85/633* (2023.02); *H10K 85/654* (2023.02); *H10K 85/6572* (2023.02); *H10K 99/00* (2023.02); *H10K 50/15* (2023.02); *H10K 50/17* (2023.02); *H10K 85/6574* (2023.02); *H10K 85/6576* (2023.02); *H10K 2101/10* (2023.02)

(56) References Cited

U.S. PATENT DOCUMENTS

| | | | |
|---|---|---|---|
| 2016/0268516 A1* | 9/2016 | Tanaka | ................. C07D 498/04 |
| 2016/0351816 A1* | 12/2016 | Kim | ....................... C09K 11/06 |
| 2016/0351817 A1 | 12/2016 | Kim et al. | |
| 2016/0351818 A1 | 12/2016 | Kim et al. | |

FOREIGN PATENT DOCUMENTS

| | | |
|---|---|---|
| KR | 10-2013-0125575 A | 11/2013 |
| KR | 10-1614739 B1 | 4/2016 |
| KR | 10-2016-0053561 A | 5/2016 |
| KR | 10-2016-0141359 A | 12/2016 |
| KR | 10-2016-0141360 A | 12/2016 |

* cited by examiner

[Fig. 1]
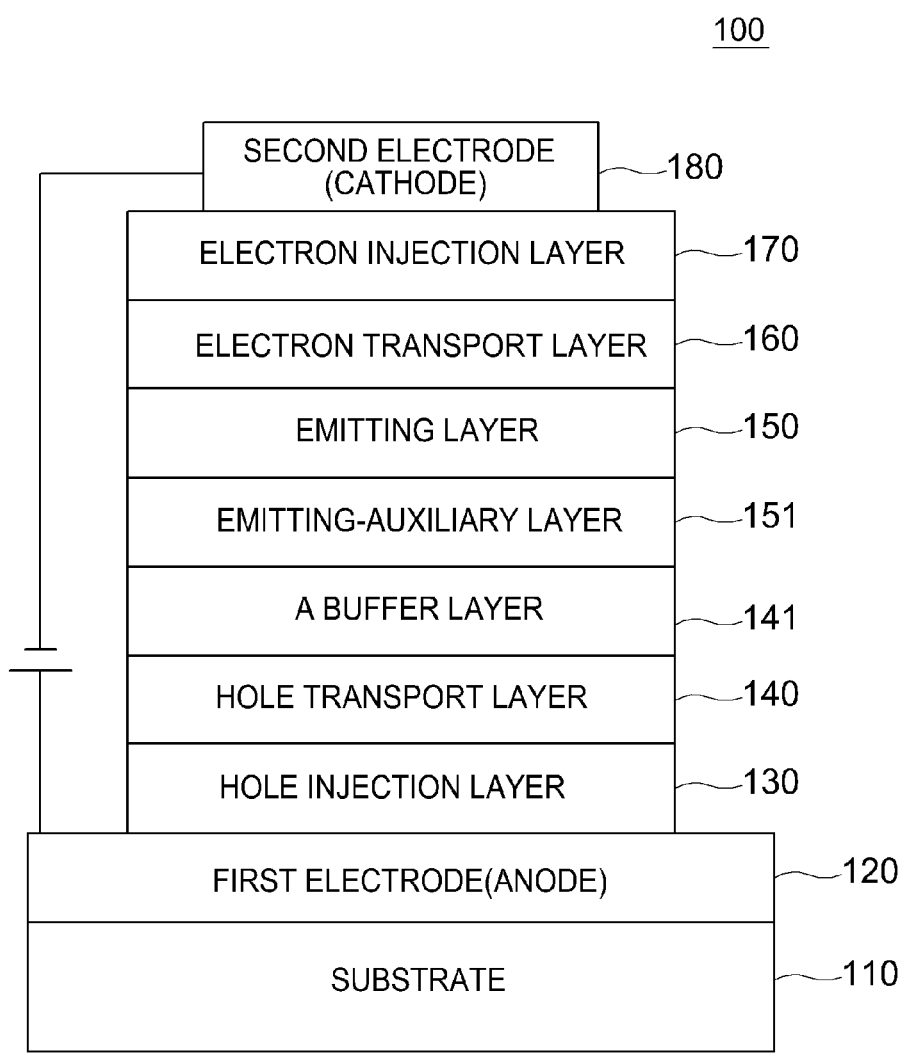

[Fig. 2]
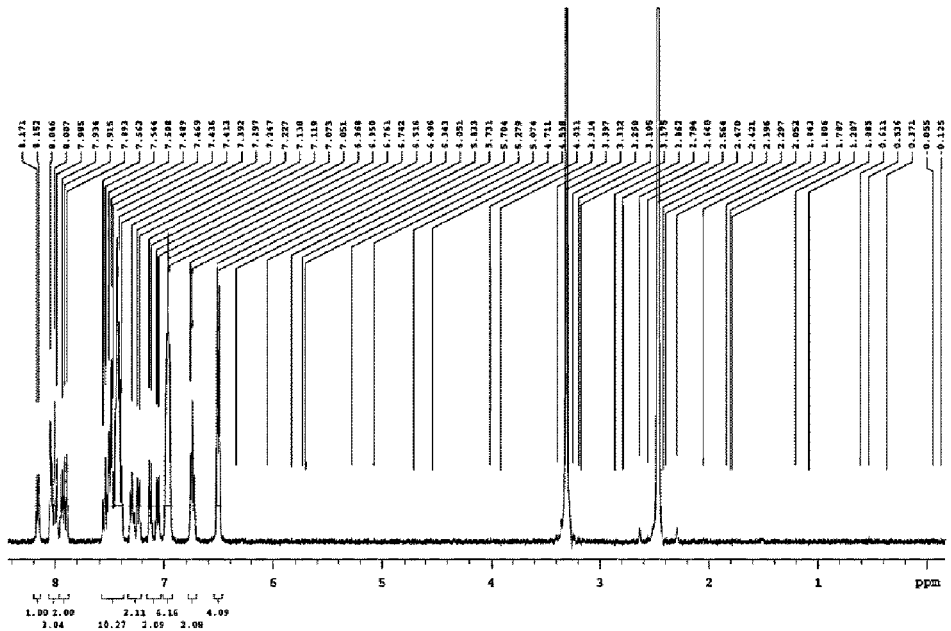
[Fig. 3]
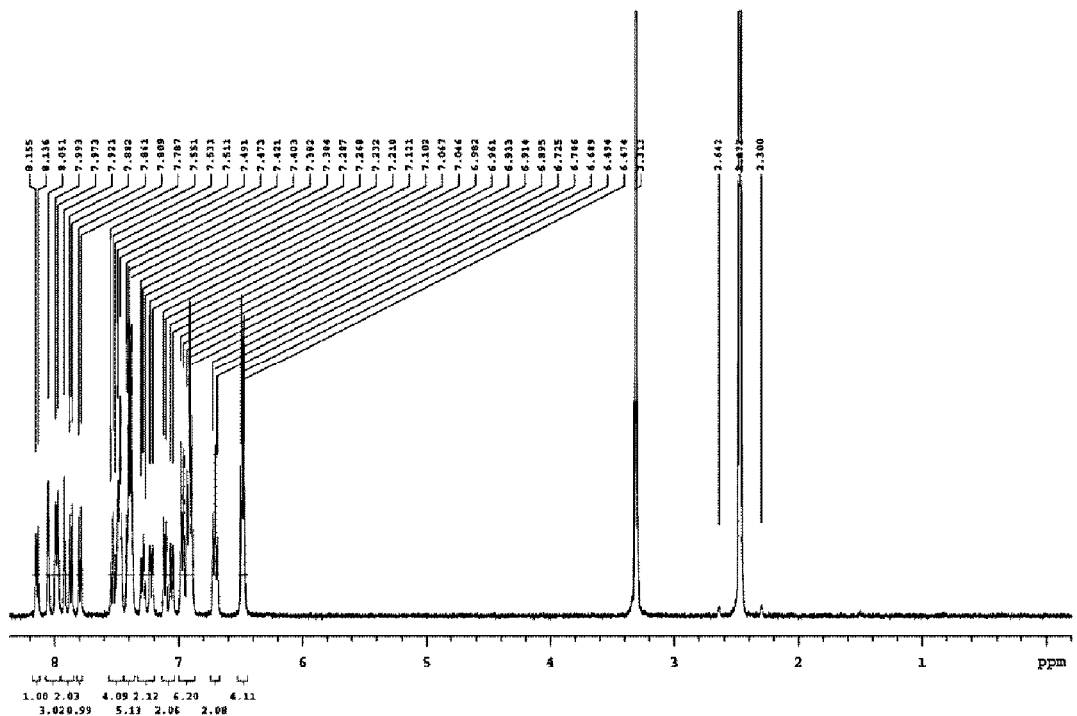

[Fig. 4]
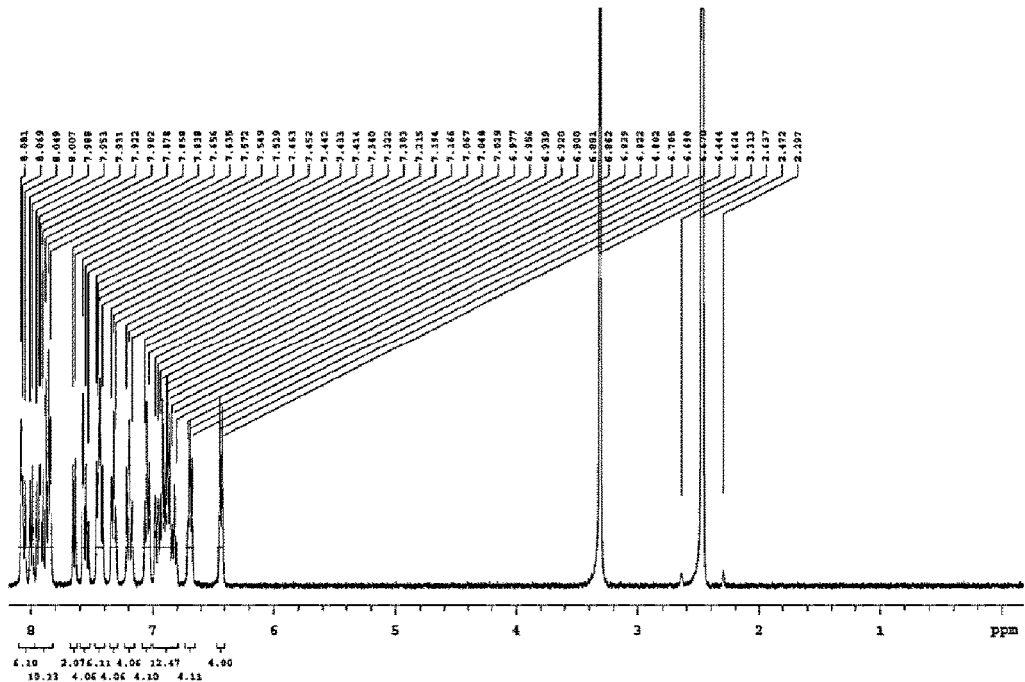
[Fig. 5]
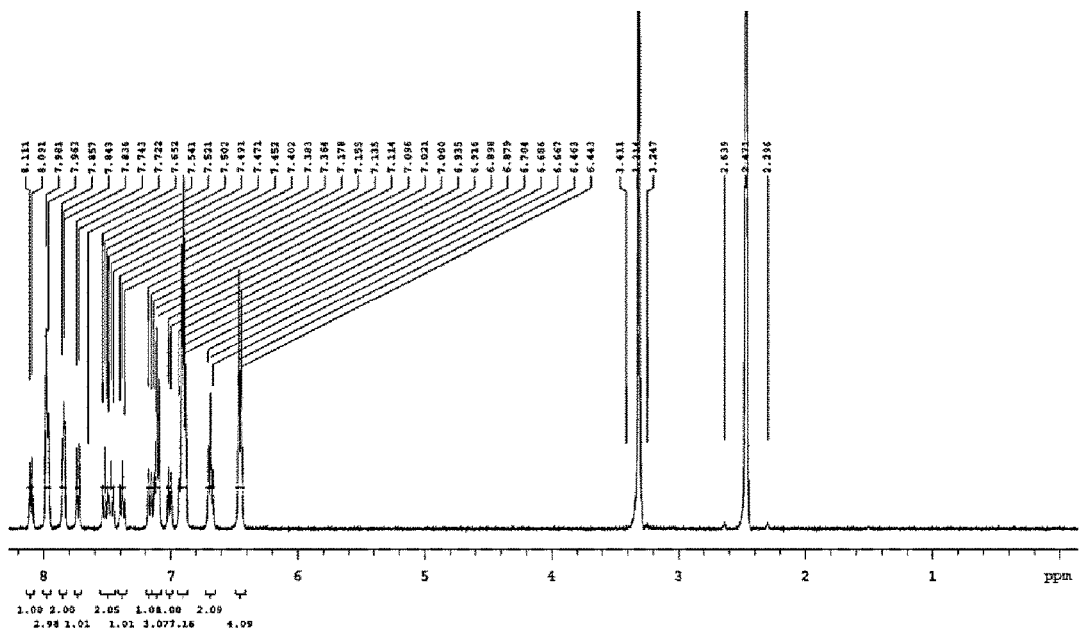

[Fig. 6]
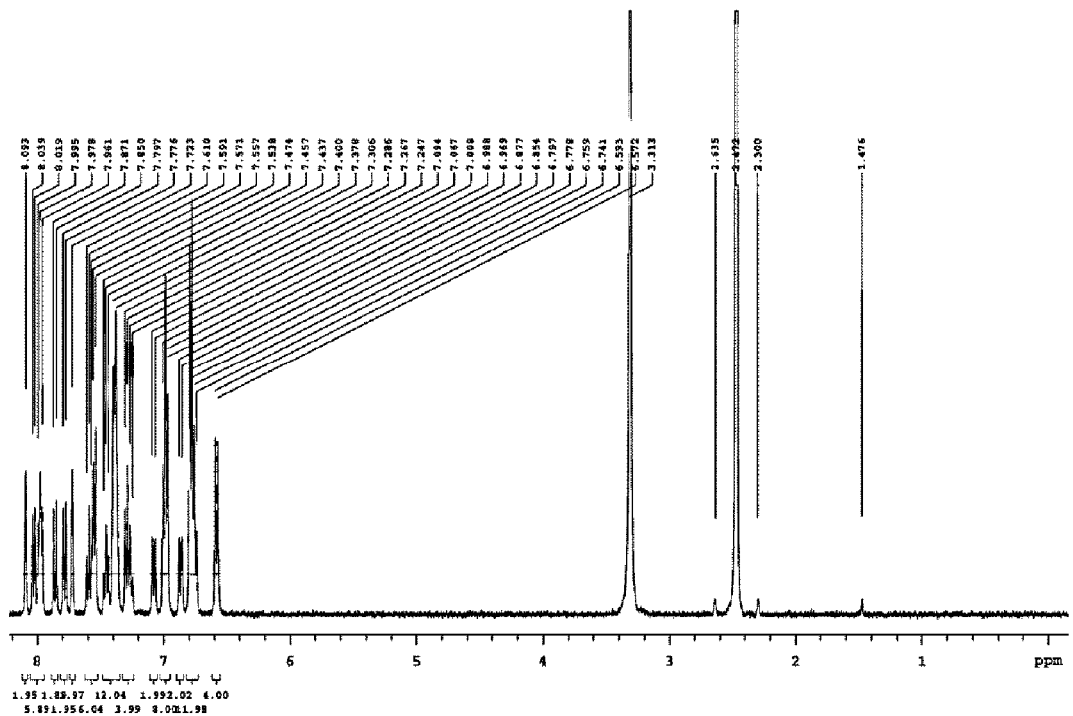

COMPOUND FOR ORGANIC ELECTRONIC ELEMENT, ORGANIC ELECTRONIC ELEMENT USING SAME AND ELECTRONIC DEVICE THEREFOR

BACKGROUND

Technical Field

The present invention relates to compound for organic electronic element, organic electronic element using the same, and an electronic device thereof.

Background Art

In general, organic light emitting phenomenon refers to a phenomenon that converts electronic energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function.

In the organic electroluminescent device, the most problematic is the lifetime and the efficiency. As the display becomes large, the efficiency and the lifetime problem must be solved.

Efficiency, life span, driving voltage and the like are related to each other. As the efficiency is increased, the driving voltage is relatively decreased, and as the driving voltage drops, the crystallization of the organic material due to joule heating generated during driving is reduced, and as a result, the life span tends to increase.

However, simply improving the organic material layer cannot maximize the efficiency. This is because, when the optimal combination of the energy level and T1 value between each organic material layer and the intrinsic properties (mobility, interface characteristics, etc.) of the material are achieved, long life and high efficiency can be achieved at the same time.

Further, recently, in organic electroluminescent devices, in order to solve the emission problem in the a hole transport layer, an emitting auxiliary layer must be present between the hole transport layer and an emitting layer, and it is necessary to develop different emitting auxiliary layers according to the respective emitting layers (R, G, B).

In general, electrons are transferred from the electron transport layer to the emitting layer, and holes are transferred from the hole transport layer to the emitting layer to generate excitons by recombination.

However, the material used for the hole transport layer has a low HOMO value and therefore has mostly low T1 value. As a result, the exciton generated in the emitting layer is transferred to the hole transport layer, resulting in charge unbalance in the emitting layer, and light is emitted at the interface of the hole transport layer.

When light is emitted at the interface of the hole transport layer, the color purity and efficiency of the organic electronic device are lowered and the life span is shortened. Therefore, it is urgently required to develop an emitting auxiliary layer having a high T1 value and a HOMO level between the HOMO energy level of the hole transport layer and the HOMO energy level of the emitting layer.

On the other hand, it is necessary to develop a hole injection layer material having stable characteristics, that is, a high glass transition temperature, against joule heating generated when the device is driven, while delaying penetration of the metal oxide from the anode electrode (ITO), which is one of the causes of shortening the lifetime of the organic electronic device, into the organic layer. The low glass transition temperature of the hole transport layer material has a characteristic that when the device is driven, the uniformity of the surface of the thin film is lowered, which has been reported to have a great influence on the lifetime of the device. In addition, OLED devices are mainly formed by a deposition method, and it is necessary to develop a material that can withstand long time in deposition, that is, a material having high heat resistance characteristics.

That is, in order to sufficiently exhibit the excellent characteristics of the organic electric element, a material for forming an organic material layer in an element such as a hole injection material, a hole transport material, a light emitting material, an electron transport material, an electron injection material, an emitting auxiliary layer material should be supported by stable and efficient materials. However, such a stable and efficient organic material layer material for an organic electric element has not been sufficiently developed yet. Therefore, development of new materials is continuously required, and development of materials for the hole transport layer or the emitting auxiliary layer is urgently required.

DETAILED DESCRIPTION OF THE INVENTION

Summary

In order to solve the problems of the background art described above, an embodiment of the present invention has revealed a compound having a novel structure, and that when the compound is applied to an organic electric element, the luminous efficiency, stability and lifetime of the device are greatly improved.

Accordingly, it is an object of the present invention to provide a novel compound, an organic electric element using the same, and an electronic device.

Technical Solution

The present invention provides a compound represented by the following Formula (1).

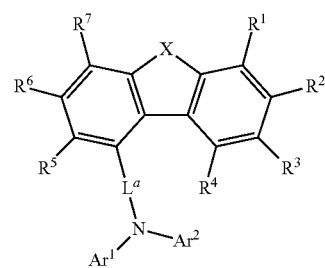

The present invention also provides an organic electric element using the compound represented by the above Formula and an electronic device thereof.

Effects of the Invention

By using the compound according to the present invention, it is possible to achieve a high luminous efficiency, a low driving voltage, and a high heat resistance of the device, and can greatly improve the color purity and lifetime of the device.

BRIEF DESCRIPTION OF THE DRAWINGS

FIG. 1 is an illustration of an organic electroluminescent device according to the present invention.

| | |
|---|---|
| 100: organic electric element, | 110 : substrate |
| 120 : the first electrode(anode), | 130 : the hole injection layer |
| 140 : the hole transport layer, | 141 : a buffer layer |
| 150 : the emitting layer, | 151 : the emitting auxiliary layer |
| 160 : the electron transport layer, | 170 : the electron injection layer |
| 180 : the second electrode(cathode) | |

FIG. 2 shows 1H NMR result of compound P-26.
FIG. 3 shows 1H NMR result of compound P-28.
FIG. 4 shows 1H NMR result of compound P-34.
FIG. 5 shows 1H NMR result of compound P-35.
FIG. 6 shows 1H NMR result of compound P-38.

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "linked" to another component, the component may be directly connected or connected to the other component, but another component may be "connected "," coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl", as used herein, includes an alkyl group substituted with a halogen.

Unless otherwise stated, the term "heteroalkyl", as used herein, means alkyl substituted one or more of carbon atoms consisting of an alkyl with hetero atom.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "alkenoxyl group", "alkenoxy group", "alkenyloxyl group" or "alkenyloxy group", as used herein, means an oxygen radical attached to an alkenyl group, but is not limited thereto, and has 2 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heteroalkyl", as used herein, means alkyl containing one or more of hetero atoms.

Unless otherwise stated, the term "heteroaryl group" or "heteroarylene group", as used herein, means a C2 to C60 aryl containing one or more of hetero atoms or arylene group, but is not limited thereto, and includes at least one of monocyclic and polycyclic rings, and may also be formed in conjunction with an adjacent group.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphatic ring and/or heteroaromatic ring. Also, the heterocyclic group may also be formed in conjunction with an adjacent group. Unless otherwise stated, the term "heteroatom", as used herein, represents at least one of N, O, S, P, or Si.

Also, the term "heterocyclic group" may include a ring containing $SO_2$ instead of carbon consisting of cycle. For example, "heterocyclic group" includes compound below.

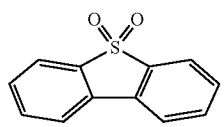

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Unless otherwise stated, the term "carbonyl", as used herein, is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether", as used herein, is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_3$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

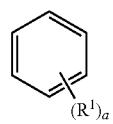

Wherein, when a is an integer of zero, the substituent $R^1$ is absent, that is, when a is 0, it means that hydrogen is bonded to all the carbons forming the benzene ring. In this case, the sign of the hydrogen bonded to the carbon may be omitted and the formula or compound may be described. When a is an integer of 1, the sole substituent $R^1$ is linked to any one of the carbon constituting the benzene ring, and when a is an integer of 2 or 3, they are respectively combined as follows, and when a is an integer from 4 to 6, it is bonded to the carbon of the benzene ring in a similar manner, and when a is an integer of 2 or more, $R^1$ may be the same or different from each other.

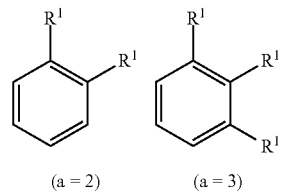

Unless otherwise expressly stated, the terms "ortho", "meta", and "para" used in the present invention refer to the substitution positions of all substituents, and the ortho position indicates the position of the substituent immediately adjacent to the compound, for example, when benzene is used, it means 1 or 2 position, and the meta position is the next substitution position of the neighbor substitution position, when benzene as an example stands for 1 or 3 position, and the para position is the next substitution position of the meta position, which means 1 and 4 position when benzene is taken as an example. A more detailed example of the substitution position is as follows, and it can be confirmed that the ortho-, and meta-position are substituted by non-linear type and para-positions are substituted by linear type.

Example of Ortho-Position

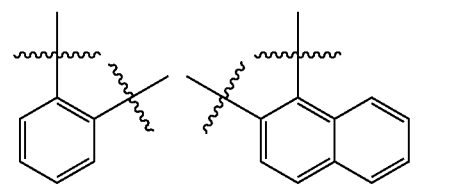

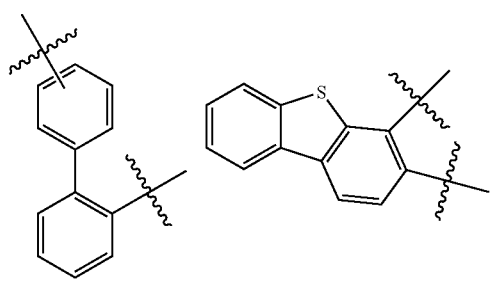

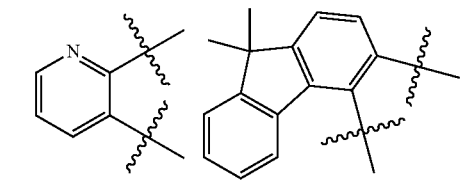

Example of Meta-Position

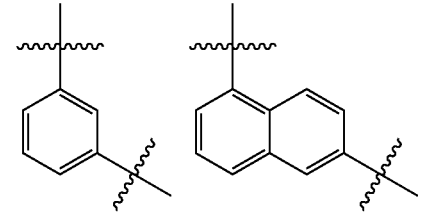

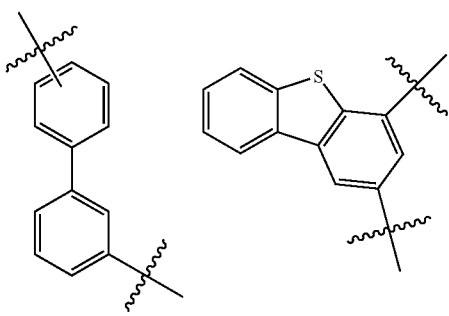

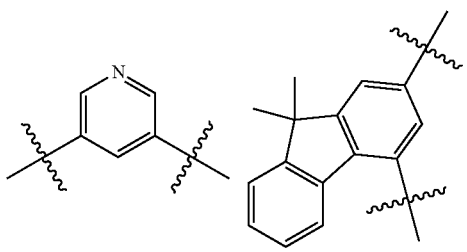

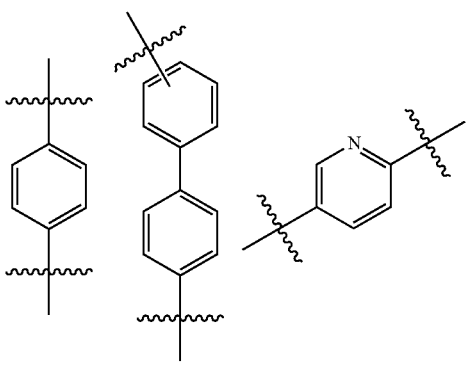

Example of Para-Position

Hereinafter, a compound according to an aspect of the present invention and an organic electric element comprising the same will be described.

The present invention provides a compound represented by the following Formula (1).

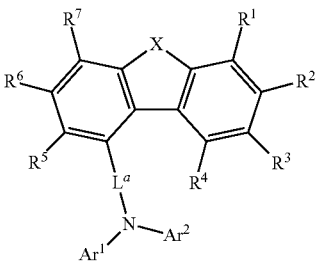
<Formula (1)>

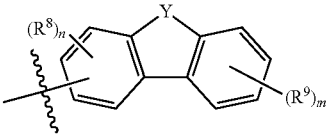
<Formula (2)>

{In Formula (1) and Formula (1-1),
1) X and Y are each independently O or S,
2) $R^{1'}$, $R^2$ and $R^3$ are each independently selected from the group consisting of hydrogen; deuterium; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_2$-$C_{20}$ alkoxyl group; a $C_6$-$C_{30}$ aryloxy group; and -$L^b$-$NAr^3Ar^4$;
with the proviso that one of $R^1$, $R^2$ and $R^3$ is -$L^b$-$NAr^3Ar^4$
3) $R^4$, $R^5$, $R^6$ and $R^7$ are each independently selected from the group consisting of hydrogen; deuterium; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_2$-$C_{20}$ alkoxyl group; a $C_6$-$C_{30}$ aryloxy group;
4) and wherein two adjacent $R^1$ and $R^2$, $R^2$ and $R^3$, $R^3$ and $R^4$, $R^5$ and $R^6$, $R^6$ and $R^7$ may be each independently bonded to form an aromatic or heteroaromatic ring,
5) $Ar^1$, $Ar^2$, $Ar^3$ and $Ar^4$ are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_2$-$C_{20}$ alkoxyl group; a $C_6$-$C_{30}$ aryloxy group; with the proviso that at least one of $Ar^1$, $Ar^2$, $Ar^3$ and $Ar^4$ is a substituent represented by Formula (1-1),
6) $L^a$ and $L^b$ are each independently single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group;
7) n is an integer of 0 to 3, and m is an integer of 0 to 4,
8) $R^8$ and $R^9$ are each independently selected from the group consisting of hydrogen; deuterium; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_2$-$C_{20}$ alkoxyl group; a $C_6$-$C_{30}$ aryloxy group; or in case n and m are 2 or more, and $R^8$ and $R^9$ are each in plural being the same or different, and a plurality of $R^8$ or a plurality of $R^9$ combine to each other to form an aromatic ring or an heteroaromatic ring, wherein, the aryl group, fluorenyl group, arylene group, heterocyclic group, fused ring group, alkyl group, alkenyl group, alkoxy group and aryloxy group may be substituted with one or more substituents selected from the group consisting of deuterium; halogen; a silane group substituted or unsubstituted with $C_1$-$C_{20}$ alkyl group or $C_6$-$C_{20}$ aryl group; siloxane group; a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group; wherein the substituents may combine each other and form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination of thereof.}

In Formula (1) and Formula (1-1) of the present invention, when $Ar^1$, $Ar^2$, $Ar^3$, $Ar^4$, and $R^1$, $R^2$, $R^3$, $R^4$, $R^5$, $R^6$, $R^7$, $R^8$, $R^9$ are aryl groups, it is preferably $C_6$-$C_{30}$ aryl group, more preferably $C_6$-$C_{24}$ aryl group, and when $Ar^1$, $Ar^2$, $Ar^3$, $Ar^4$, and $R^1$, $R^2$, $R^3$, $R^4$, $R^5$, $R^6$, $R^7$, $R^8$, $R^9$ are heterocyclic groups, it is preferably a $C_2$-$C_{40}$ heterocyclic group, more preferably a $C_2$-$C_{30}$ heterocyclic group, still more preferably a $C_2$-$C_{24}$ heterocyclic group.

When $Ar^1$, $Ar^2$, $Ar^3$, $Ar^4$, and $R^1$, $R^2$, $R^3$, $R^4$, $R^5$, $R^6$, $R^7$, $R^8$, $R^9$ are aryl groups, specific examples thereof include phenyl, biphenyl, terphenyl, quaterphenyl, styrene, naphthyl, anthracenyl, phenanthryl, pyrenyl, perylenyl, klycenyl, triphenylene group, and the like. When $Ar^1$, $Ar^2$, $Ar^3$, $Ar^4$, and $R^1$, $R^2$, $R^3$, $R^4$, $R^5$, $R^6$, $R^7$, $R^8$, $R^9$ are fluorenyl groups, it may specifically be 9,9-dimethyl-9H-fluorene, 9,9-diphenyl-9H-fluorene, 9,9'-spirobifluorene, or the like. When $Ar^1$, $Ar^2$, $Ar^3$, $Ar^4$, and $R^1$, $R^2$, $R^3$, $R^4$, $R^5$, $R^6$, $R^7$, $R^8$, $R^9$ are heterocyclic groups, specific examples thereof include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a pyrazine group, a triazole group, an acridyl group, a pyridazine group, a pyrazinyl group, a quinolinyl group, a quinazolinyl group, a quinoxalinyl group, a benzoquinoxaline, a dibenzoquinoxaline, a phthalazinyl group, a pyridopyrimidinyl group, a pyridopyrazinyl group, a pyrazinopyrazinyl group, an isoquinoline group, an indole group, a carbazole group, indolocarbazole, acridine, phenoxazine, benzopyridazine, benzopyrimidine, carboline, benzocarboline, benzoxazole group, a benzoimidazole group, a benzothiazole group, a benzocarbazole group, a benzothiophene group, a benzofuranyl group, a phenanthroline group, a thiazolyl group, an isoxazolyl group, an oxadiazolyl group, a thiadiazolyl group, a benzothiazolyl group, a phenothiazinyl group, thienothiophene, benzothienopyridine, benzothienopyrimidine, benzofuropyrimidine, dimethylbenzoindenopyrimidine, phenanthropuropyrimidine, naphthopuropyrimidine, naphthothienopyrimidine, thianthrene, dihydrobenzothiophenopyrazine, dihydrobenzofuropyrazine, dibenzothiophene group, dibenzofuranyl group, benzonaphthothiophene, naphthobenzofuran, benzophenanthrothiophene, phenanthrobenzofuran and the like, but are not limited thereto.

Also, when $L^a$ or $L^b$ in Formula (1) of the present invention is an arylene group, it may preferably be an $C_6$-$C_{30}$ arylene group, more preferably an $C_6$-$C_{18}$ arylene group, illustratively, it may be phenylene, biphenyl, terphenyl, naphthalene, anthracene, phenanthrene, and the like. Preferably, at least one of $L^a$ and $L^b$ in Formula (1) of the present invention may be represented by a single bond.

Formula (1) of the present invention provides a compound represented by any one of the following Formulas (2) to (7).

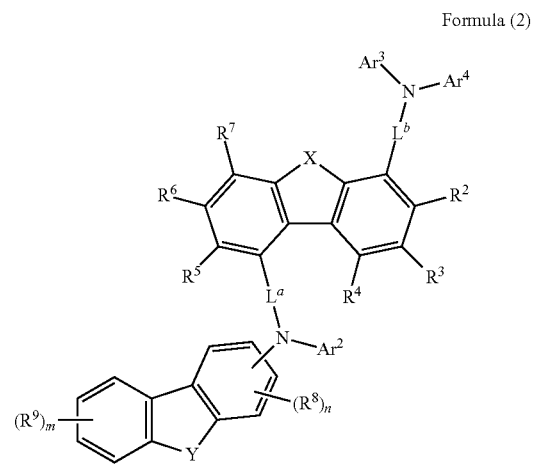

Formula (2)

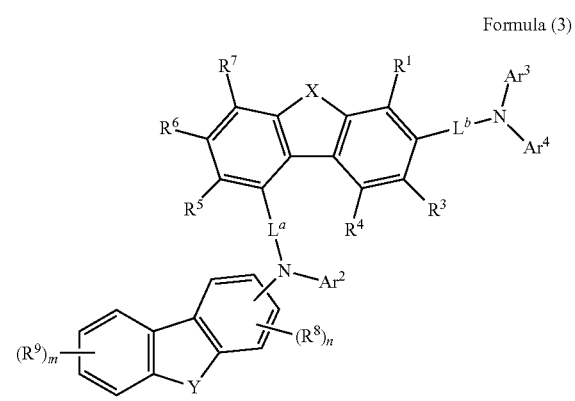

Formula (3)

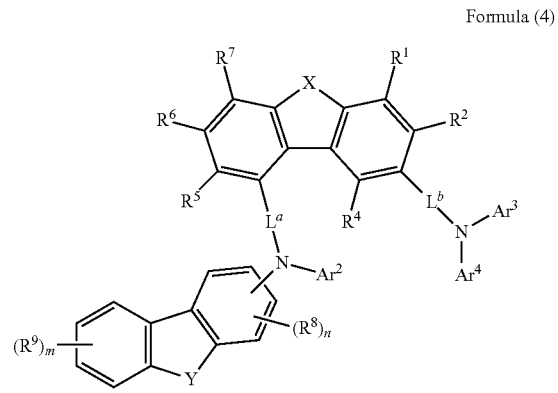

Formula (4)

Formula (5)

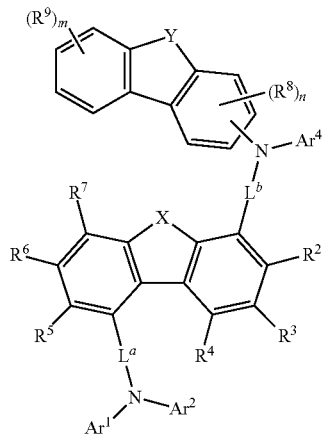

Formula (6)

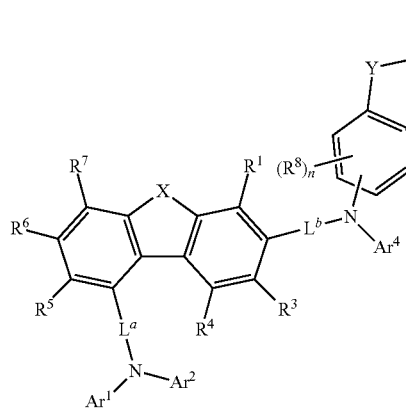

Formula (7)

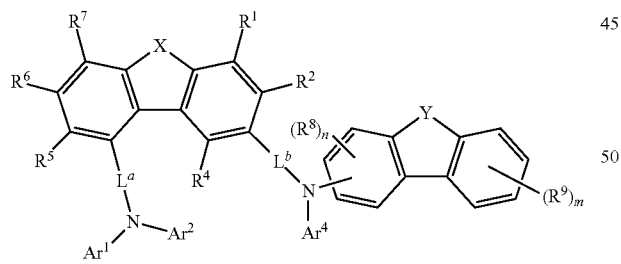

{In Formulas (2) to (7),
X, Y, $Ar^1$, $Ar^2$, $Ar^3$, $Ar^4$, $L^a$, $L^b$, $R^1$, $R^2$, $R^3$, $R^4$, $R^5$, $R^6$, $R^7$, $R^8$, $R^9$, n and m are the same as defined in Formula (1) and (1-1).}

In Formula (1) of the present invention, at least one of $Ar^1$ and $Ar^2$ is represented by Formula 1-1, and at least one of $Ar^3$ and $Ar^4$ may be a compound represented by Formula 1-1.

As another specific example, the present invention comprises compounds wherein the compound represented by Formula (1) is represented by the following Formulas P-1 to P-90.

P-1

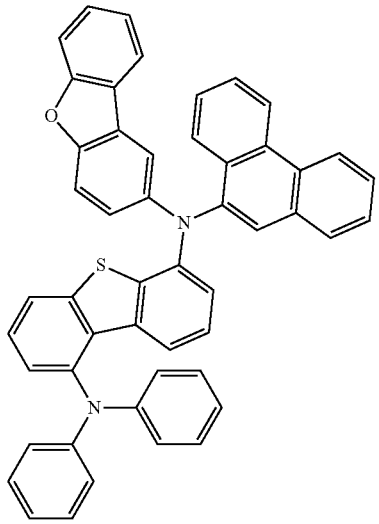

P-2

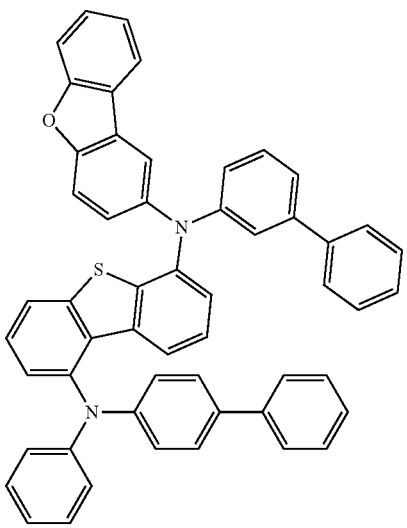

P-3

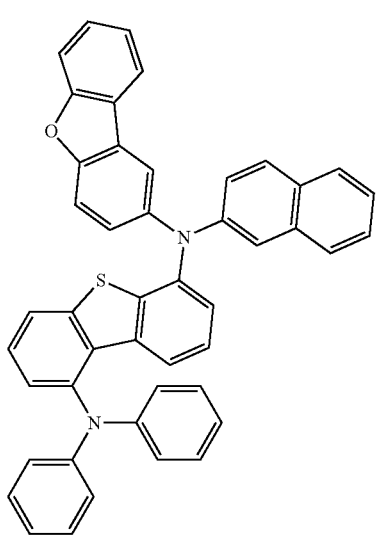

P-4
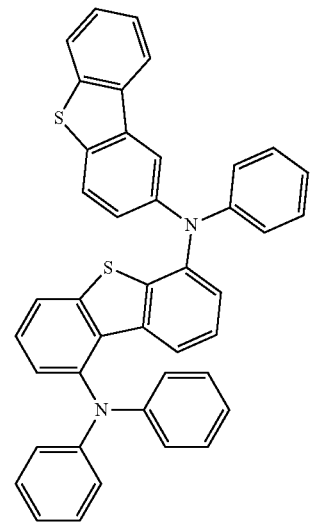
P-5
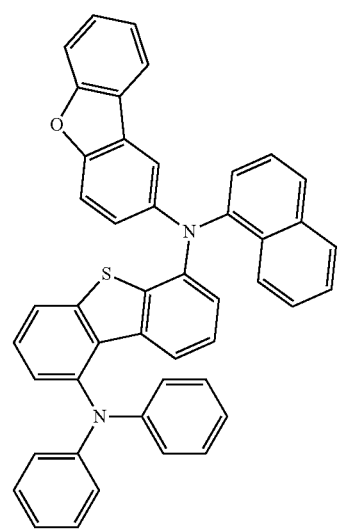
P-6
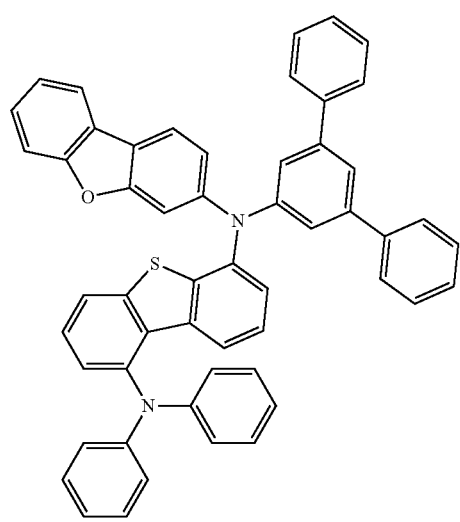
P-7
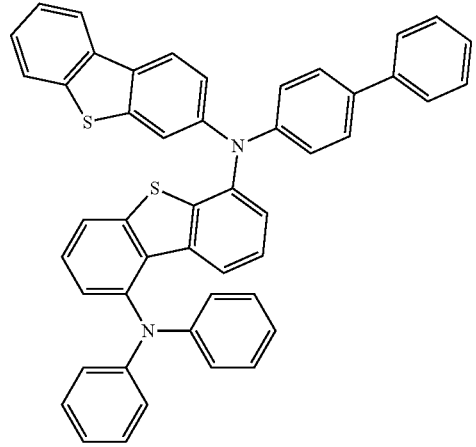
P-8
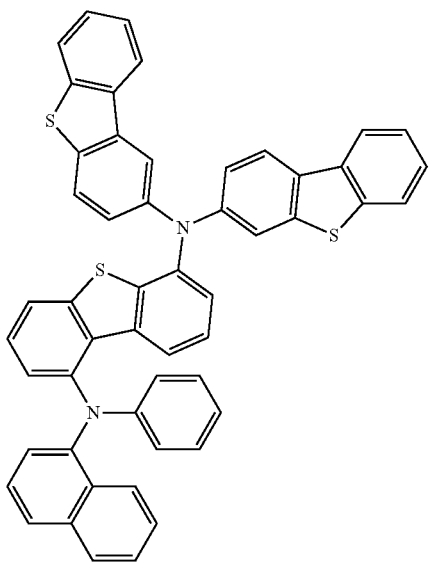
P-9
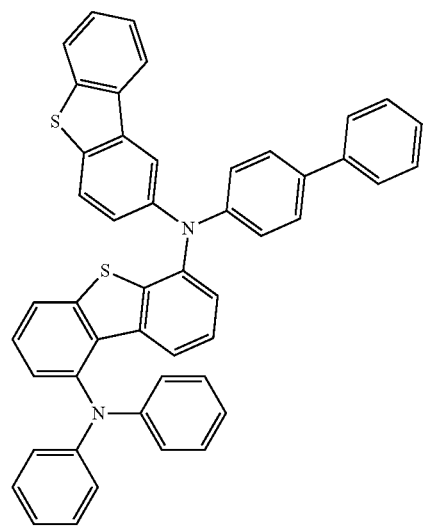

P-10
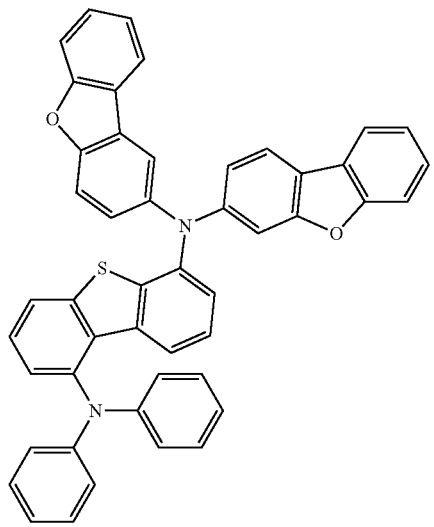
P-11
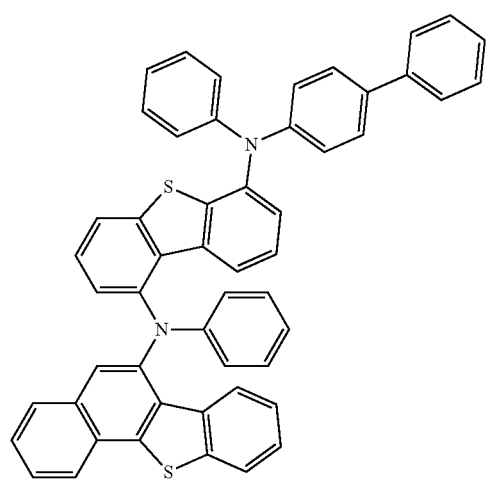
P-12
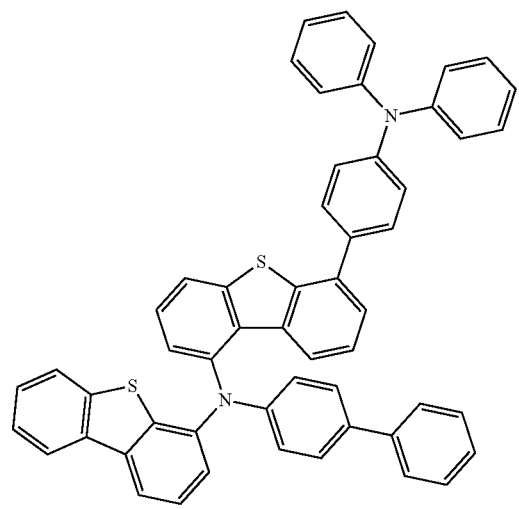
P-13
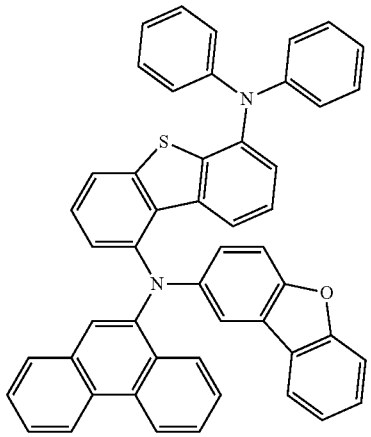
P-14
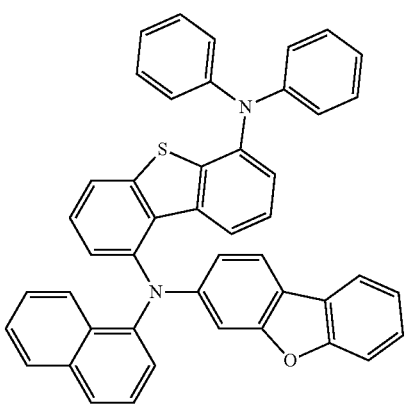
P-15
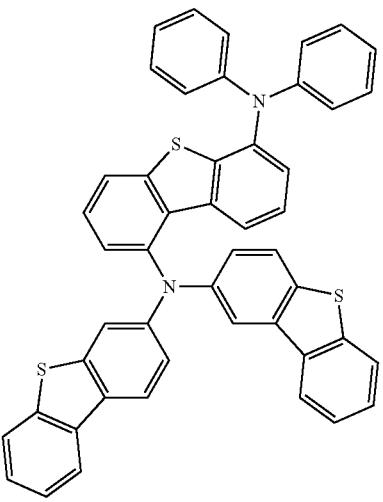

P-16
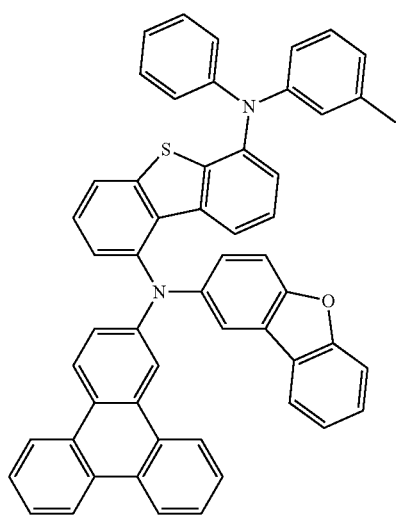
P-17
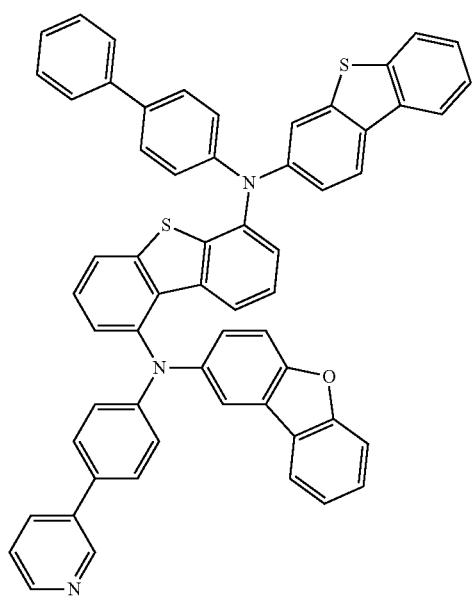
P-18
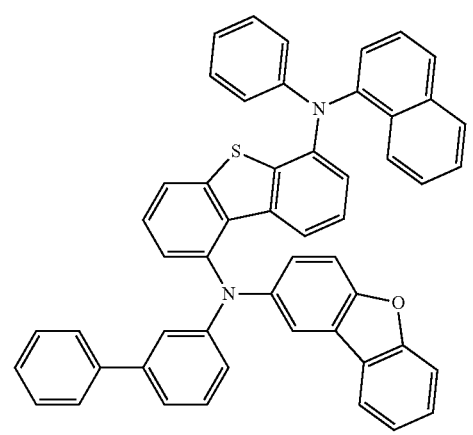
P-19
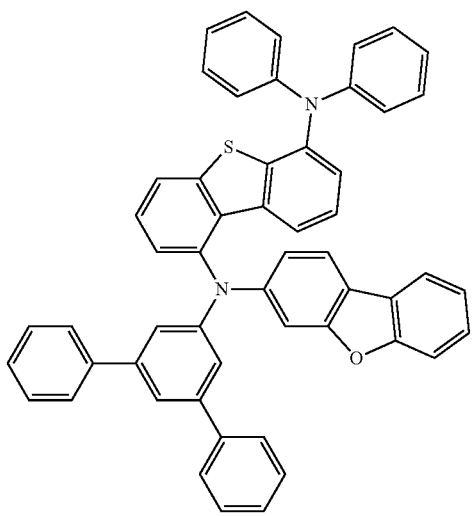
P-20
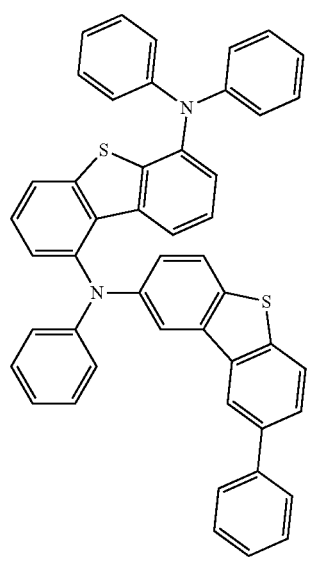
P-21
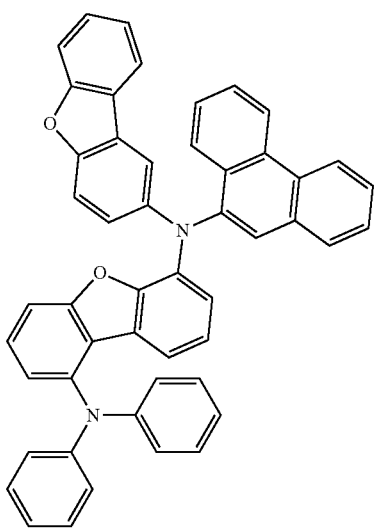

P-22
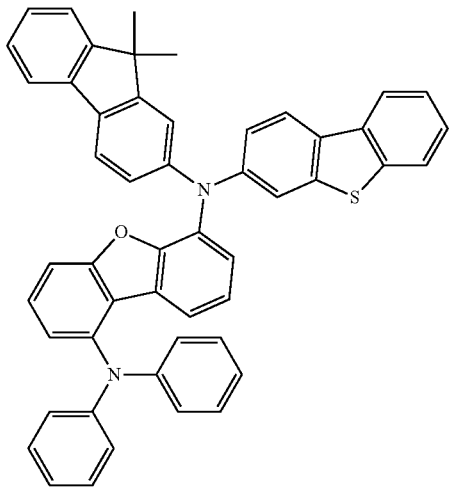
P-23
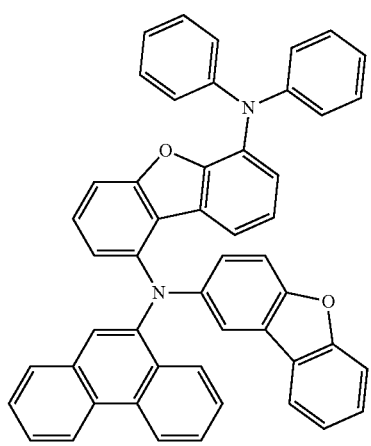
P-24
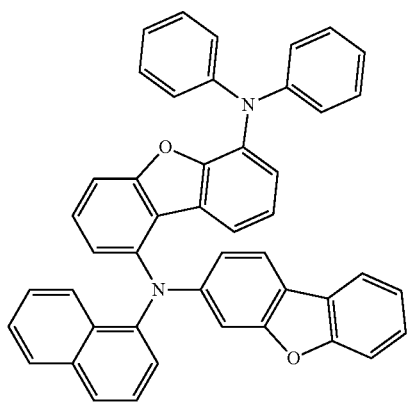
P-25
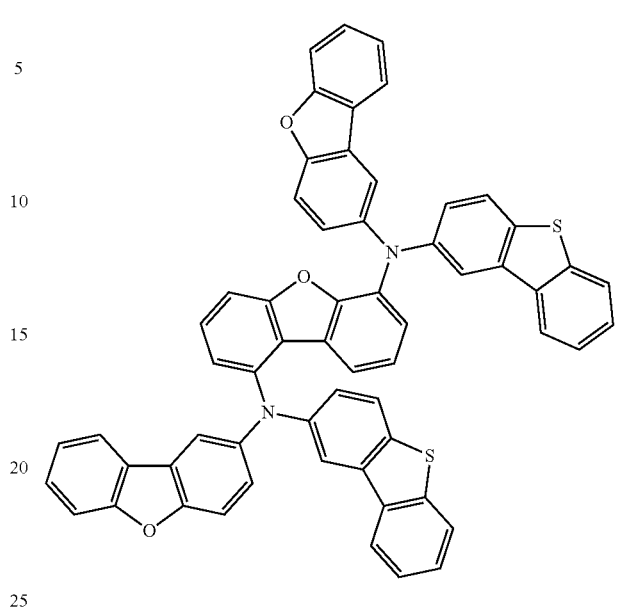
P-26
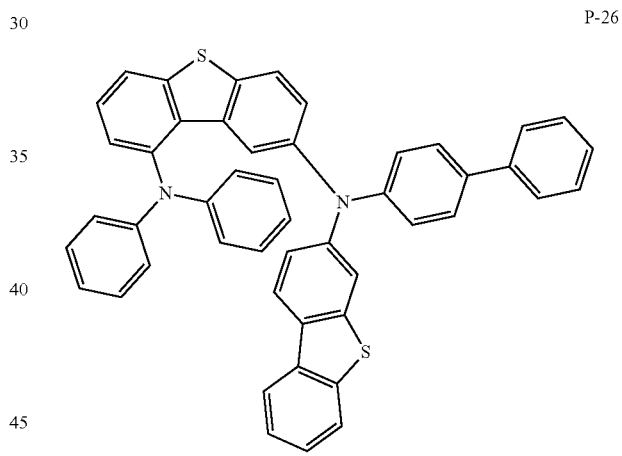
P-27
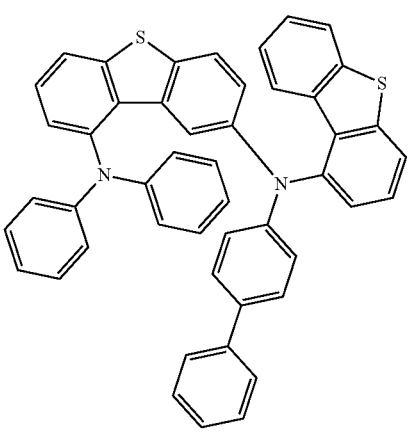

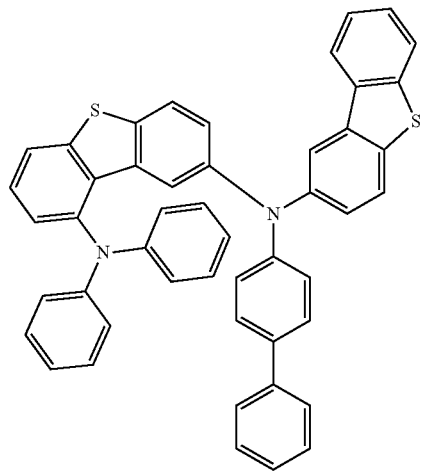
P-28
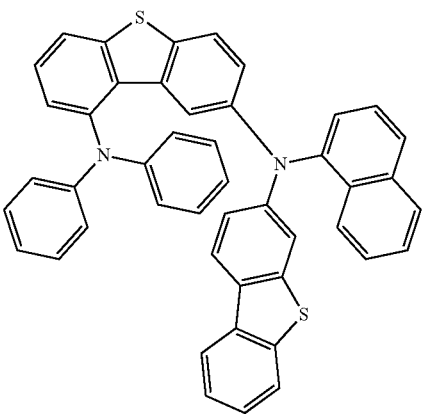
P-31
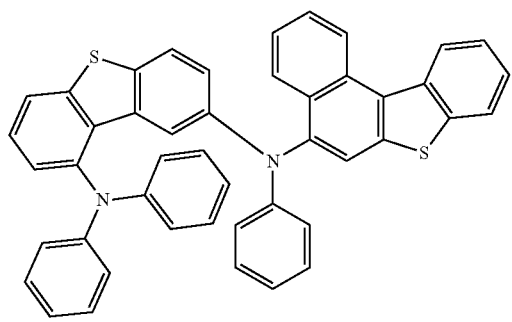
P-29
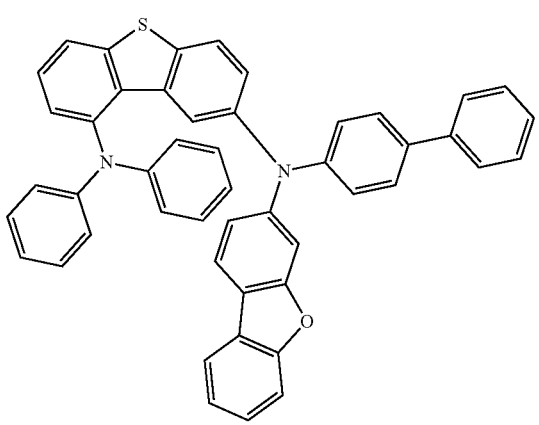
P-32
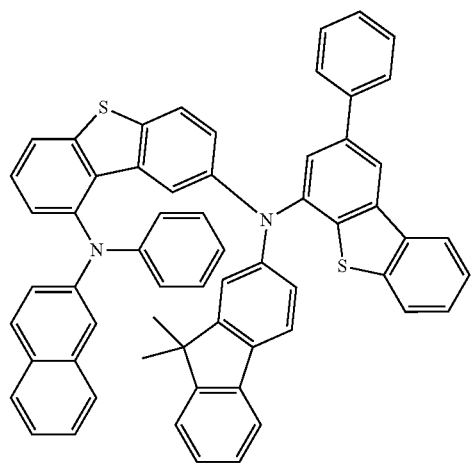
P-30
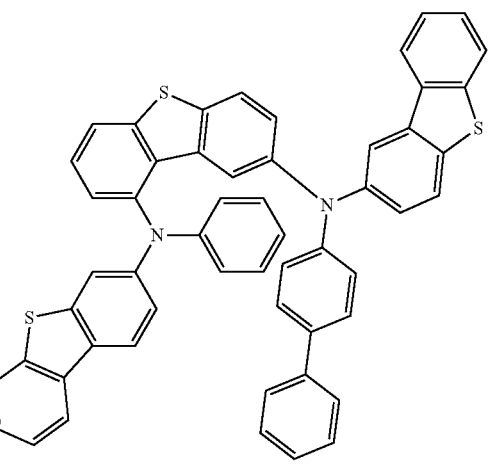
P-33

P-34
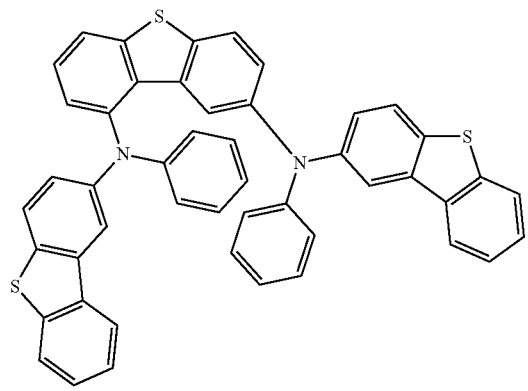
P-35
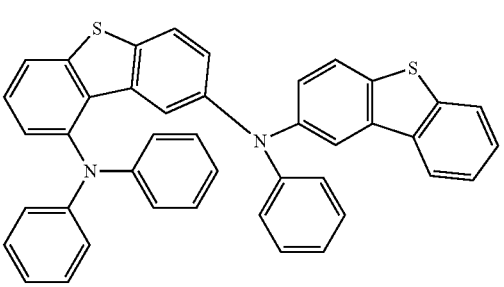
P-36
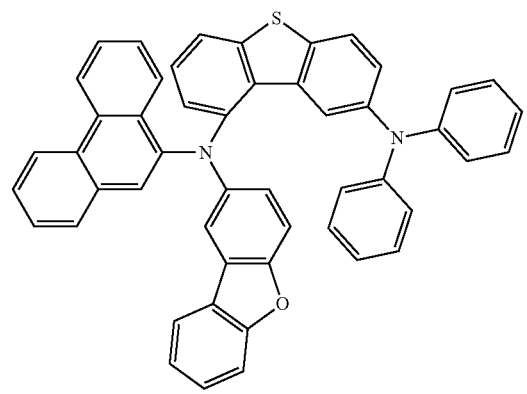
P-37
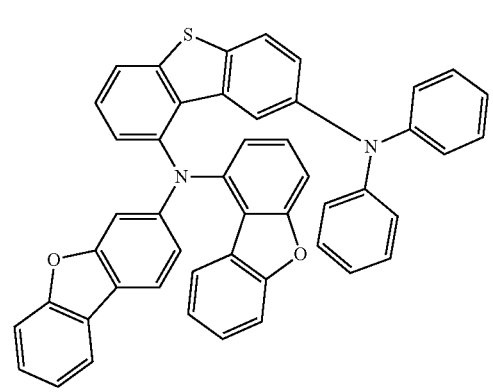
P-38
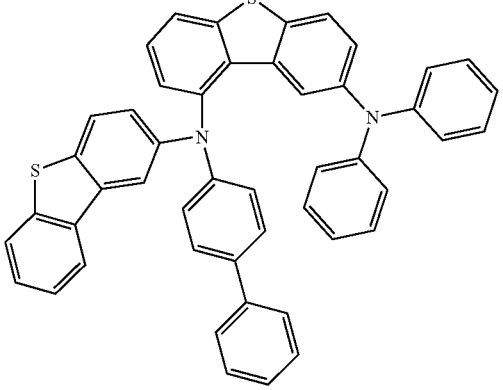
P-39
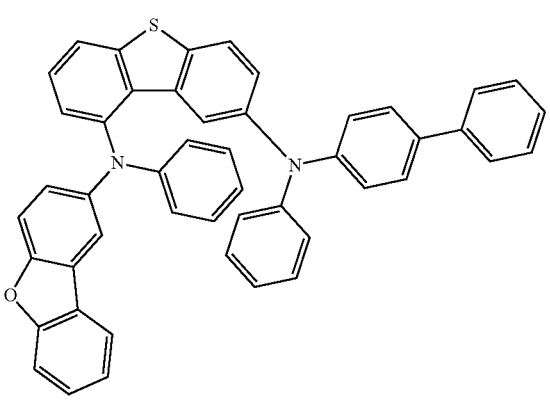
P-40
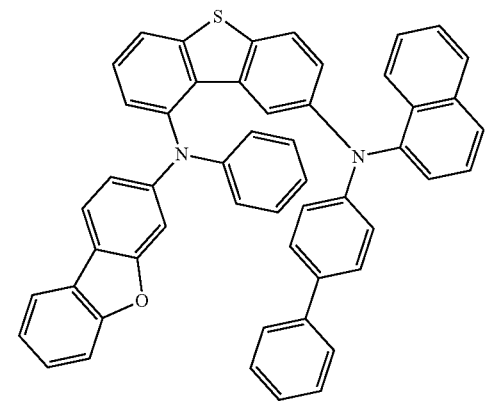
P-41
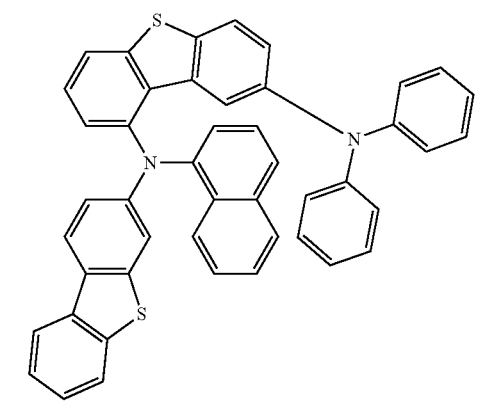

P-42
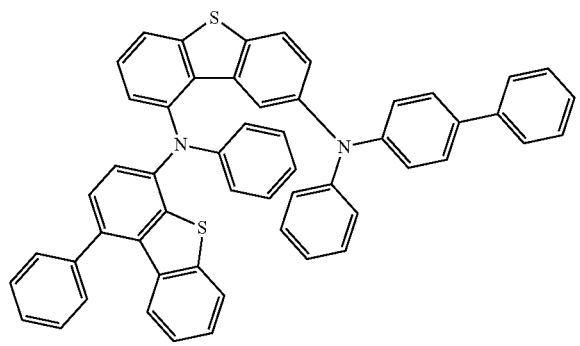
P-43
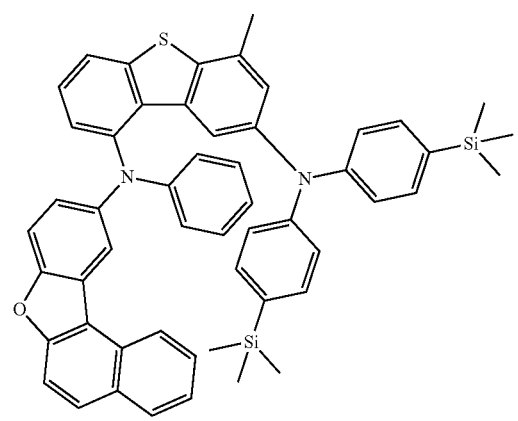
P-44
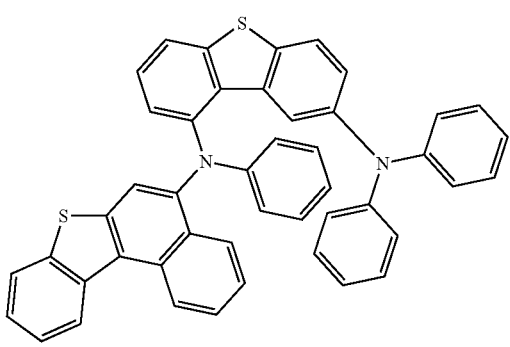
P-45
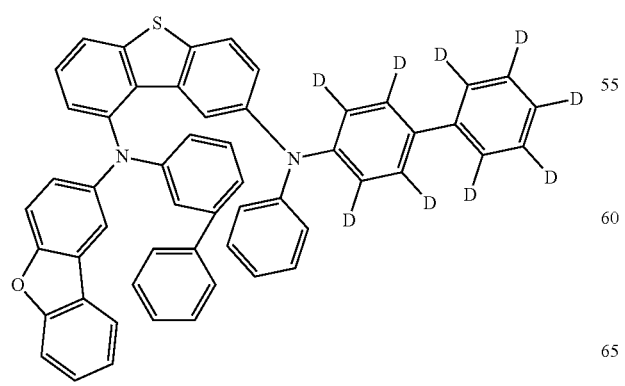
P-46
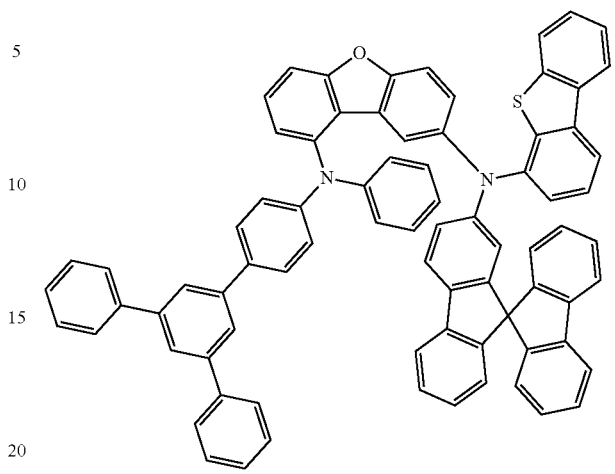
P-47
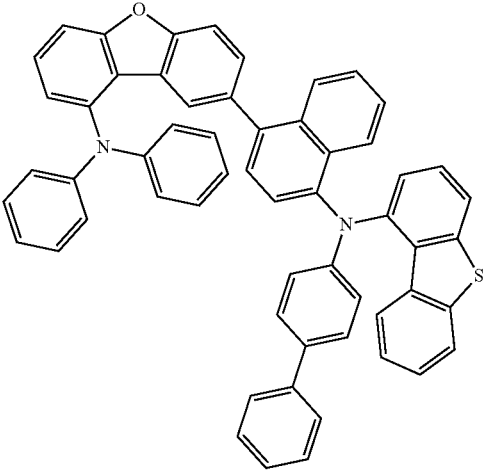
P-48
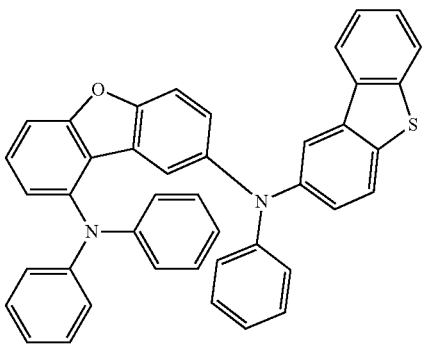

P-49
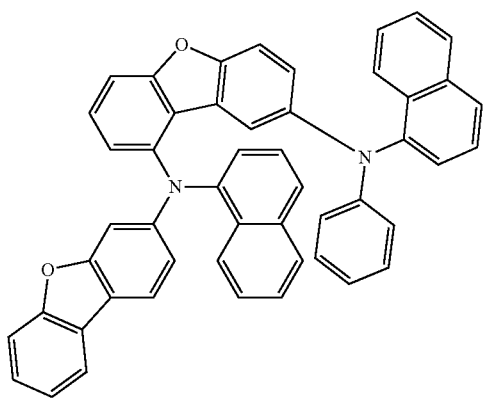
P-50
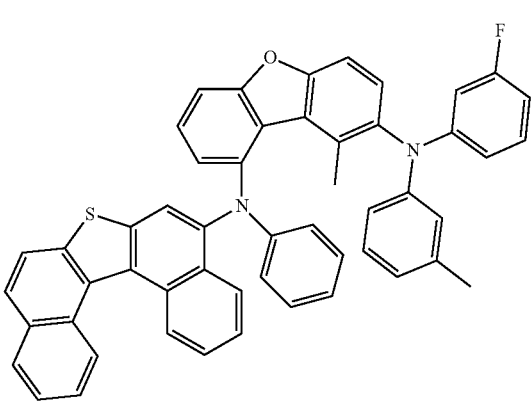
P-51
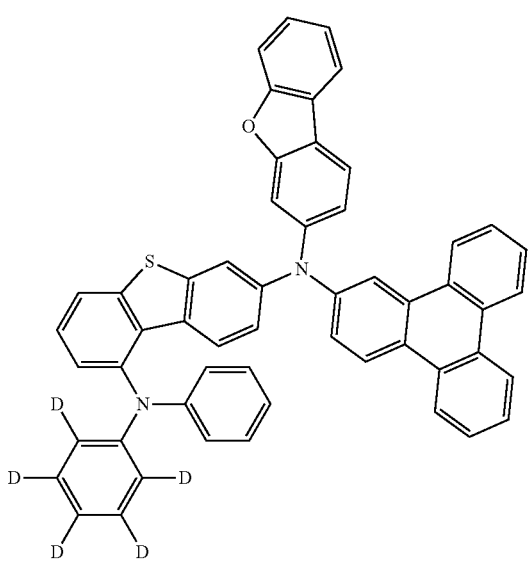
P-52
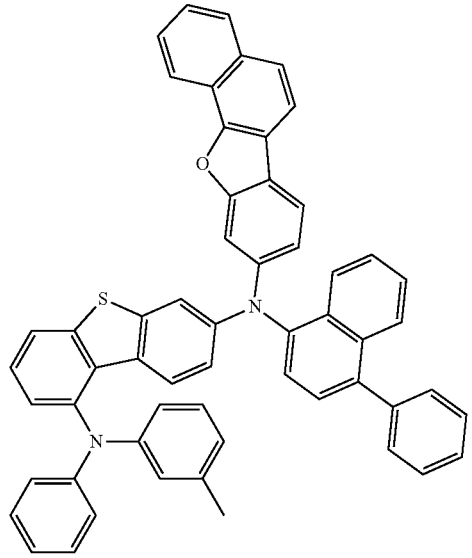
P-53
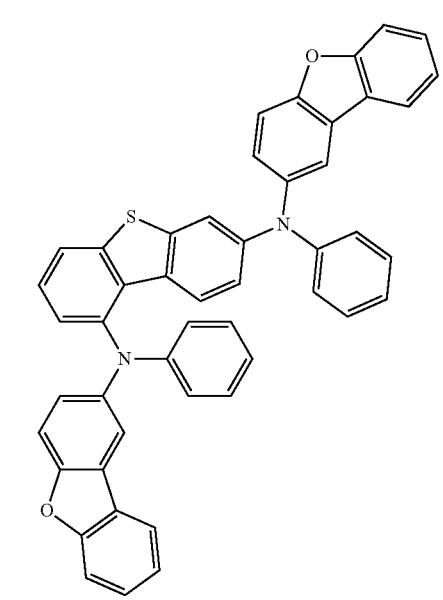
P-54
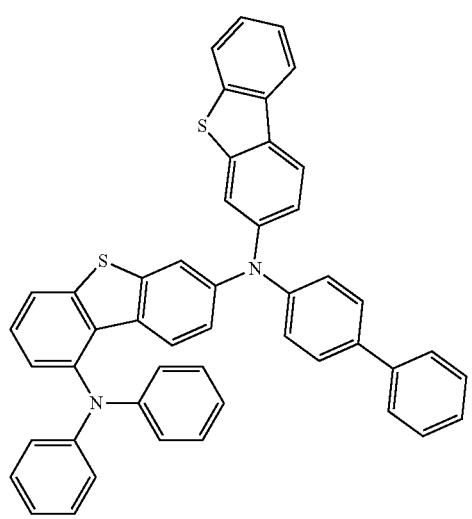

P-55
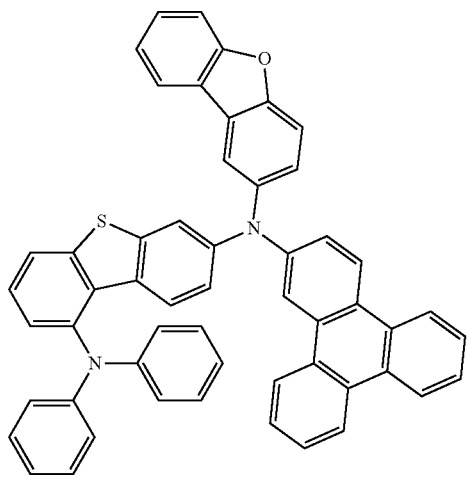
P-56
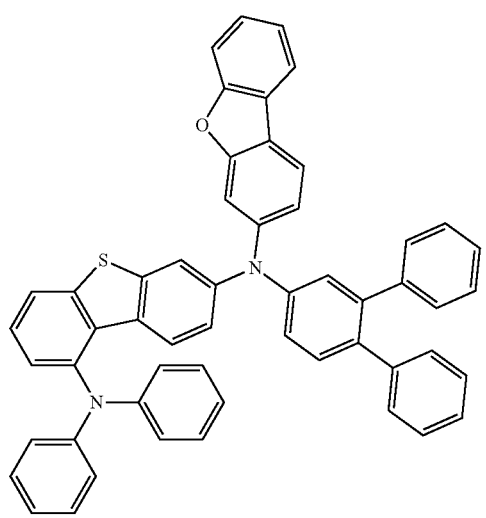
P-57
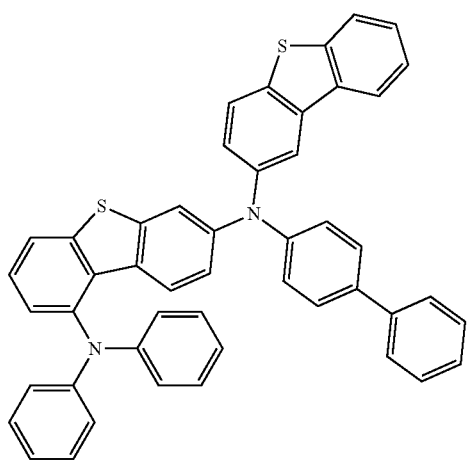
P-58
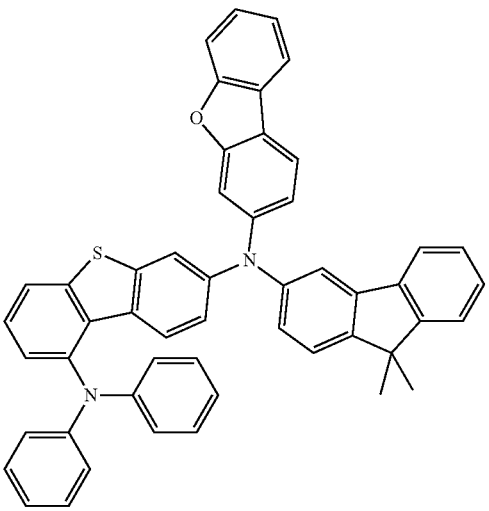
P-59
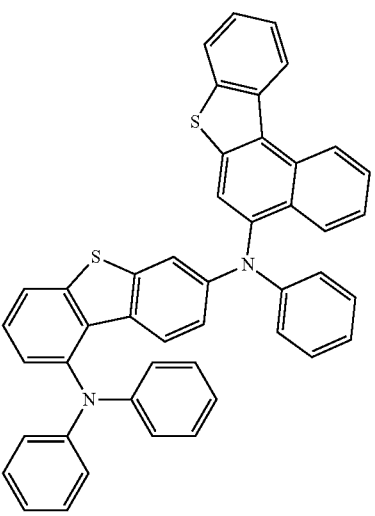
P-60
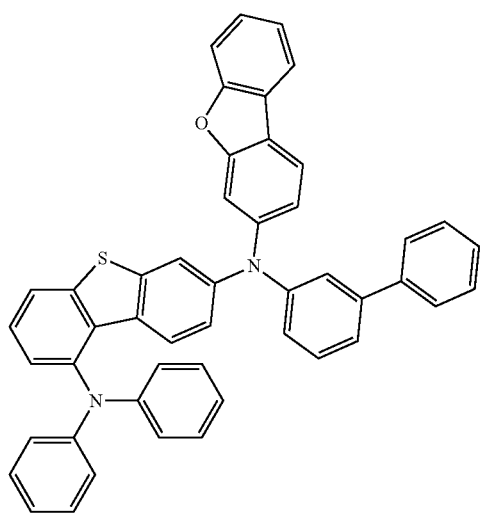

P-61
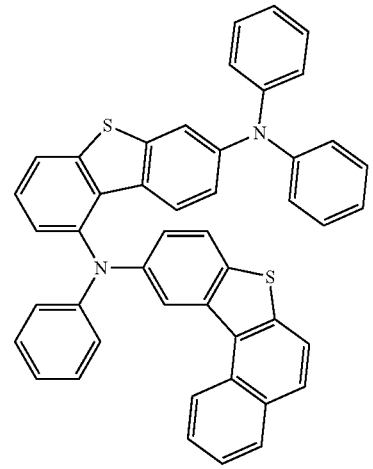
P-62
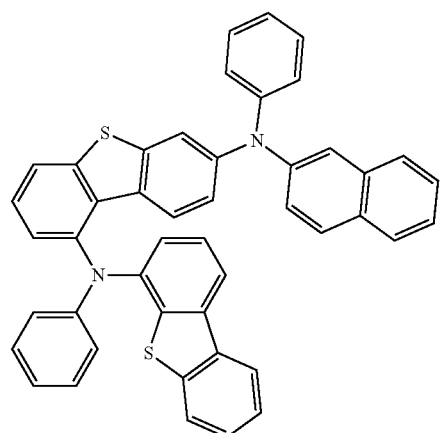
P-63
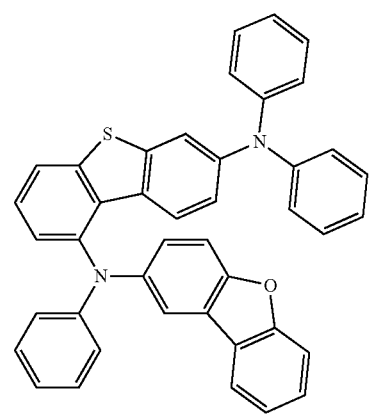
P-64
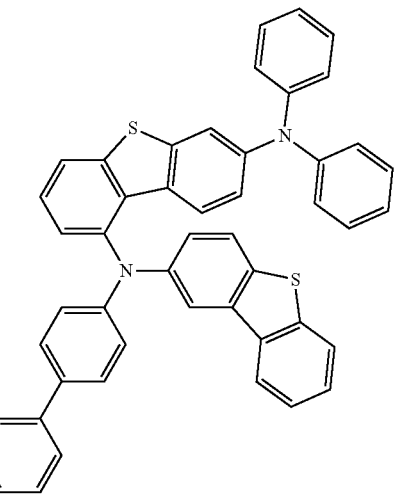
P-65
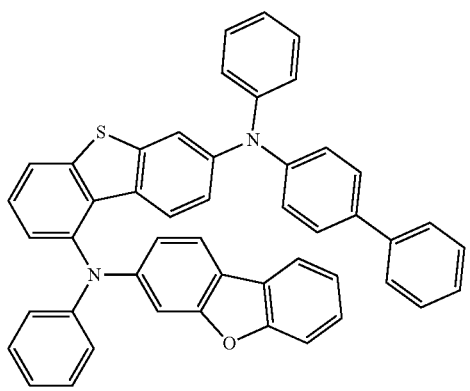
P-66
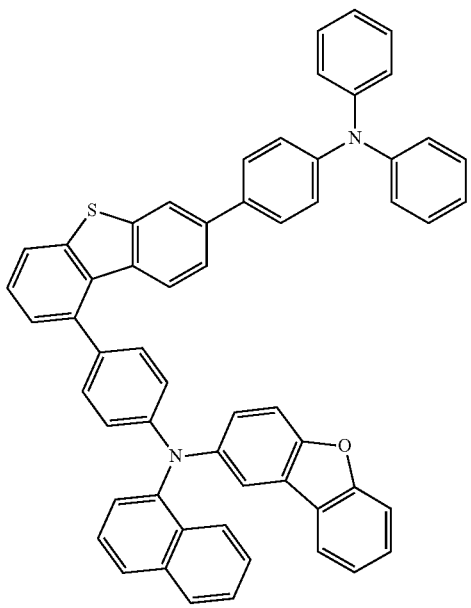

P-67
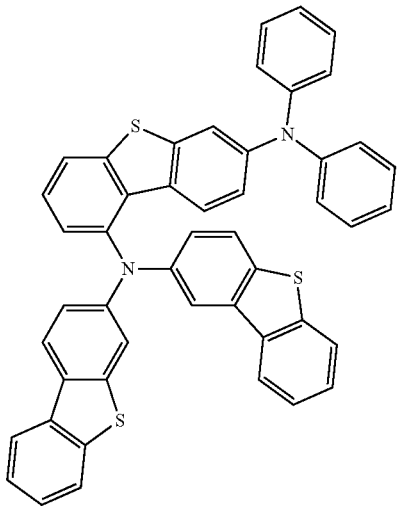
P-68
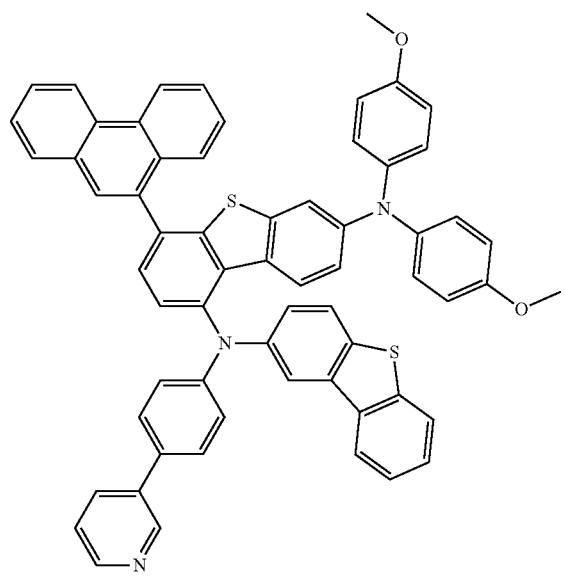
P-69
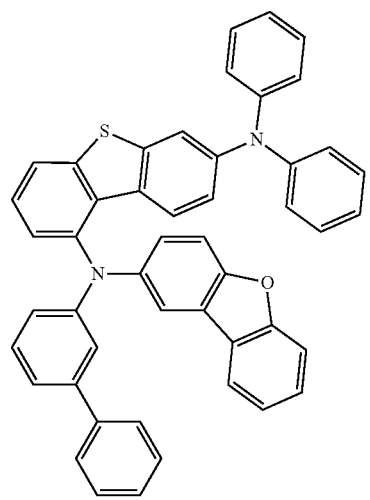
P-70
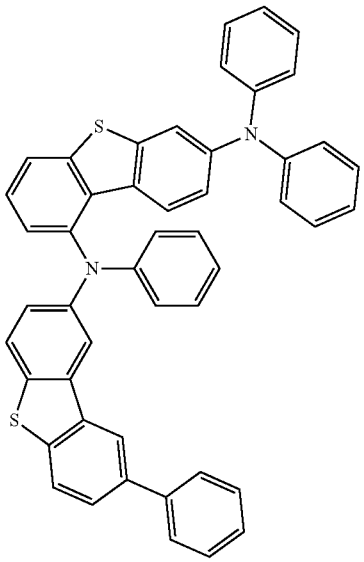
P-71
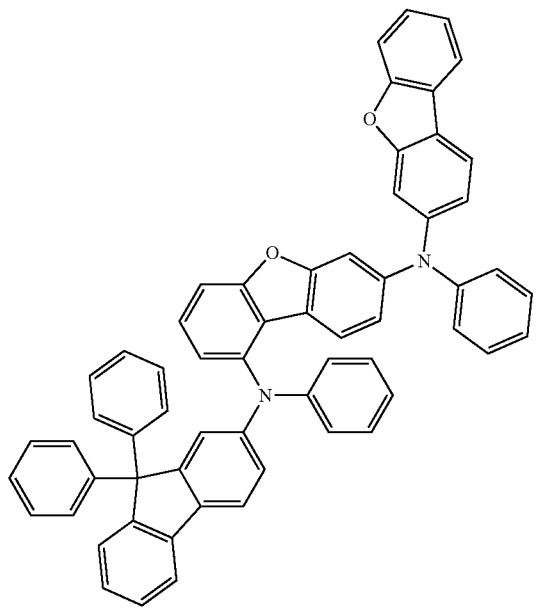
P-72
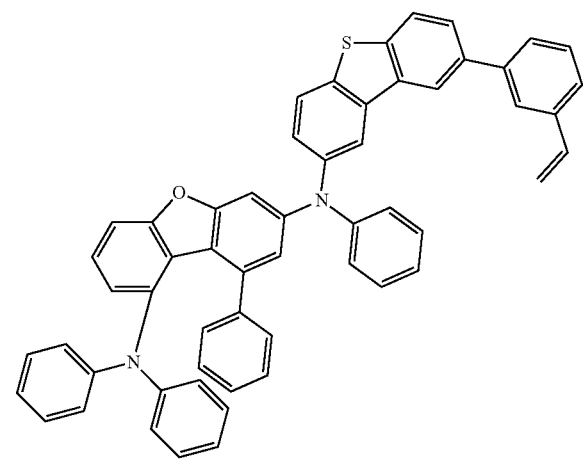

P-73
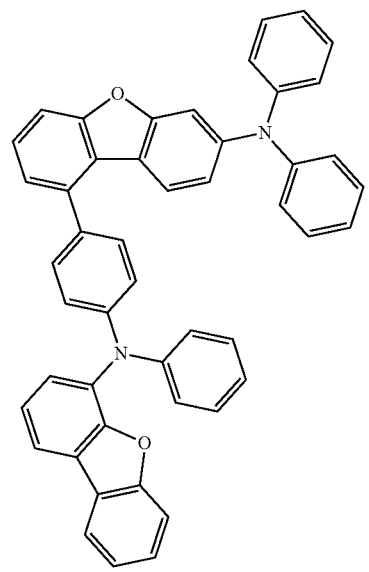
P-74
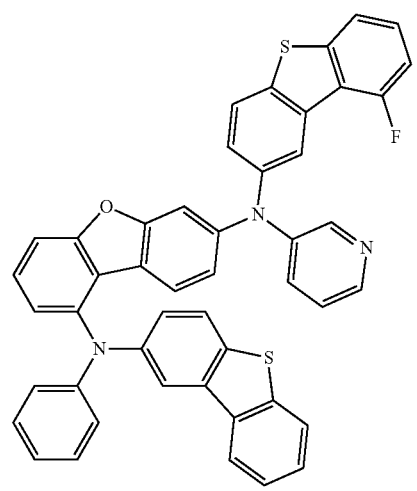
P-75
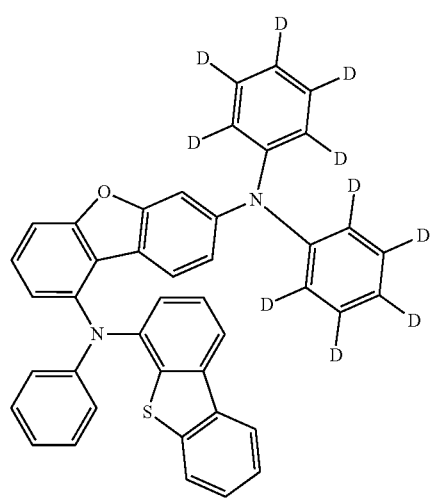
P-76
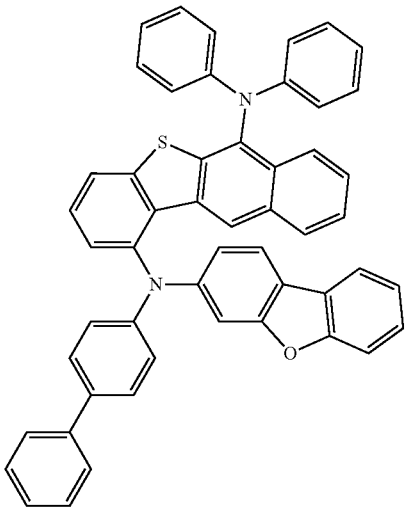
P-77
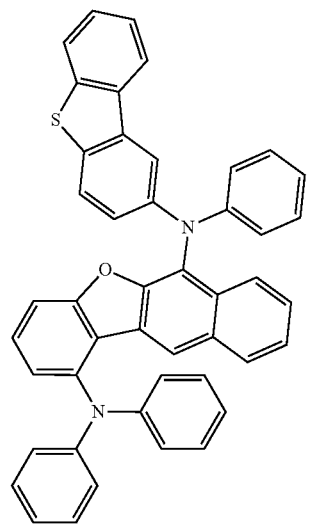
P-78
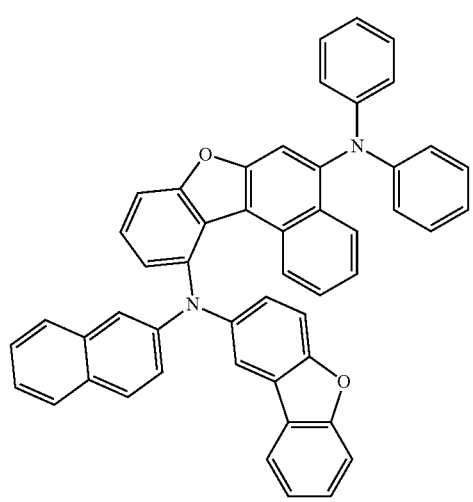

P-79
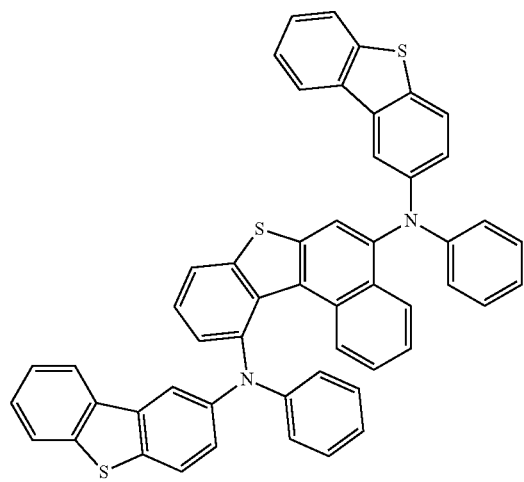
P-80
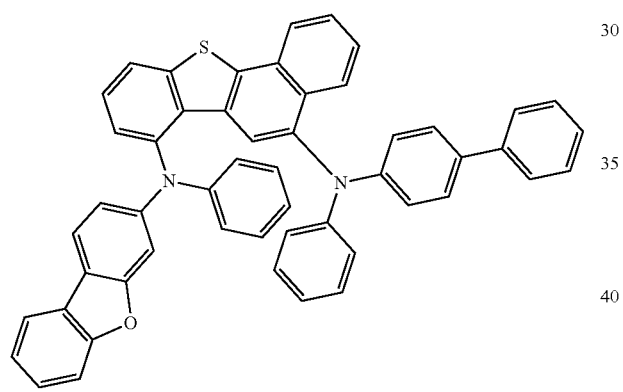
P-81
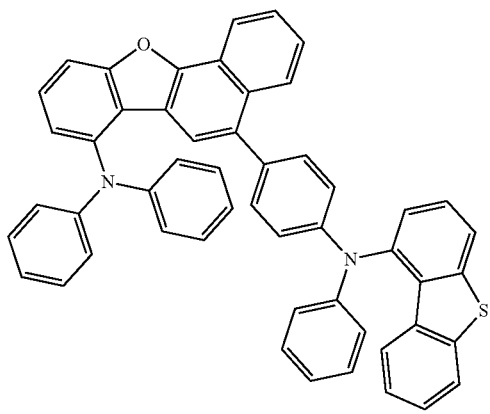
P-82
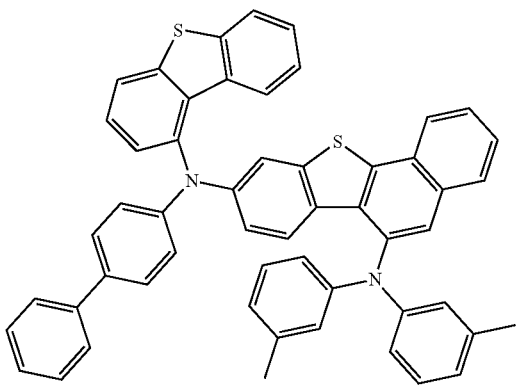
P-83
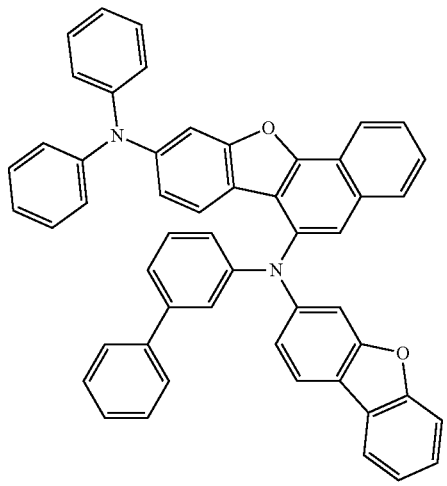
P-84
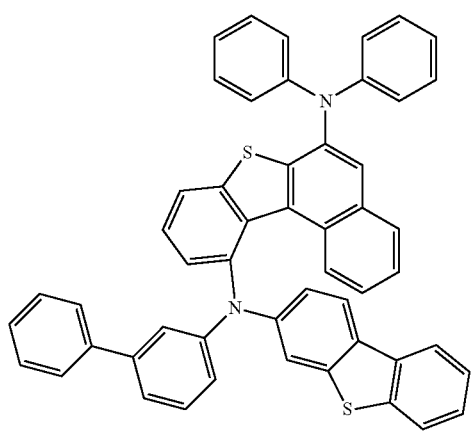

-continued

P-85
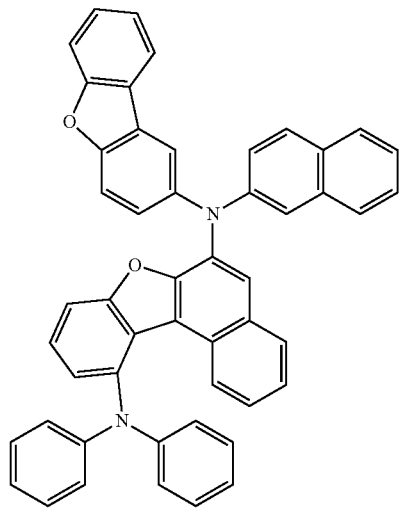

P-86
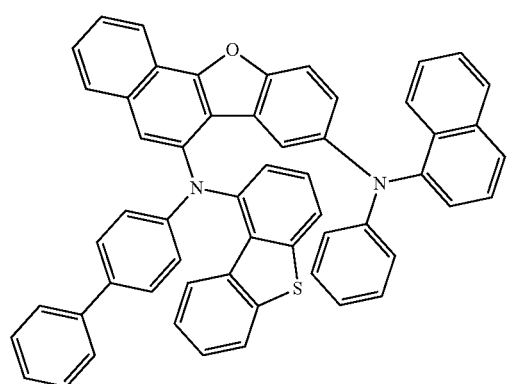

P-87
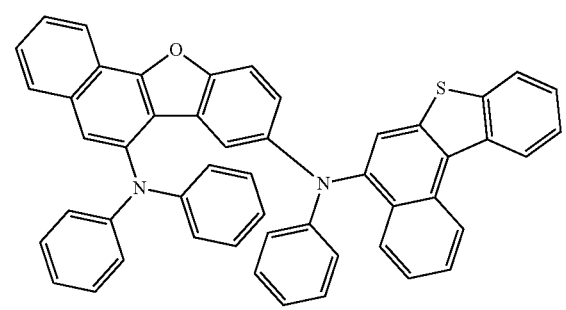

-continued

P-88
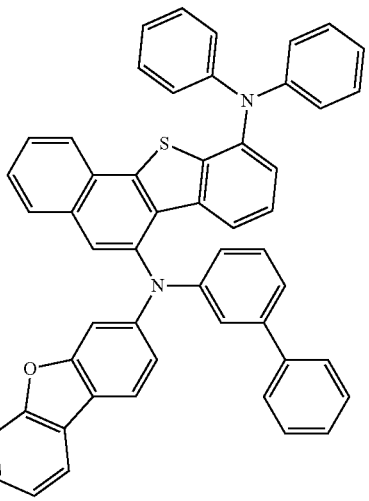

P-89
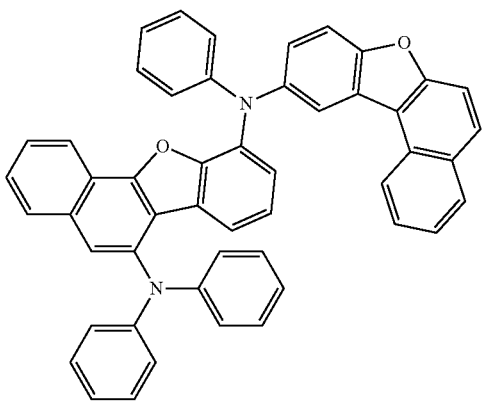

P-90
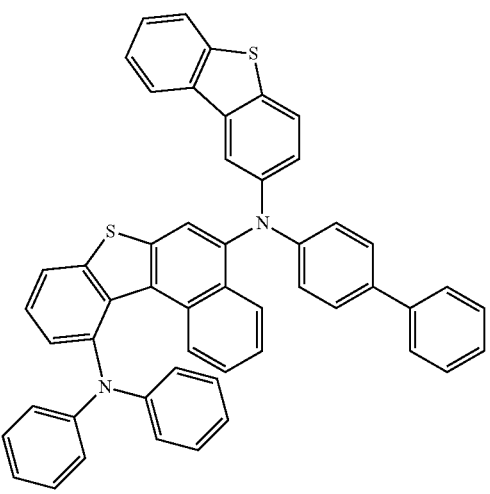

Referring to FIG. 1, the organic electric element (100) according to the present invention includes a first electrode (120) and a second electrode (180) formed on a substrate (110), and an organic material layer including the compound represented by Formula (1) between the first electrode (120) and the second electrode (180). Here, the first electrode (120) may be an anode (positive electrode), and the second electrode (180) may be a cathode (negative electrode). In the case of an inverted organic electric element, the first electrode may be a cathode, and the second electrode may be an anode.

The organic material layer may include a hole injection layer (130), a hole transport layer (140), an emitting layer (150), an electron transport layer (160), and an electron injection layer (170) formed in sequence on the first electrode (120). Here, the remaining layers except the emitting layer (150) may not be formed. The organic material layer may further include a hole blocking layer, an electron blocking layer, an emitting-auxiliary layer (151), an electron transport auxiliary layer, a buffer layer (141), etc., and the electron transport layer (160) and the like may serve as a hole blocking layer. Also, the emitting auxiliary layer (151) may be formed between the hole transport layer (140) and the emitting layer (150), and an electron transporting auxiliary layer may be formed between the emitting layer (150) and the electron transport layer (160).

Although not shown, the organic electric element according to the present invention may further include a protective layer formed on at least one side of the first and second electrodes, which is a side opposite to the organic material layer.

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (130), the hole transport layer (140), the emitting layer (150), the electron transport layer (160), and the electron injection layer (170) is formed thereon, and then depositing a material usable as a cathode thereon can manufacture an organic electroluminescent device according to an embodiment of the present invention.

In addition, an emission auxiliary layer (151) may be further formed between the hole transport layer (140) and the emitting layer (150), and an electron transport auxiliary layer may be further formed between the emitting layer (150) and the electron transport layer (160).

In addition, it is preferable that at least one hole transporting band layer is provided between the first electrode and the emitting layer, and the hole transporting layer may include a hole transport layer, an emitting auxiliary layer, or both, wherein the hole transport layer or the emitting auxiliary layer may provide an organic electronic element including the compound represented by Formula (1).

In another aspect, in one embodiment of the present invention, the present invention provides a first electrode; a second electrode; and an organic material layer disposed between the first electrode and the second electrode and including at least an emitting auxiliary layer and an emitting layer, wherein the organic material layer is selected from the group consisting of the hole injection layer, the hole transport layer, the emitting auxiliary layer and the emitting layer, wherein the organic material layer provides an organic electric element comprising one or two or more compounds represented by Formula (1).

The present invention may further include a light efficiency enhancing layer formed on at least one of the opposite side to the organic material layer among one side of the first electrode, or one of the opposite side to the organic material layer among one side of the second electrode.

Also, the present invention provides the organic electric element wherein the organic material layer is formed by one of a spin coating process, a nozzle printing process, an inkjet printing process, a slot coating process, a dip coating process or a roll-to-roll process, and since the organic material layer according to the present invention can be formed by various methods, the scope of the present invention is not limited by the method of forming the organic material layer.

The organic electric element according to an embodiment of the present invention may be a front emission type, a back emission type, or a both-sided emission type, depending on the material used.

WOLED (White Organic Light Emitting Device) has advantages of high resolution realization and excellent fairness, and can be manufactured using conventional LCD color filter technology. Various structures for a white organic light emitting device mainly used as a backlight device have been proposed and patented. Representatively, there are side-by-side arrangement of the radiation part of the R (red), G (green) and B (blue), a stacking method in which R, G, and B emitting layers are laminated on top and bottom, electroluminescence by the blue (B) organic emitting layer and, by using the light from this, a color conversion material (CCM) method using a photo-luminescence of an inorganic phosphor, etc., and the present invention may be applied to such WOLED.

The present invention also provides an electronic device comprising a display device including the organic electric element; and a control unit for driving the display device.

According to another aspect, the present invention provides an display device wherein the organic electric element is at least one of an OLED, an organic solar cell, an organic photo conductor, an organic transistor (organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis Examples of the compound represented by Formula (1) of the present invention and preparation examples of the organic electric element of the present invention will be described in detail by way of example, but are not limited to the following examples.

Synthesis Example 1

The final product represented by Formula (1) of the present invention can be synthesized by reaction between Sub 1 and Sub 2 as illustrated in the following Reaction Scheme 1, but is not limited thereto.

<Reaction Scheme 1>

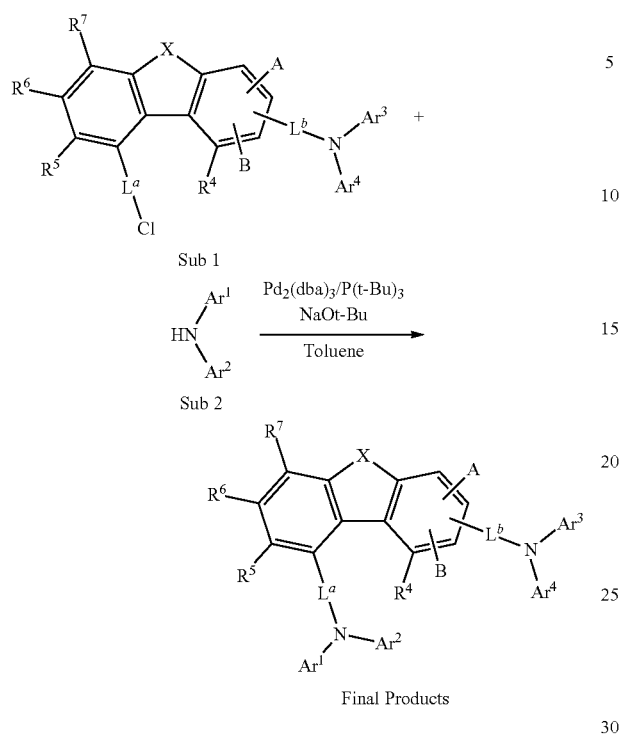

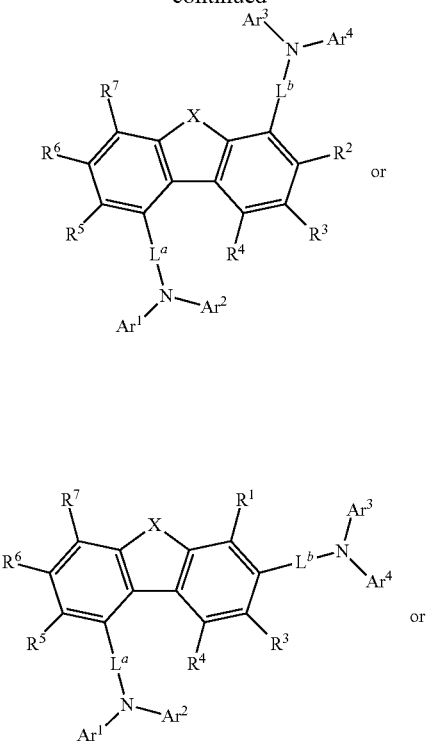

Sub 1

Sub 2

Final Products

X, Y, $Ar^1$, $Ar^2$, $Ar^3$, $Ar^4$, $L^a$, $L^b$, $R^1$, $R^2$, $R^3$, $R^4$, $R^5$, $R^6$, $R^7$ are the same as defined in Formula (1), and A, B, -$L^b$-$NAr^3Ar^4$ are each independently selected from among $R^1$, $R^2$ and $R^3$, and A, B, -$L^b$-$NAr^3Ar^4$ are different from each other.

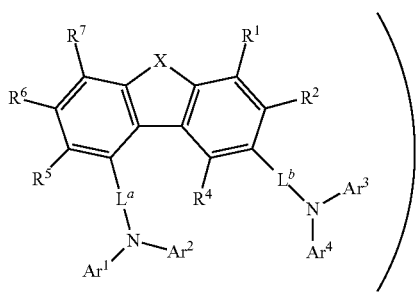

I. Synthesis of Sub 1

Sub 1 of reaction scheme 1 is synthesized by the reaction path of the following reaction scheme 2, but is not limited thereto.

<Reaction Scheme 2>

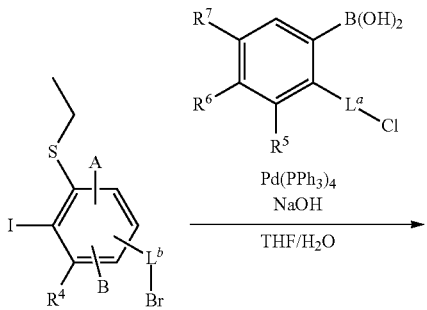

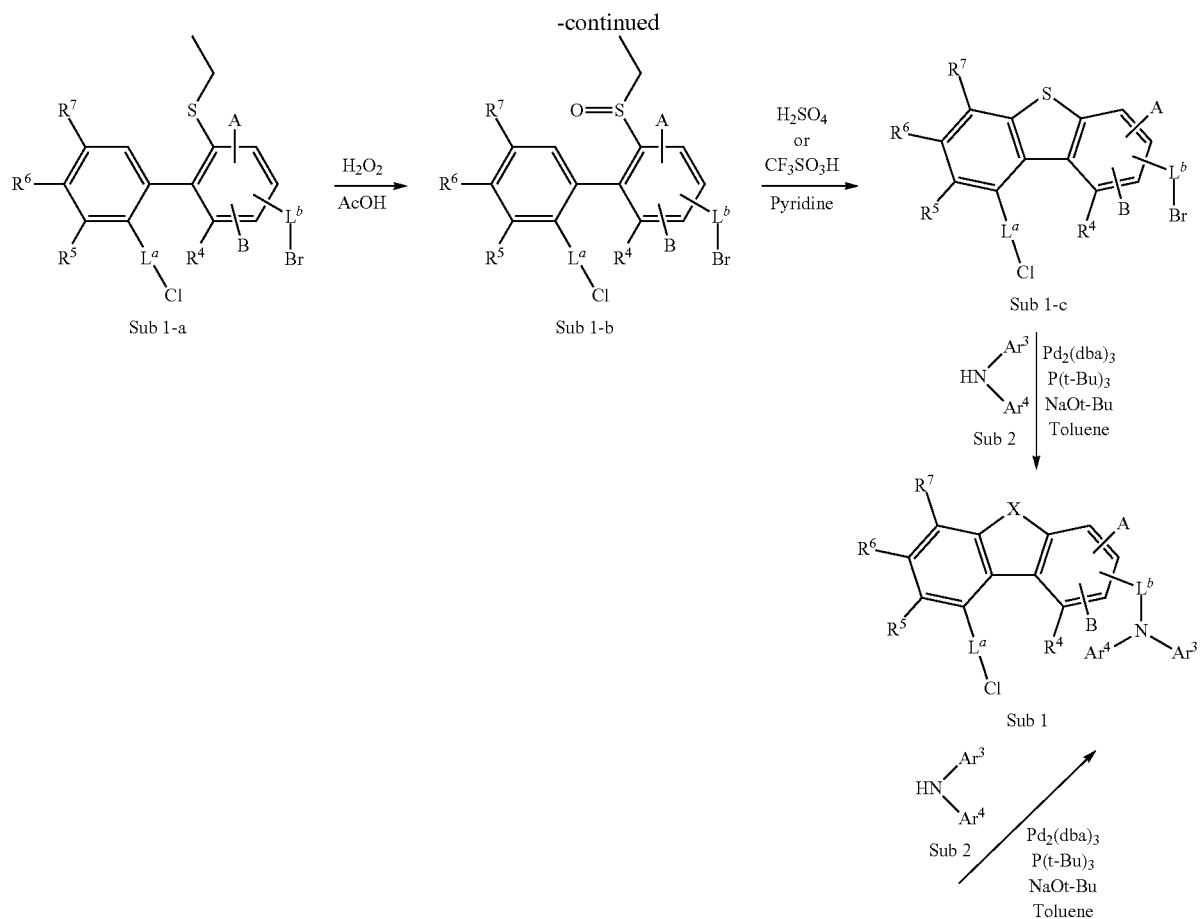
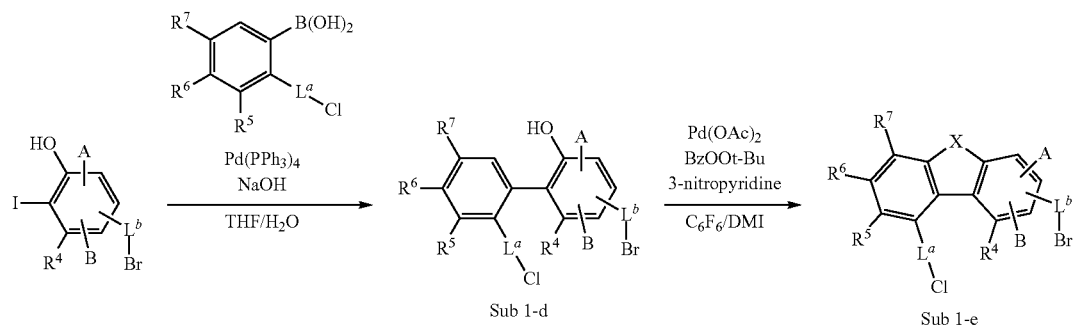
The synthesis examples of specific compounds belonging to Sub 1 are as follows.
1. Synthesis of Sub 1-7
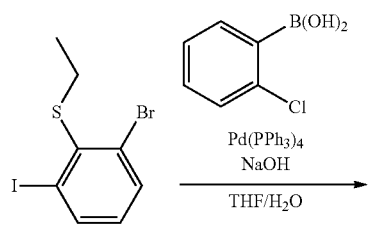
-continued
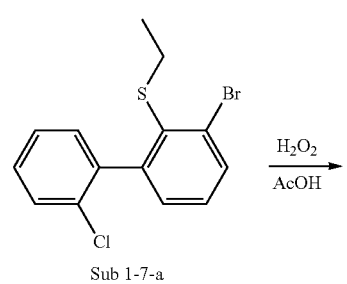

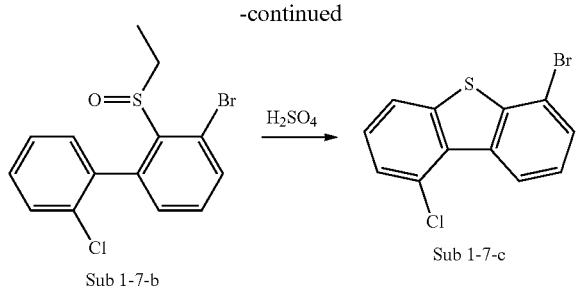

Sub 1-7-b

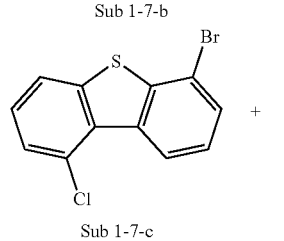

Sub 1-7-c

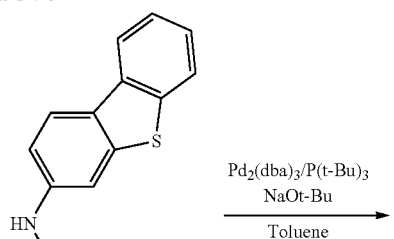

Sub 2-43

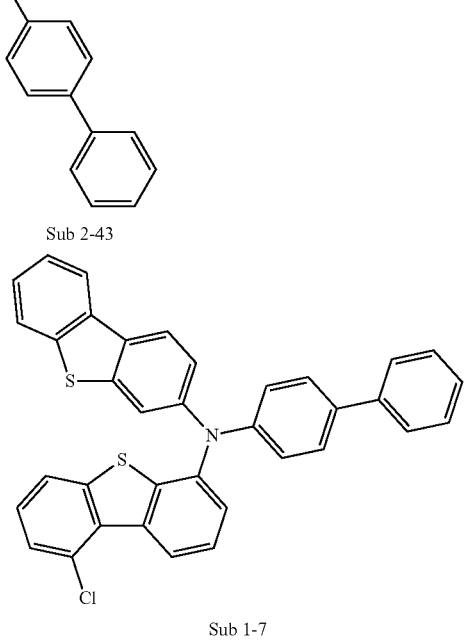

Sub 1-7

(1) Synthesis of Sub 1-7-a (2-bromo-6-iodophenyl)(ethyl)sulfane (33 g, 96.20 mmol), (2-chlorophenyl)boronic acid (15.04 g, 96.20 mmol), Pd(PPh$_3$)$_4$ (3.34 g, 2.89 mmol), NaOH (7.70 g, 192.41 mmol), THF (300 ml), H$_2$O (150 ml) were added and refluxed at 90° C. for 12 hours. When the reaction was completed, the temperature of the reaction was cooled to room temperature, extracted with MC (methylenechloride) and wiped with water. The organic layer was dried over MgSO$_4$ and concentrated. The resulting compound was separated by silicagel column chromatography to obtain the product. (28.05 g, 89%)

(2) Synthesis of Sub 1-7-b

Sub 1-7-a (14 g, 42.73 mmol), acetic acid (140 mL), 35% hydrogen peroxide (H$_2$O$_2$) (4.36 g) were added and stirred at room temperature. When the reaction was completed, the solvent was neutralized with aqueous NaOH solution, extracted with EA (ethylacetate) and wiped with water. The organic layer was dried over MgSO$_4$ and concentrated. The resulting compound was separated by silicagel column chromatography to obtain the product. (14.10 g, 96%)

(3) Synthesis of Sub 1-7-c

Sub 1-7-b (8.8 g, 25.61 mmol) and sulfuric acid (H$_2$SO$_4$) (50 mL) were added and stirred at room temperature. When the reaction was completed, the solvent was neutralized with aqueous NaOH solution, extracted with MC and wiped with water. The organic layer was dried over MgSO$_4$ and concentrated. The resulting compound was separated by silicagel column chromatography to obtain the product. (5.64 g, 74%)

(4) Synthesis of Sub 1-7

Sub 1-7-c (9.10 g, 30.58 mmol), Sub 2-43 (10.75 g, 30.58 mmol), Pd$_2$(dba)$_3$ (0.84 g, 0.92 mmol), NaOt-Bu (5.88 g, 61.16 mmol), P(t-bu)$_3$ (0.62 g, 3.06 mmol), toluene (100 ml) were added and refluxed at 80° C. for 4 hours. When the reaction was completed, the temperature of the reaction was cooled to room temperature, extracted with MC and wiped with water. The organic layer was dried over MgSO$_4$ and concentrated. The resulting compound was separated by silicagel column chromatography to obtain the product. (15.98 g, 92%)

2. Synthesis of Sub 1-18

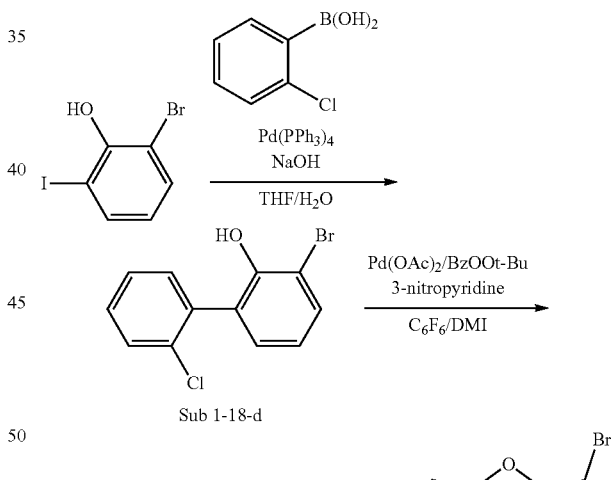

Sub 1-18-d

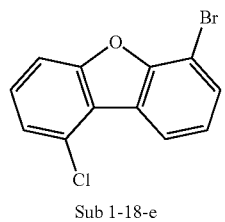

Sub 1-18-e

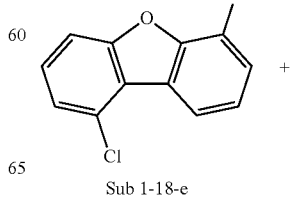

Sub 1-18-e

-continued

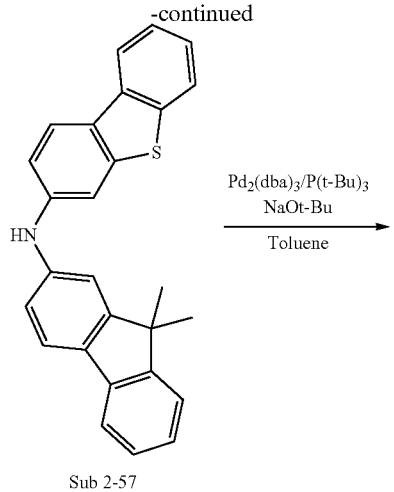
Sub 2-57

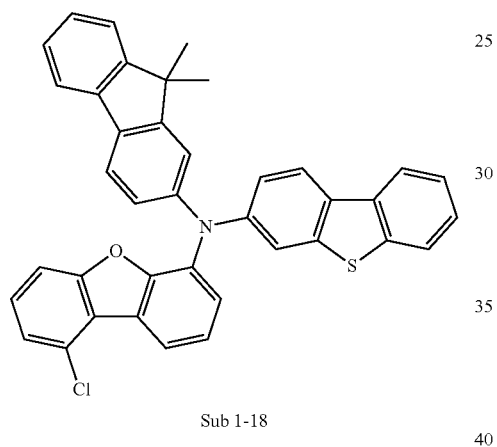
Sub 1-18

(1) Synthesis of Sub 1-18-d 2-bromo-6-iodophenol (19.5 g, 65.24 mmol), (2-chlorophenyl)boronic acid (10.20 g, 65.24 mmol), Pd(PPh$_3$)$_4$ (2.26 g, 1.96 mmol), NaOH (5.22 g, 130.47 mmol), THF (200 ml), H$_2$O (100 ml) were carried out in the same manner as in Sub 1-7-a to give the product (13.32 g, 72%).

(2) Synthesis of Sub 1-18-e

Sub 1-18-d (12.2 g, 43.03 mmol), Pd(OAc)$_2$ (0.48 g, 2.15 mmol), 3-nitropyridine (0.27 g, 2.15 mmol), BzOOtBu (tert-butyl peroxybenzoate) (16.71 g, 86.05 mmol), C$_6$F$_6$ (hexafluorobenzene) (100 ml), DMI (N,N'-dimethylimidazolidinone) (70 ml) were added and refluxed at 90° C. for 3 hours. When the reaction was completed, the temperature of the reaction was cooled to room temperature, extracted with EA and wiped with water. The organic layer was dried over MgSO$_4$ and concentrated. The resulting compound was separated by silicagel column chromatography to obtain the product. (6.66 g, 55%)

(3) Synthesis of Sub 1-18

Sub 1-18-e (6.10 g, 21.67 mmol), Sub 2-57 (8.48 g, 21.67 mmol), Pd$_2$(dba)$_3$ (0.60 g, 0.65 mmol), NaOt-Bu (4.16 g, 43.33 mmol), P(t-bu)$_3$ (0.44 g, 2.17 mmol), toluene (80 ml) were carried out in the same manner as in Sub 1-7 to give the product (11.42 g, 89%).

3. Synthesis of Sub 1-23

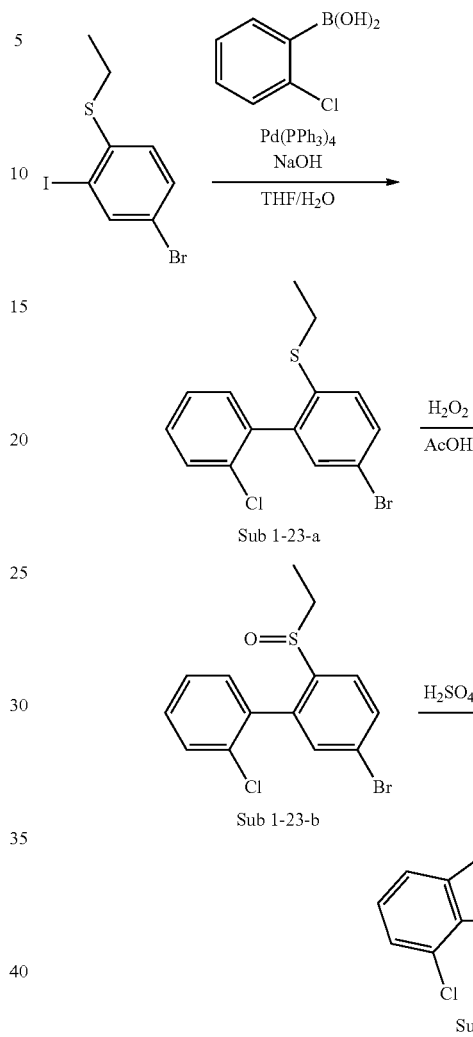

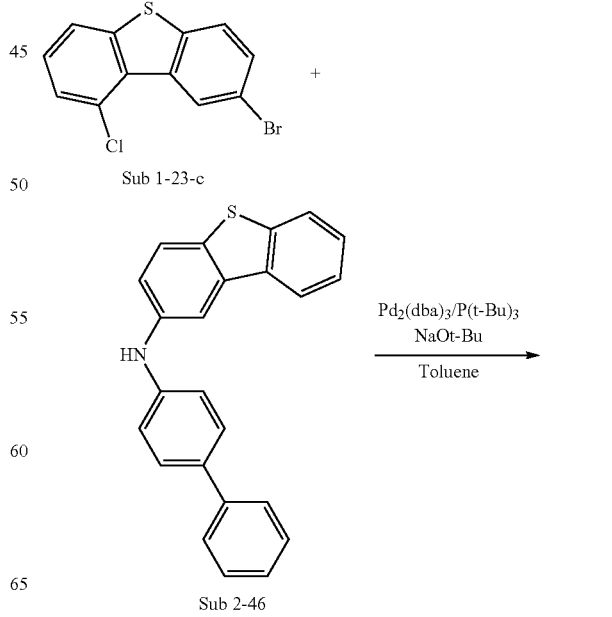
Sub 2-46

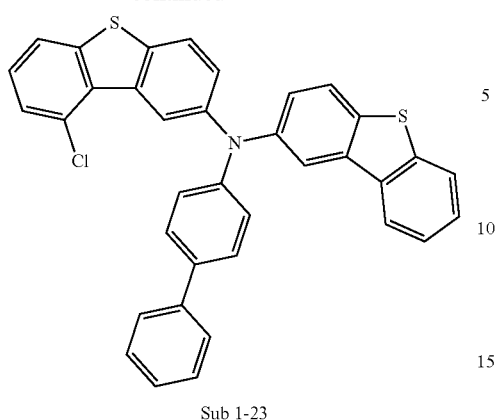

Sub 1-23

(1) Synthesis of Sub 1-23-a (4-bromo-2-iodophenyl)(ethyl)sulfane (15.70 g, 45.77 mmol), (2-chlorophenyl)boronic acid (7.16 g, 45.77 mmol), Pd(PPh$_3$)$_4$ (1.59 g, 1.37 mmol), NaOH (3.66 g, 91.54 mmol), THF (200 ml), H$_2$O (100 ml) were carried out in the same manner as in Sub 1-7-a to give the product (12.60 g, 84%).

(2) Synthesis of Sub 1-23-b

Sub 1-23-a (11.60 g, 35.40 mmol), acetic acid (150 mL), 35% hydrogen peroxide (H$_2$O) (3.61 g) were carried out in the same manner as in Sub 1-7-b to give the product (11.68 g, 96%).

(3) Synthesis of Sub 1-23-c

Sub 1-23-b (8.70 g, 25.31 mmol), sulfuric acid (H$_2$SO$_4$) (50 mL) were carried out in the same manner as in Sub 1-7-c to give the product (6.78 g, 90%).

(4) Synthesis of Sub 1-23

Sub 1-23-c (6.00 g, 20.16 mmol), Sub 2-46 (7.09 g, 20.16 mmol), Pd$_2$(dba)$_3$ (0.55 g, 0.60 mmol), NaOt-Bu (3.88 g, 40.32 mmol), P(t-bu)$_3$ (0.41 g, 2.02 mmol), toluene (80 ml) were carried out in the same manner as in Sub 1-7 to give the product (9.97 g, 87%).

4. Synthesis of Sub 1-52

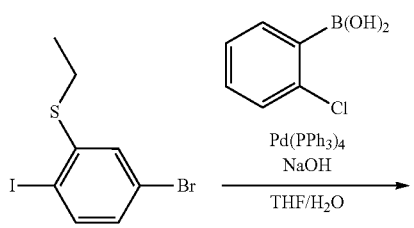

Sub 1-52-a

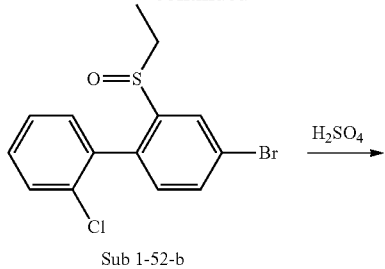

Sub 1-52-b

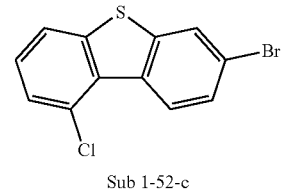

Sub 1-52-c

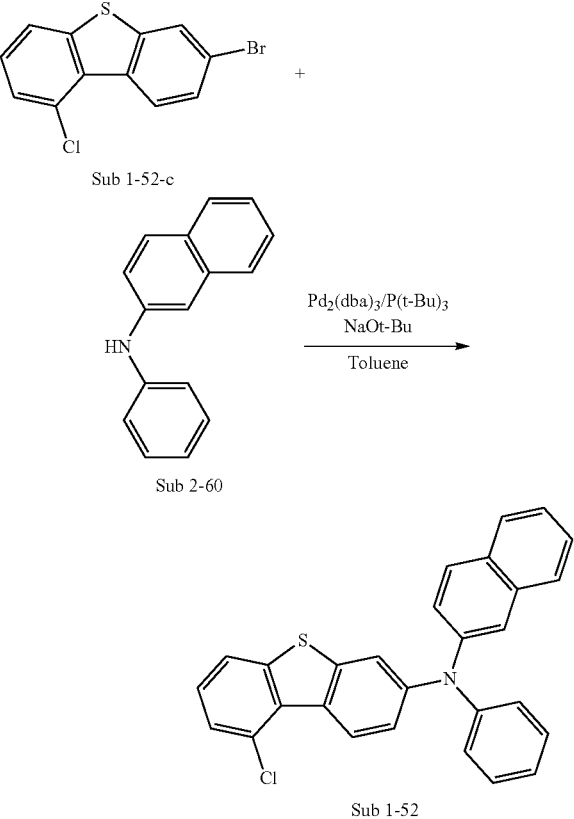

Sub 1-52

(1) Synthesis of Sub 1-52-a (5-bromo-2-iodophenyl)(ethyl)sulfane (22.00 g, 64.14 mmol), (2-chlorophenyl)boronic acid (10.03 g, 64.14 mmol), Pd(PPh$_3$)$_4$ (2.22 g, 1.92 mmol), NaOH (5.13 g, 128.27 mmol), THF (300 ml), H$_2$O (150 ml) were carried out in the same manner as in Sub 1-7-a to give the product (17.44 g, 83%).

(2) Synthesis of Sub 1-52-b

Sub 1-52-a (15.30 g, 46.69 mmol), acetic acid (150 mL), 35% hydrogen peroxide (H$_2$O) (4.76 g) were carried out in the same manner as in Sub 1-7-b to give the product (15.57 g, 97%).

(3) Synthesis of Sub 1-52-c

Sub 1-52-b (10.8 g, 31.43 mmol) and sulfuric acid (H$_2$SO$_4$) (50 mL) were carried out in the same manner as in Sub 1-7-c to give the product (8.88 g, 95%).

(4) Synthesis of Sub 1-52

Sub 1-52-c (7.20 g, 24.19 mmol), Sub 2-60 (5.31 g, 24.19 mmol), Pd$_2$(dba)$_3$ (0.66 g, 0.73 mmol), NaOt-Bu (4.65 g, 48.39 mmol), P(t-bu)$_3$ (0.49 g, 2.42 mmol), toluene (90 ml) were carried out in the same manner as in Sub 1-7 to give the product (9.28 g, 88%).

5. Synthesis of Sub 1-58

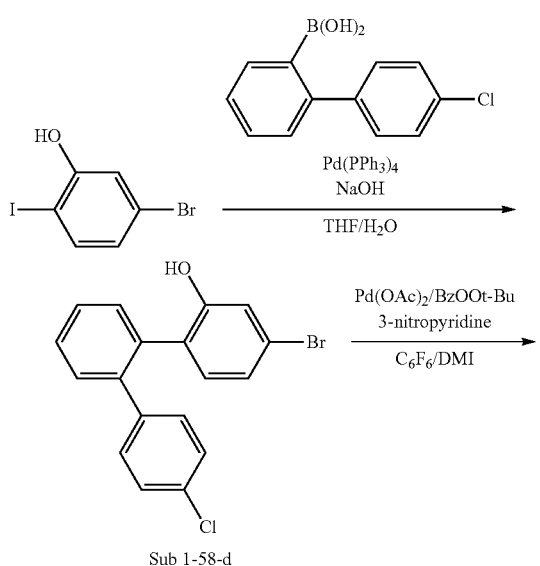
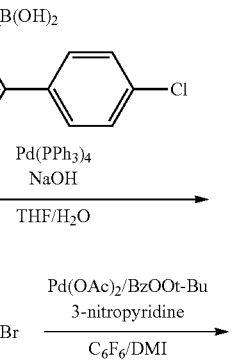
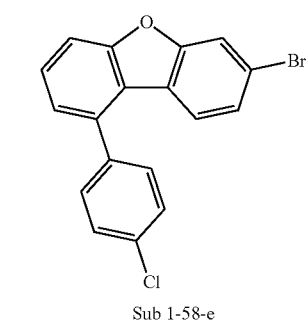
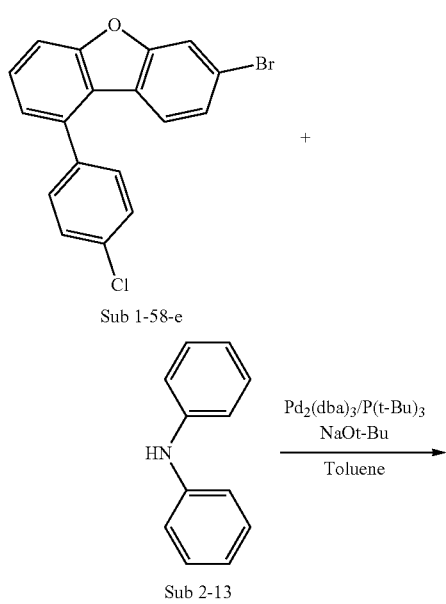
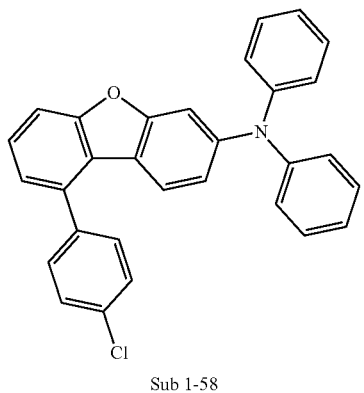 [SMILES: Clc1ccc(-c2cccc3oc4cc(N(c5ccccc5)c5ccccc5)ccc4c23)cc1]

Sub 1-58

(1) Synthesis of Sub 1-58-d 5-bromo-2-iodophenol (13.0 g, 43.49 mmol), (4'-chloro-[1,1'-biphenyl]-2-yl)boronic acid (10.11 g, 43.49 mmol), Pd(PPh$_3$)$_4$ (1.51 g, 1.30 mmol), NaOH (3.48 g, 86.98 mmol), THF (150 ml), H$_2$O (80 ml) were carried out in the same manner as in Sub 1-7-a to give the product (10.79 g, 69%).

(2) Synthesis of Sub 1-58-e

Sub 1-58-d (8.60 g, 23.91 mmol)°]]Pd(OAc)$_2$ (0.27 g, 1.20 mmol), 3-nitropyridine (0.15 g, 1.20 mmol), BzOOtBu (tert-butyl peroxybenzoate) (9.29 g, 47.82 mmol), C$_6$F$_6$ (hexafluorobenzene) (100 ml), DMI (N,N'-dimethylimidazolidinone) (70 ml) were carried out in the same manner as in Sub 1-18-e to give the product (4.19 g, 72%).

(3) Synthesis of Sub 1-58

Sub 1-58-e (3.90 g, 10.91 mmol), Sub 2-13 (2.94 g, 10.91 mmol), Pd$_2$(dba)$_3$ (0.30 g, 0.33 mmol), NaOt-Bu (2.10 g, 21.81 mmol), P(t-bu)$_3$ (0.22 g, 1.09 mmol), toluene (50 ml) were carried out in the same manner as in Sub 1-7 to give the product (4.18 g, 86%).

6. Synthesis of Sub 1-73

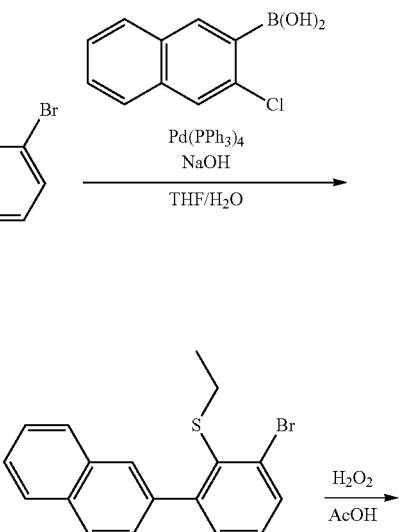

Sub 1-73-a

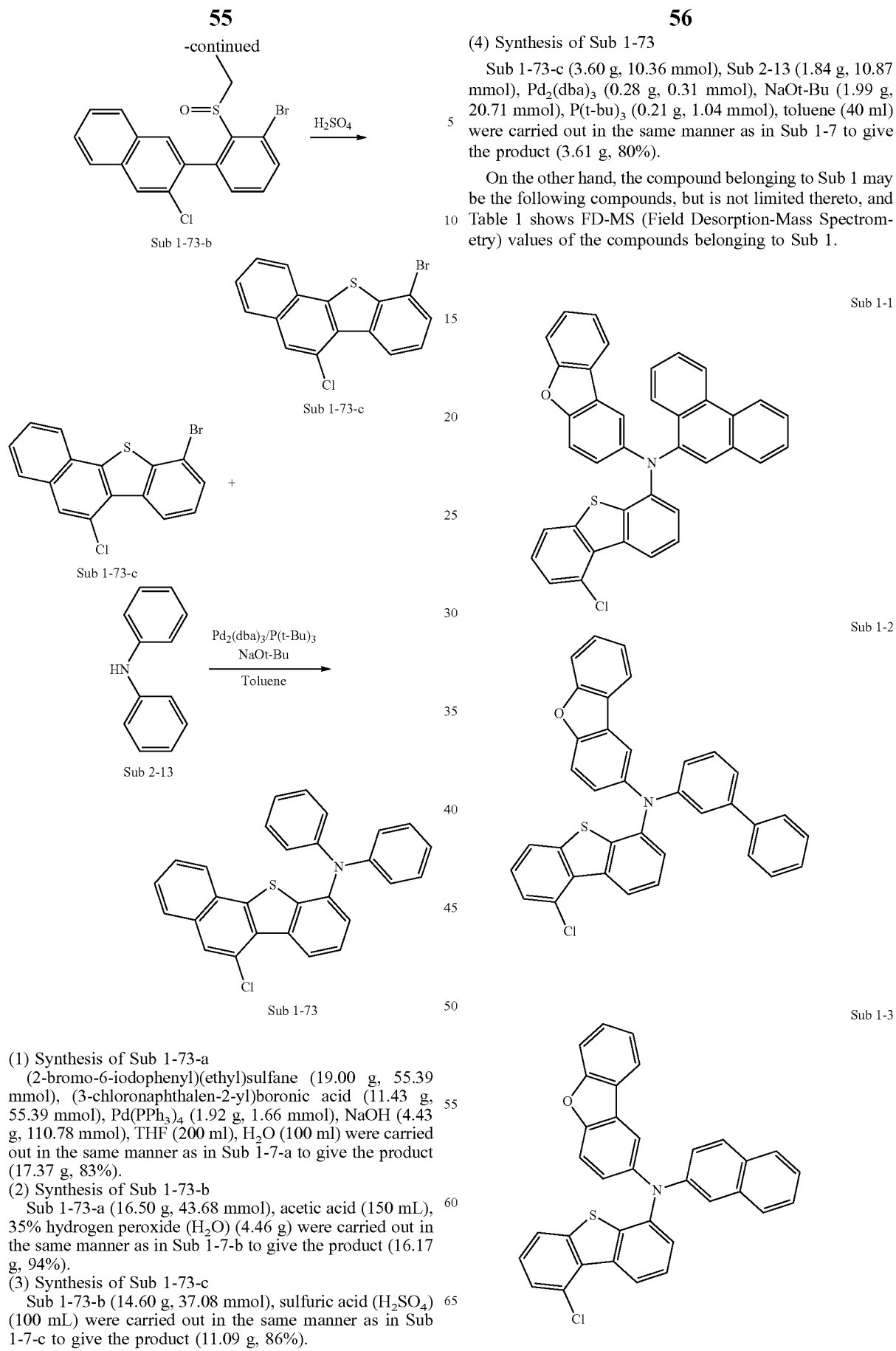

(4) Synthesis of Sub 1-73

Sub 1-73-c (3.60 g, 10.36 mmol), Sub 2-13 (1.84 g, 10.87 mmol), Pd$_2$(dba)$_3$ (0.28 g, 0.31 mmol), NaOt-Bu (1.99 g, 20.71 mmol), P(t-bu)$_3$ (0.21 g, 1.04 mmol), toluene (40 ml) were carried out in the same manner as in Sub 1-7 to give the product (3.61 g, 80%).

On the other hand, the compound belonging to Sub 1 may be the following compounds, but is not limited thereto, and Table 1 shows FD-MS (Field Desorption-Mass Spectrometry) values of the compounds belonging to Sub 1.

(1) Synthesis of Sub 1-73-a (2-bromo-6-iodophenyl)(ethyl)sulfane (19.00 g, 55.39 mmol), (3-chloronaphthalen-2-yl)boronic acid (11.43 g, 55.39 mmol), Pd(PPh$_3$)$_4$ (1.92 g, 1.66 mmol), NaOH (4.43 g, 110.78 mmol), THF (200 ml), H$_2$O (100 ml) were carried out in the same manner as in Sub 1-7-a to give the product (17.37 g, 83%).

(2) Synthesis of Sub 1-73-b

Sub 1-73-a (16.50 g, 43.68 mmol), acetic acid (150 mL), 35% hydrogen peroxide (H$_2$O) (4.46 g) were carried out in the same manner as in Sub 1-7-b to give the product (16.17 g, 94%).

(3) Synthesis of Sub 1-73-c

Sub 1-73-b (14.60 g, 37.08 mmol), sulfuric acid (H$_2$SO$_4$) (100 mL) were carried out in the same manner as in Sub 1-7-c to give the product (11.09 g, 86%).

Sub 1-4
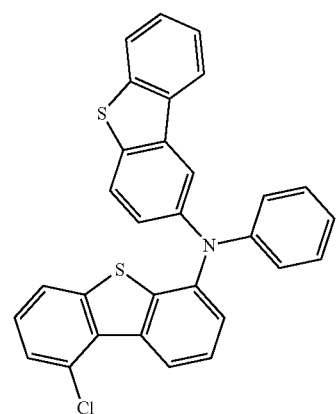
Sub 1-5
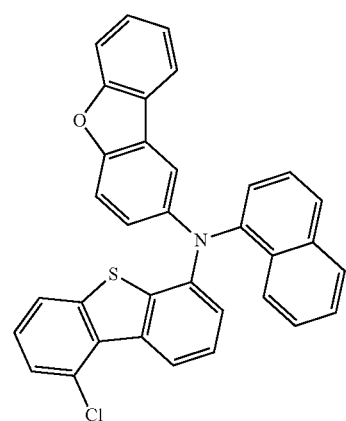
Sub 1-6
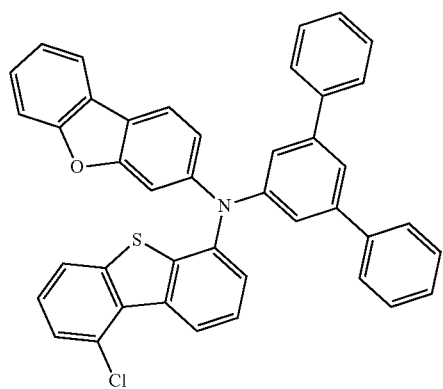
Sub 1-7
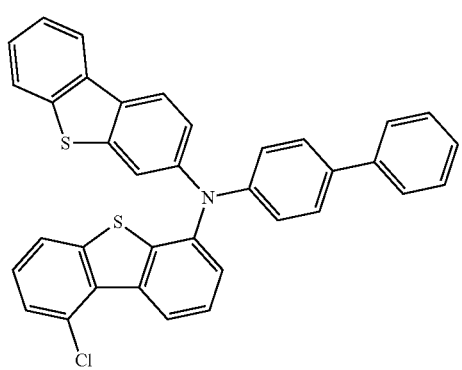
Sub 1-8
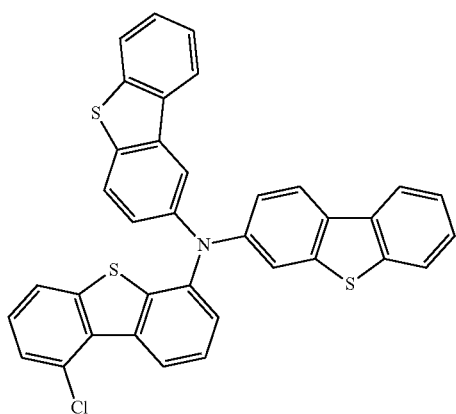
Sub 1-9
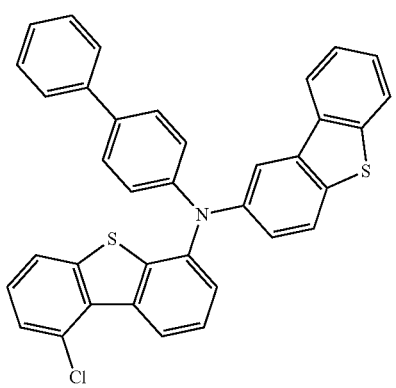
Sub 1-10
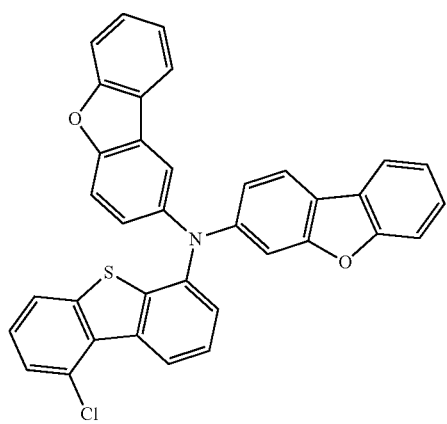
Sub 1-11
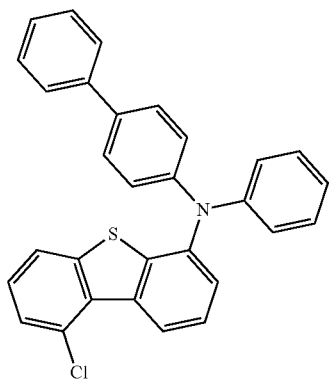

Sub 1-12
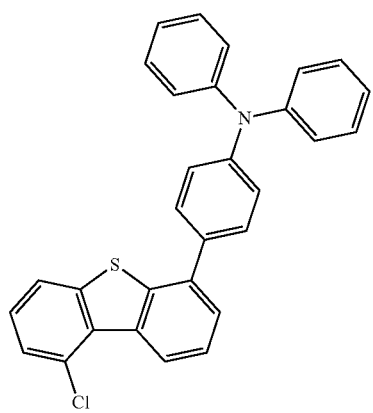
Sub 1-16
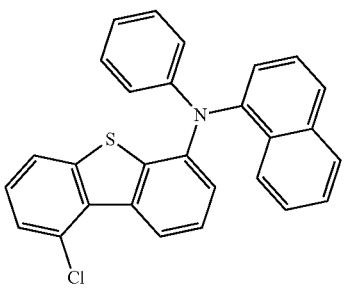
Sub 1-13
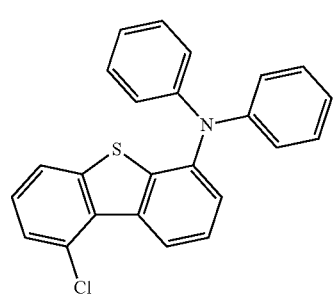
Sub 1-17
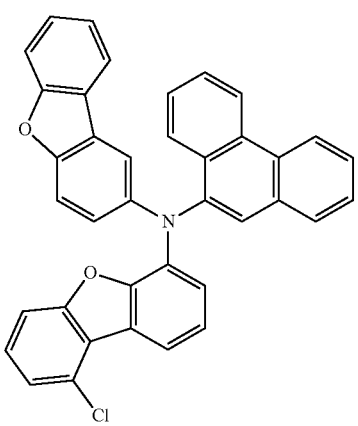
Sub 1-14
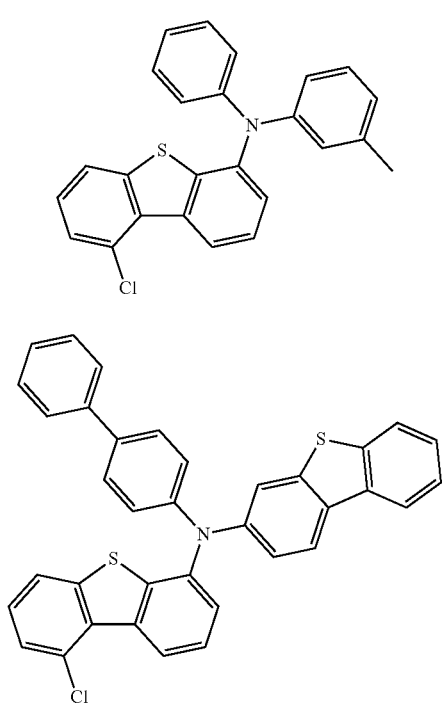
Sub 1-18
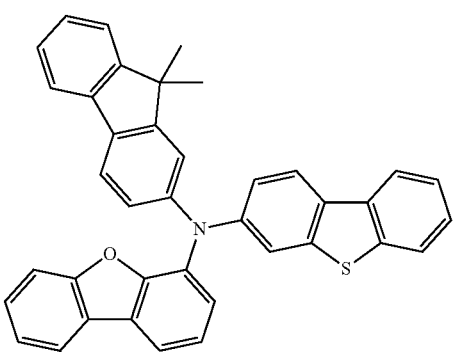
Sub 1-15
Sub 1-19
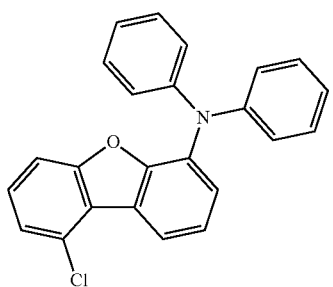

Sub 1-20
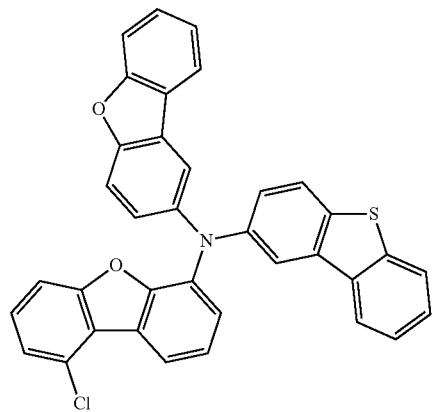
Sub 1-21
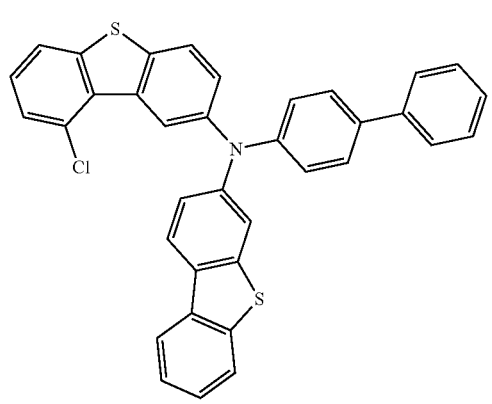
Sub 1-22
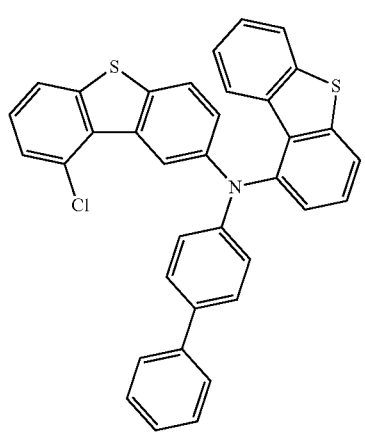
Sub 1-23
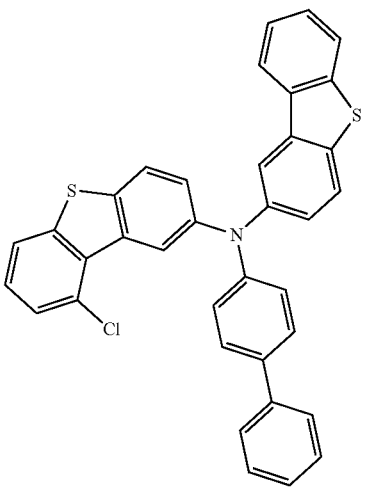
Sub 1-24
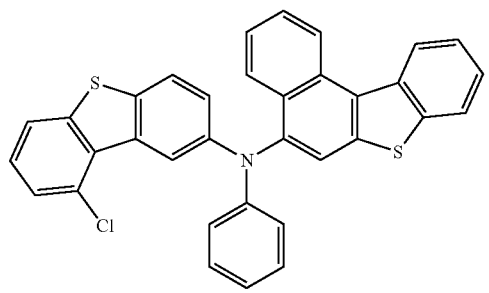
Sub 1-25
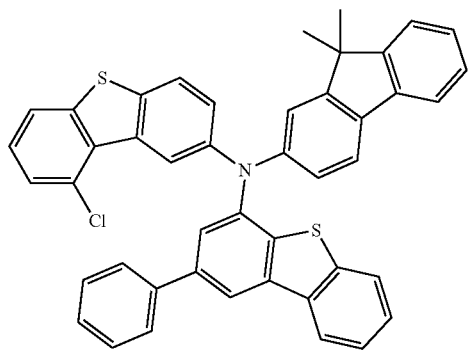
Sub 1-26
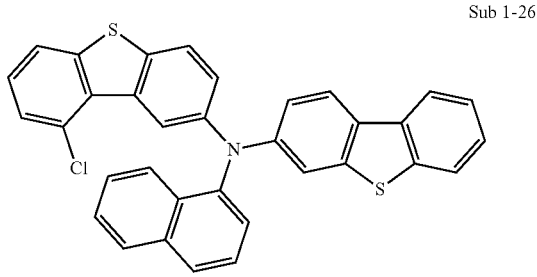

Sub 1-27
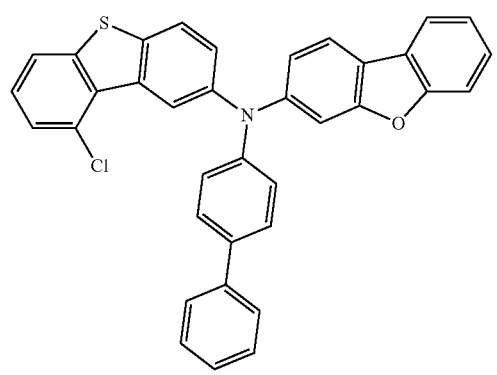
Sub 1-28
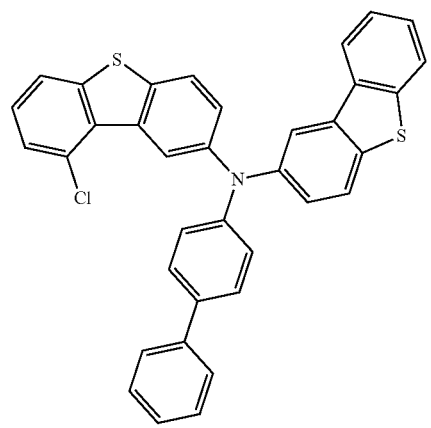
Sub 1-29
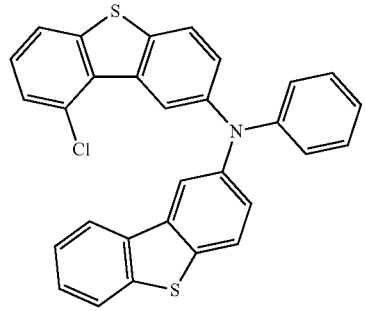
Sub 1-30
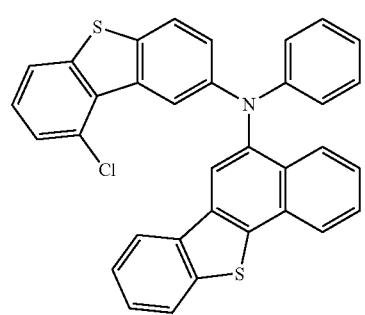
Sub 1-31
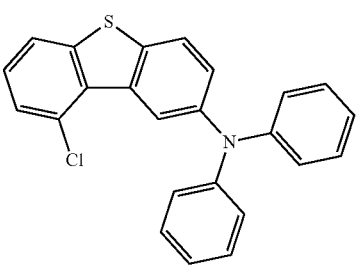
Sub 1-32
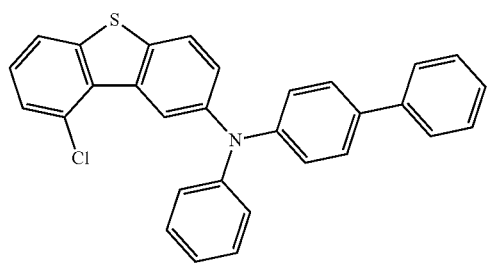
Sub 1-33
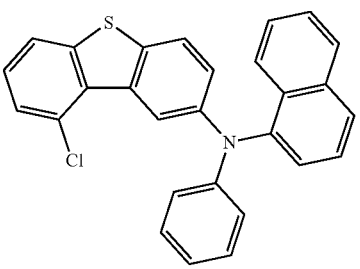
Sub 1-34
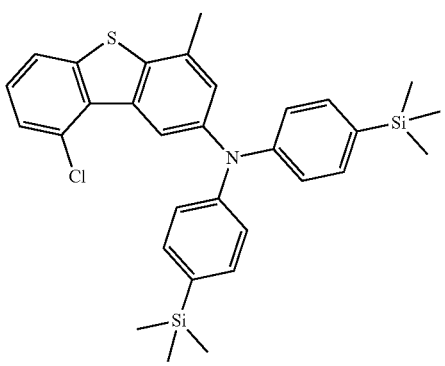
Sub 1-35
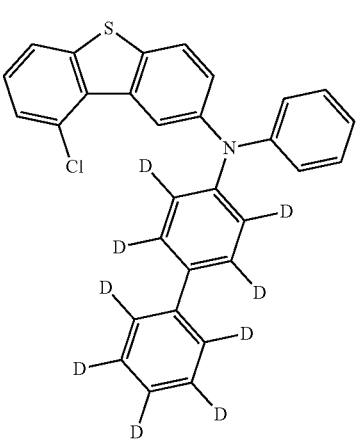

65
-continued
Sub 1-36
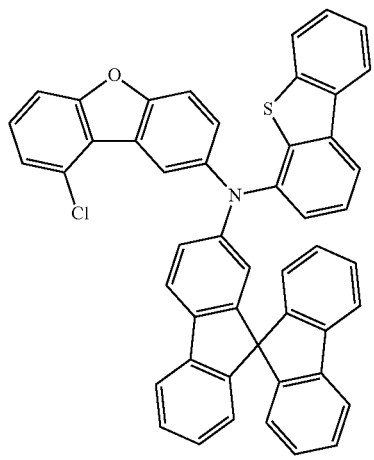
Sub 1-37
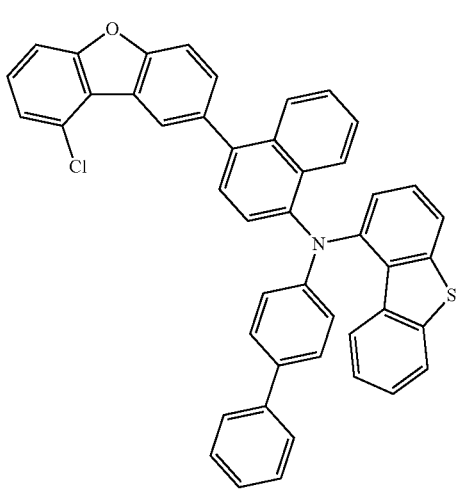
Sub 1-38
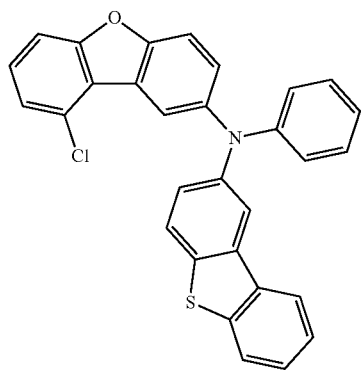
Sub 1-39
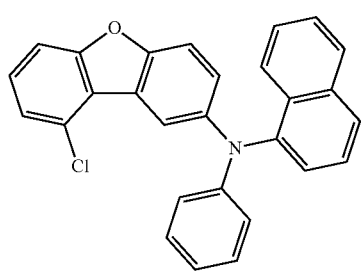
66
-continued
Sub 1-40
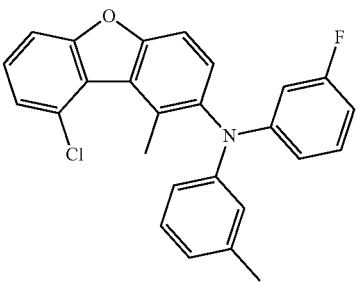
Sub 1-41
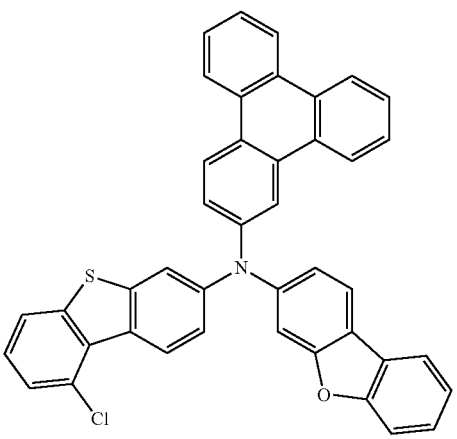
Sub 1-42
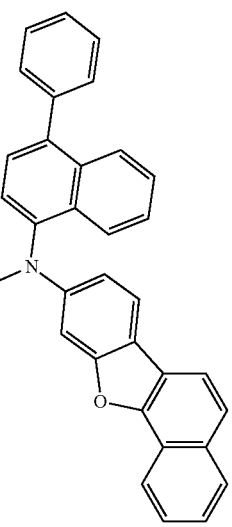
Sub 1-43
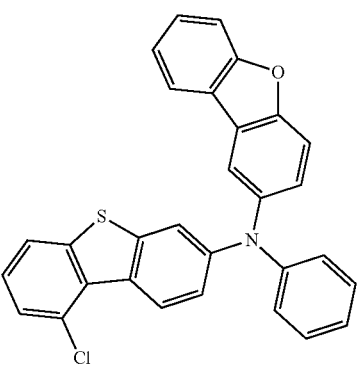

-continued
Sub 1-44
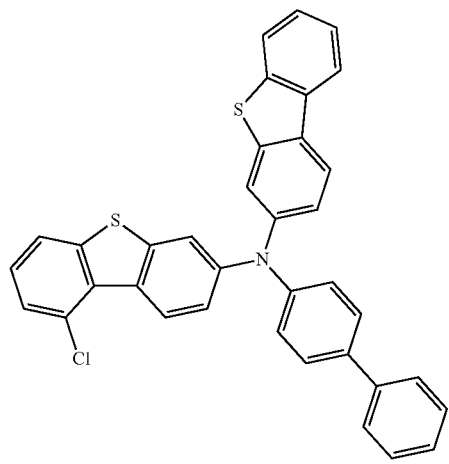
Sub 1-45
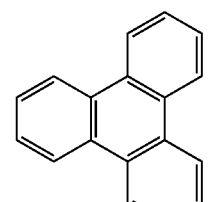
Sub 1-46
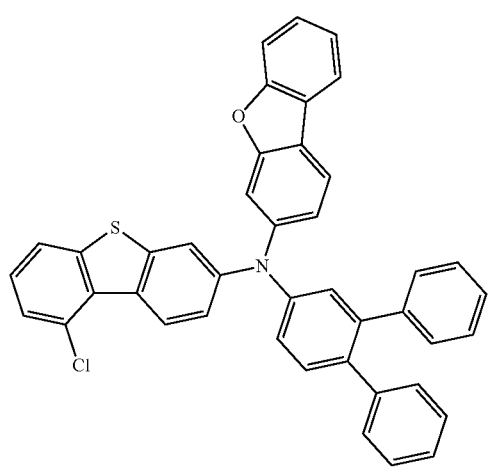
-continued
Sub 1-47
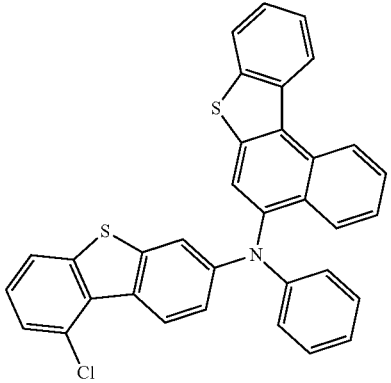
Sub 1-48
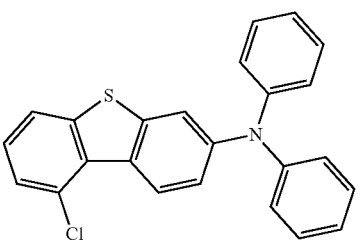
Sub 1-49
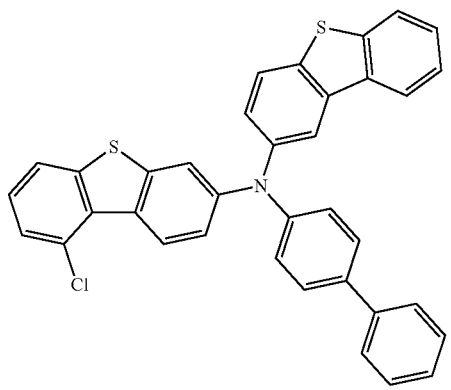
Sub 1-50
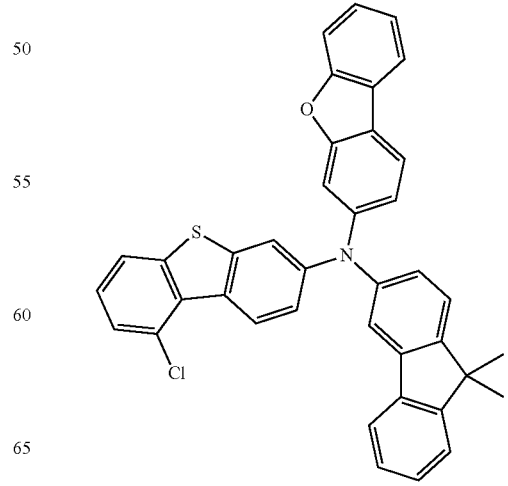

-continued
Sub 1-51
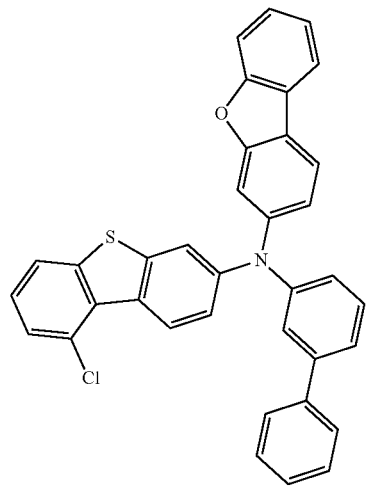
Sub 1-52
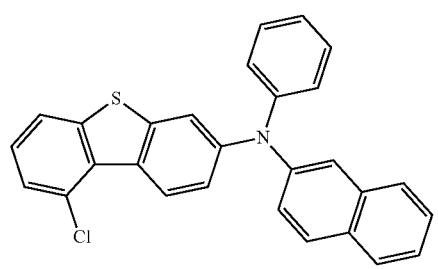
Sub 1-53
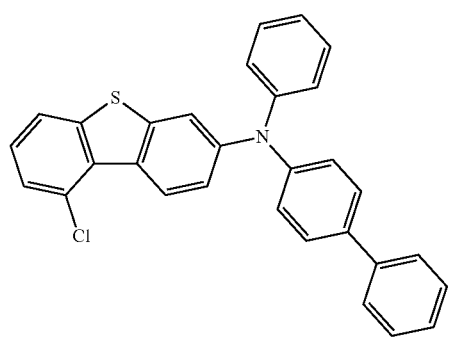
Sub 1-54
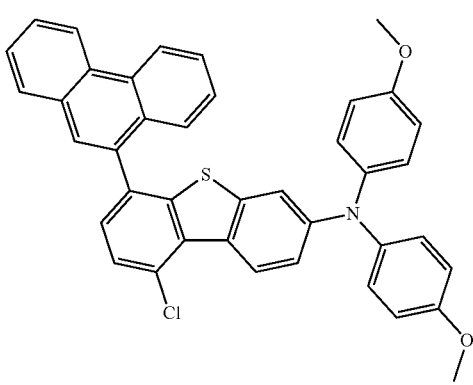
-continued
Sub 1-55
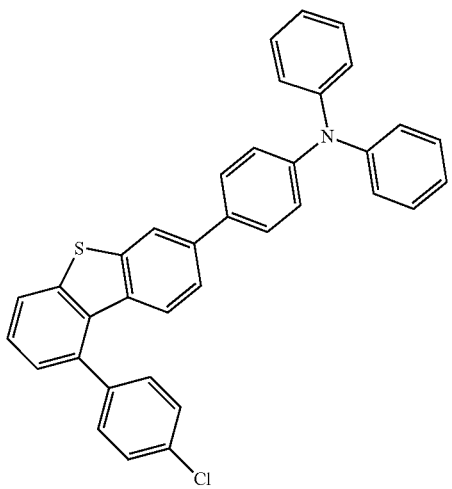
Sub 1-56
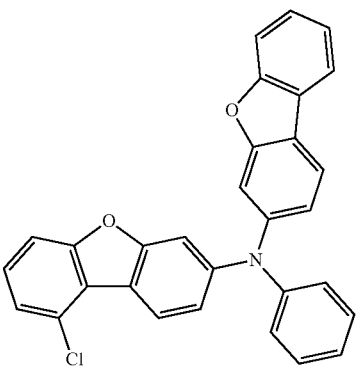
Sub 1-57
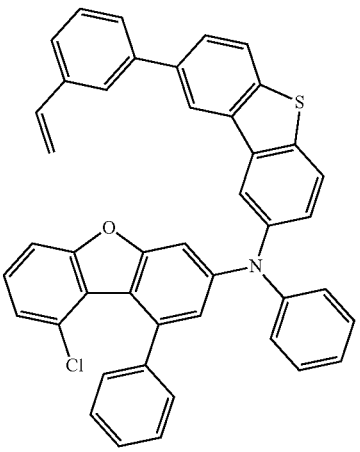

Sub 1-58
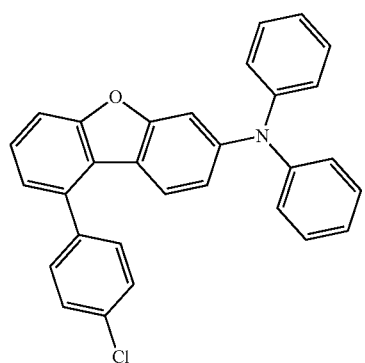
Sub 1-59
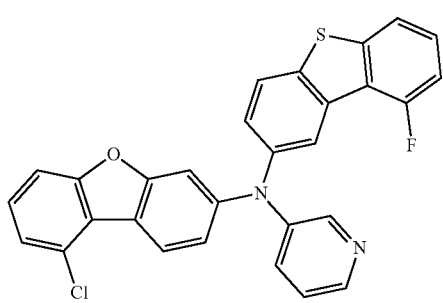
Sub 1-60
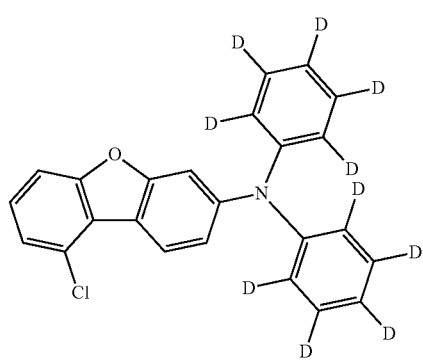
Sub 1-61
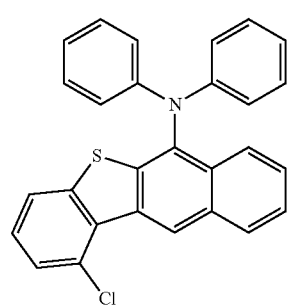
Sub 1-62
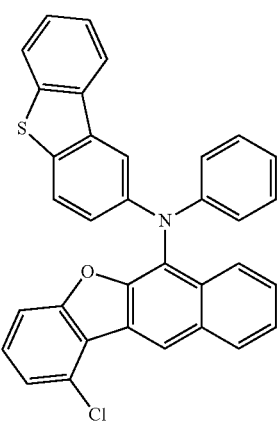
Sub 1-63
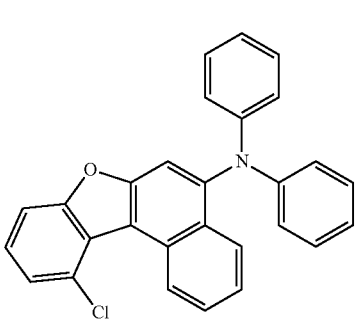
Sub 1-64
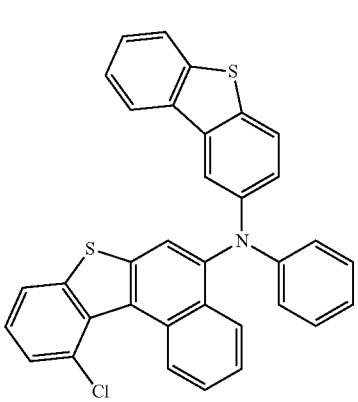
Sub 1-65
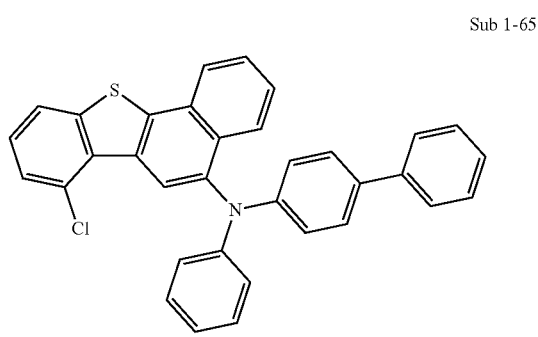

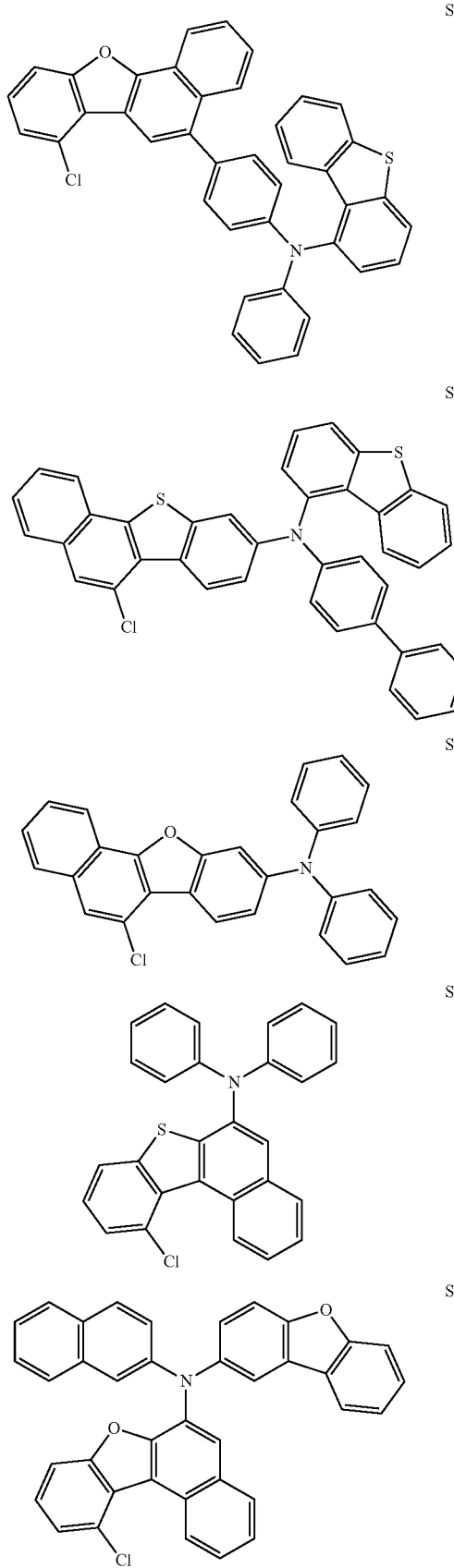
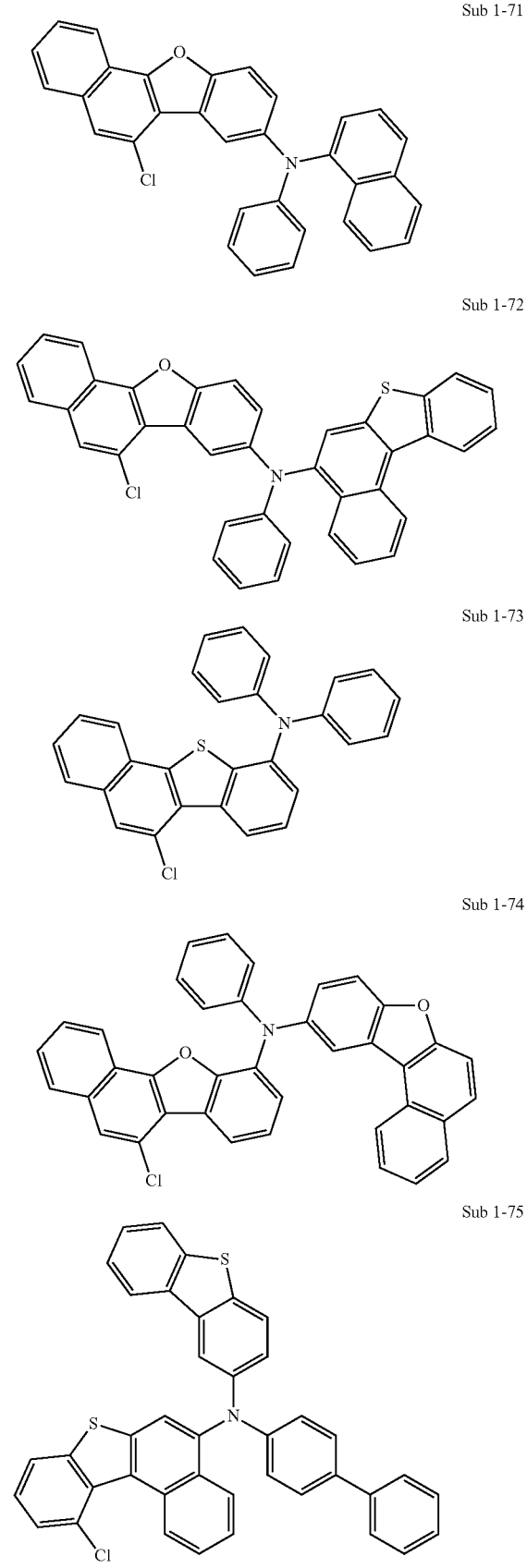

TABLE 1

| compound | FD-MS | compound | FD-MS |
|---|---|---|---|
| Sub 1-7 | m/z = 567.09 ($C_{36}H_{22}ClNOS_2$ = 568.15) | Sub 1-8 | m/z = 597.04 ($C_{36}H_{20}ClNOS_3$ = 598.19) |
| Sub 1-16 | m/z = 435.08 ($C_{28}H_{18}ClNS$ = 435.97) | Sub 1-18 | m/z = 591.14 ($C_{39}H_{26}ClNOS$ = 592.15) |
| Sub 1-23 | m/z = 567.09 ($C_{36}H_{22}ClNOS_2$ = 568.15) | Sub 1-24 | m/z = 541.07 ($C_{34}H_{20}ClNS_2$ = 542.11) |
| Sub 1-44 | m/z = 567.09 ($C_{36}H_{22}ClNS_2$ = 568.15) | Sub 1-52 | m/z = 435.08 ($C_{28}H_{18}ClNS$ = 435.97) |
| Sub 1-58 | m/z = 445.12 ($C_{30}H_{20}ClNO$ = 445.95) | Sub 1-64 | m/z = 541.07 ($C_{34}H_{20}ClNS_2$ = 542.11) |

II. Synthesis of Sub 2

Sub 2 of Reaction Scheme 1 can be synthesized by the reaction path of the following Reaction Scheme 3 (Korean Patent No. 10-1251451 (Registered on Apr. 5, 2013) of the present applicant), but is not limited thereto.

$Z^1$ is $Ar^1$ or $Ar^3$, and $Z^2$ is $Ar^2$ or $Ar^4$.

<Reaction Scheme 3>

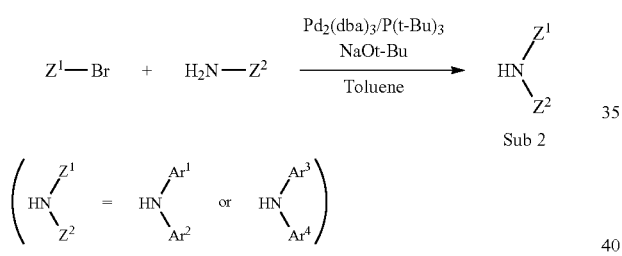

On the other hand, the compound belonging to Sub 2 may be the following compounds, but is not limited thereto, and Table 2 shows FD-MS (Field Desorption-Mass Spectrometry) values of the compounds belonging to Sub 2.

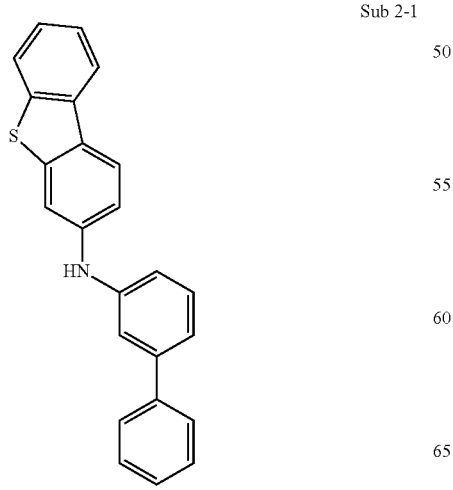

Sub 2-1

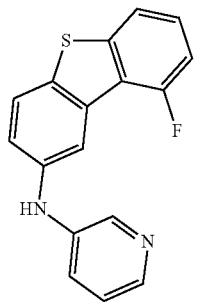

Sub 2-2

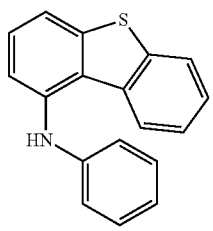

Sub 2-3

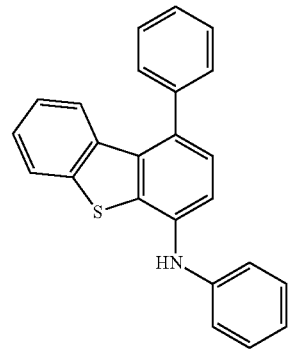

Sub 2-4

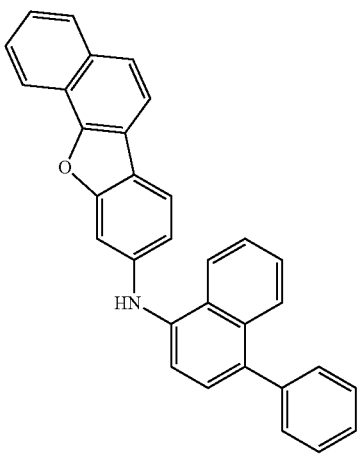

Sub 2-5

Sub 2-6
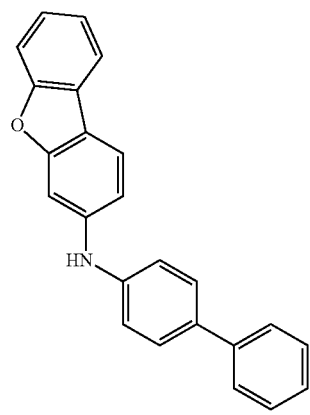
Sub 2-10
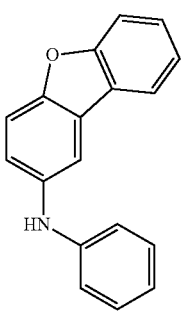
Sub 2-7
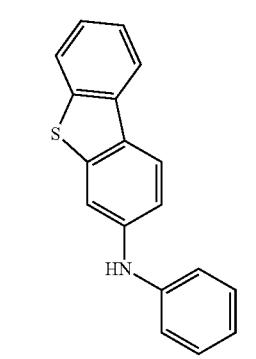
Sub 2-11
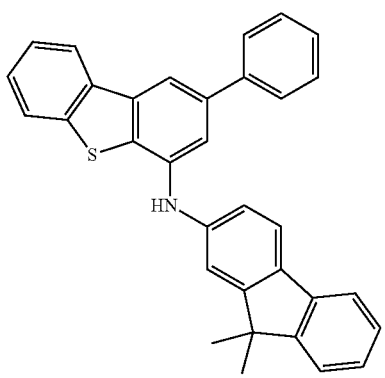
Sub 2-8
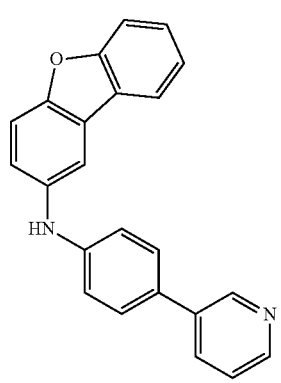
Sub 2-12
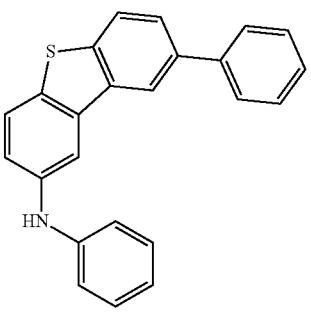
Sub 2-9
Sub 2-13
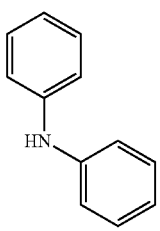
Sub 2-14

Sub 2-15
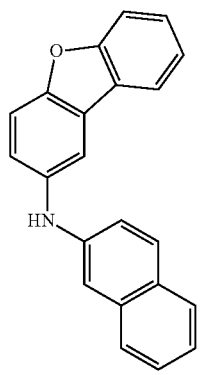
Sub 2-16
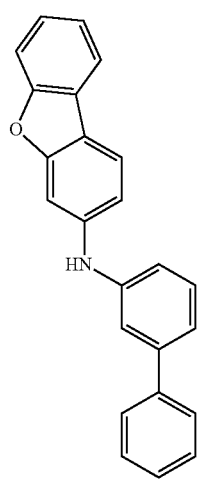
Sub 2-17
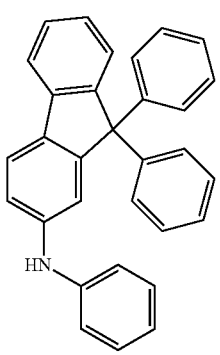
Sub 2-18
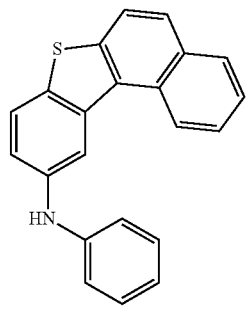
Sub 2-19
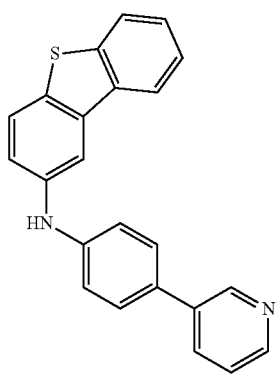
Sub 2-20
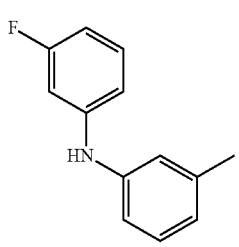
Sub 2-21
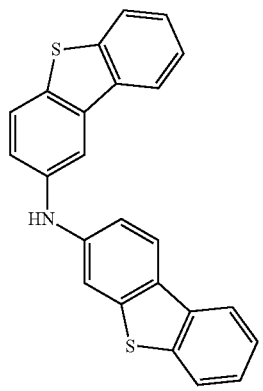
Sub 2-22
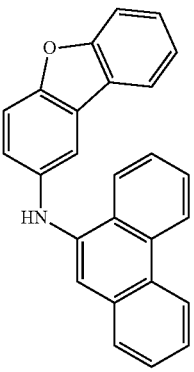

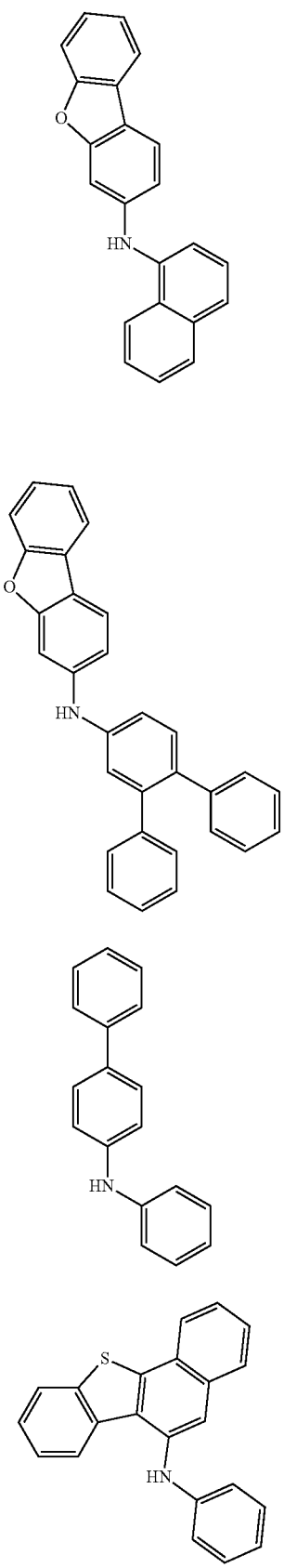

-continued
Sub 2-31
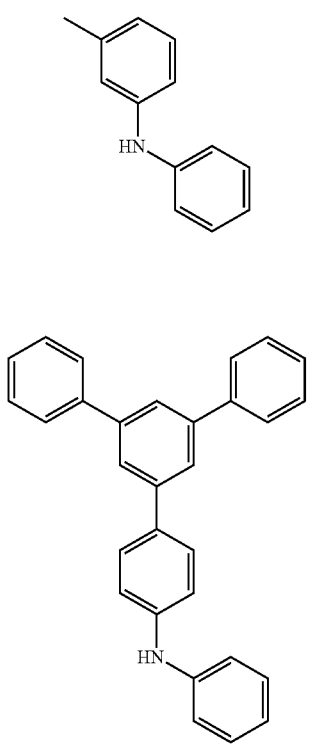
Sub 2-32
Sub 2-33
Sub 2-34
-continued
Sub 2-35
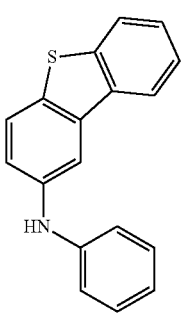
Sub 2-36
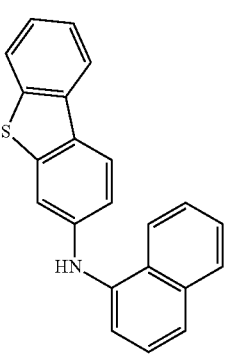
Sub 2-37
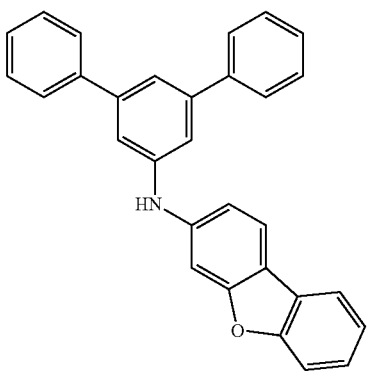
Sub 2-38
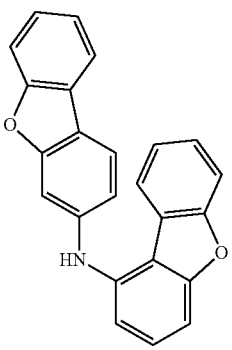

Sub 2-39
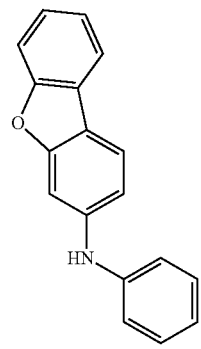
Sub 2-40
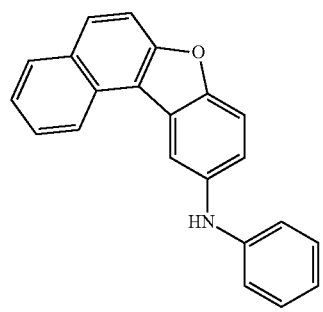
Sub 2-41
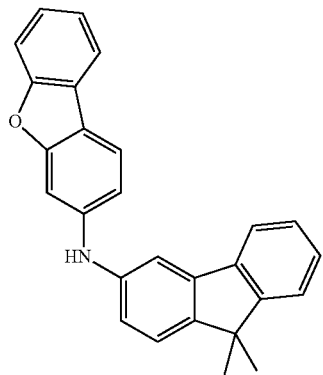
Sub 2-42
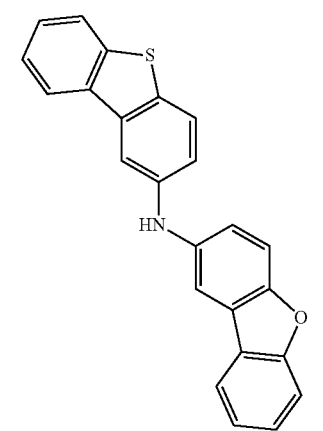
Sub 2-43
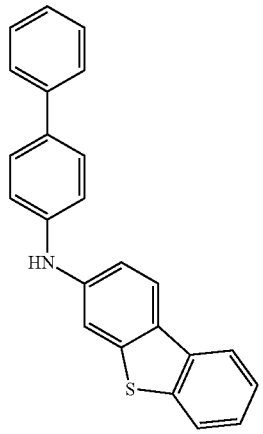
Sub 2-44
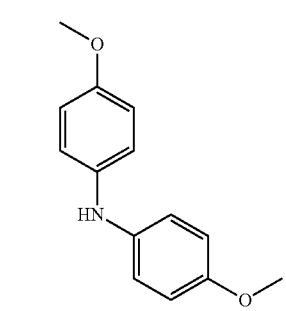
Sub 2-45
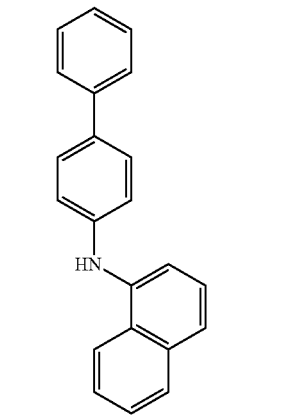
Sub 2-46
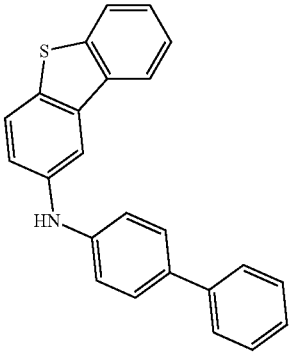

Sub 2-47
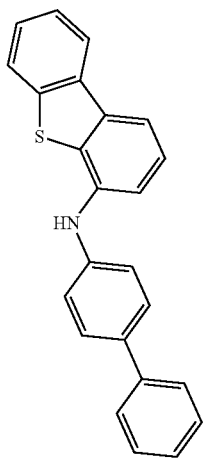
Sub 2-48
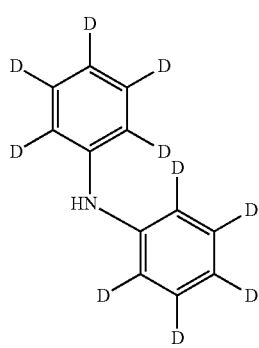
Sub 2-49
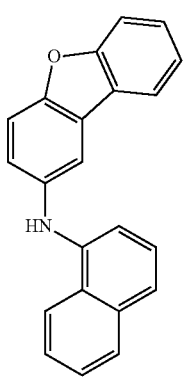
Sub 2-50
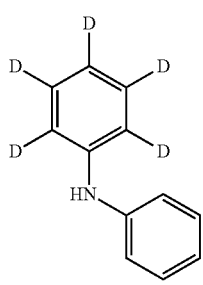
Sub 2-51
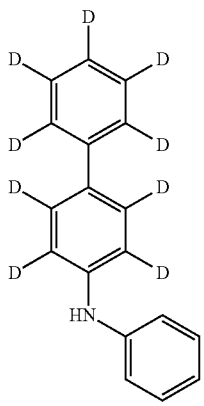
Sub 2-52
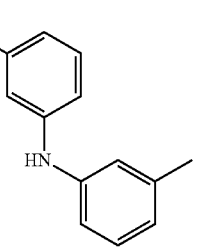
Sub 2-53
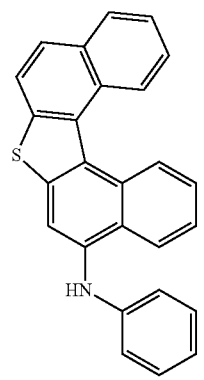
Sub 2-54
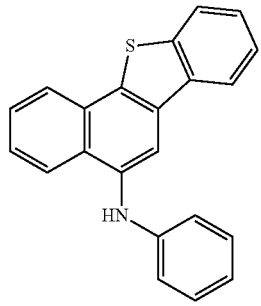

Sub 2-55
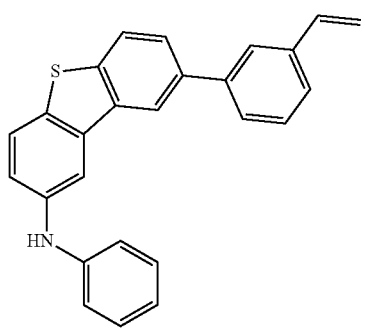
Sub 2-58
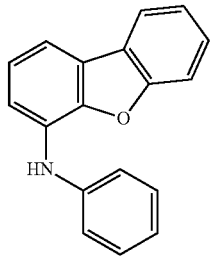
Sub 2-56
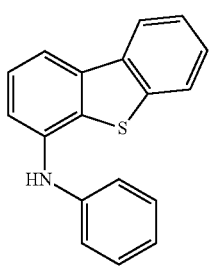
Sub 2-59
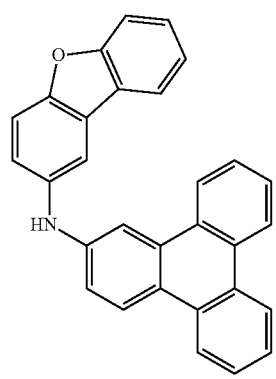
Sub 2-57
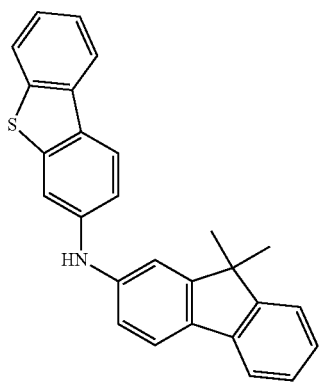
Sub 2-60
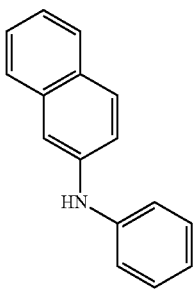
TABLE 2
| compound | FD-MS | compound | FD-MS |
| --- | --- | --- | --- |
| Sub 2-12 | m/z = 351.11($C_{24}H_{17}NS$ = 351.47) | Sub 2-13 | m/z = 169.09($C_{12}H_{11}N$ = 169.23) |
| Sub 2-14 | m/z = 219.10($C_{16}H_{13}N$ = 219.29) | Sub 2-16 | m/z = 335.13($C_{24}H_{17}NO$ = 335.41) |
| Sub 2-19 | m/z = 352.10($C_{23}H_{16}N_2S$ = 352.46) | Sub 2-25 | m/z = 245.12($C_{18}H_{15}N$ = 245.33) |
| Sub 2-28 | m/z = 325.09($C_{22}H_{15}NS$ = 325.43) | Sub 2-31 | m/z = 183.10($C_{13}H_{13}N$ = 183.25) |
| Sub 2-34 | m/z = 351.11($C_{24}H_{17}NS$ = 351.47) | Sub 2-35 | m/z = 275.08($C_{18}H_{13}NS$ = 275.37) |
| Sub 2-43 | m/z = 351.11($C_{24}H_{17}NS$ = 351.47) | Sub 2-46 | m/z = 351.11($C_{24}H_{17}NS$ = 351.47) |
| Sub 2-56 | m/z = 275.08($C_{18}H_{13}NS$ = 275.37) | Sub 2-57 | m/z = 391.14($C_{27}H_{21}NS$ = 391.53) |
| Sub 2-58 | m/z = 259.10($C_{18}H_{13}NO$ = 259.31) | Sub 2-60 | m/z = 219.10($C_{16}H_{13}N$ = 219.29) |

III. Synthesis of Product

1. Synthesis of P-7

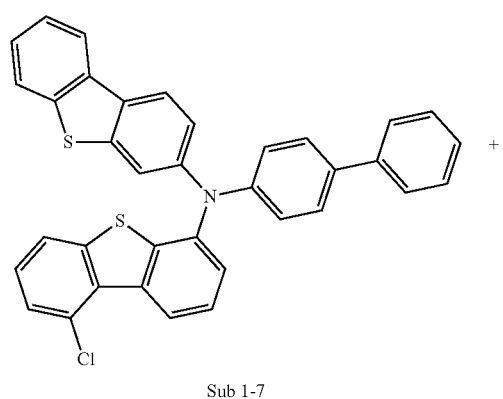

Sub 1-7

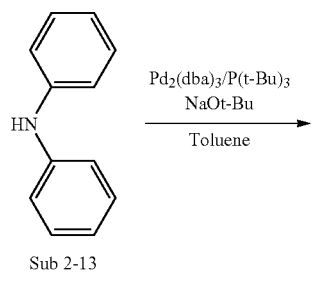

Sub 2-13

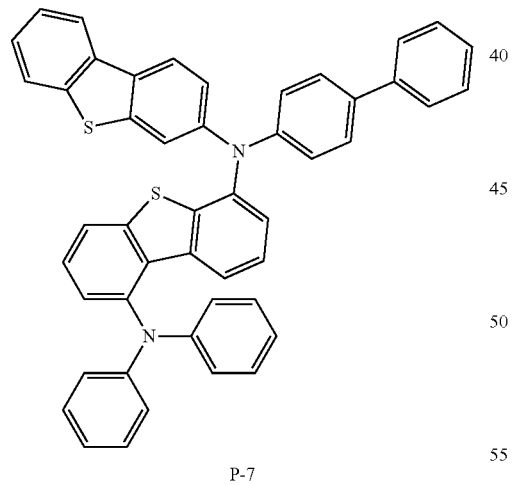

P-7

Sub 1-7 (2.50 g, 4.40 mmol), Sub 2-13 (0.74 g, 4.40 mmol), Pd$_2$(dba)$_3$ (0.12 g, 0.13 mmol), NaOt-Bu (0.85 g, 8.80 mmol), P(t-bu)$_3$ (0.09 g, 0.44 mmol), toluene (30 ml) were added and refluxed at 120° C. for 8 hours. When the reaction was completed, the temperature of the reaction was cooled to room temperature, extracted with MC and wiped with water. The organic layer was dried over MgSO$_4$ and concentrated. The resulting compound was separated by silicagel column chromatography to obtain the product. (2.50 g, 81%)

2. Synthesis of P-22

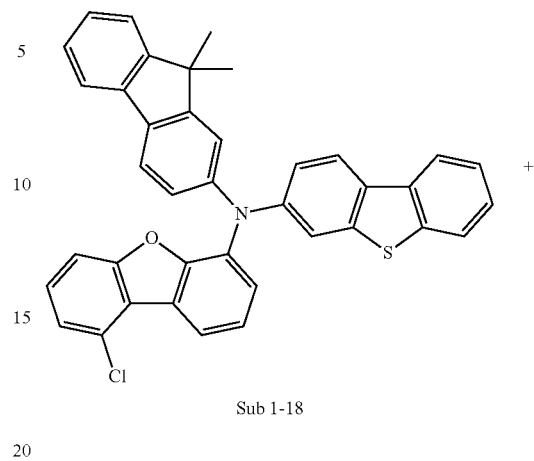

Sub 1-18

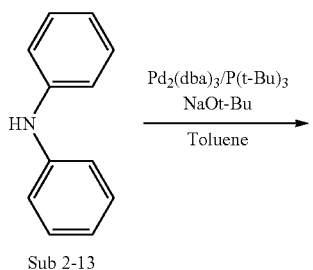

Sub 2-13

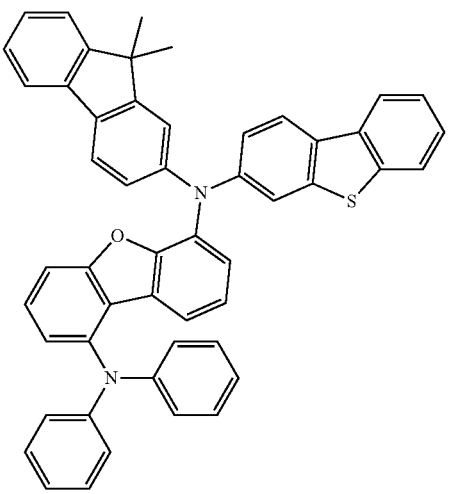

P-22

Sub 1-18 (3.30 g, 5.57 mmol), Sub 2-13 (0.94 g, 5.57 mmol), Pd$_2$(dba)$_3$ (0.15 g, 0.17 mmol), NaOt-Bu (1.07 g, 11.15 mmol), P(t-bu)$_3$ (0.11 g, 0.56 mmol), toluene (40 ml) were carried out in the same manner as in P-7 to give the product (3.19 g, 79%).

3. Synthesis of P-28
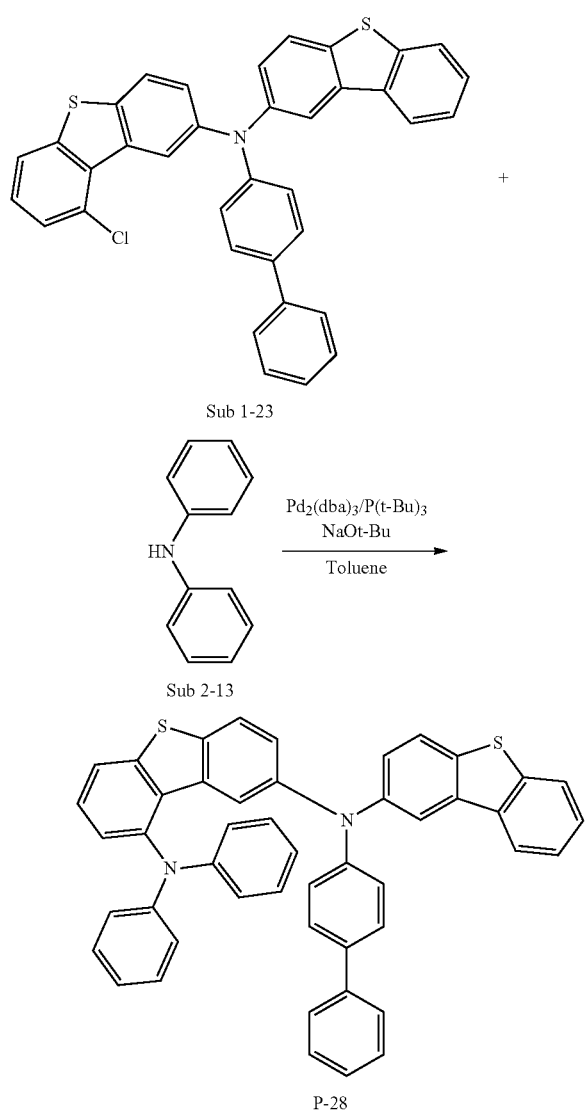
Sub 1-23 (2.72 g, 5.10 mmol), Sub 2-13 (0.86 g, 5.10 mmol), Pd$_2$(dba)$_3$ (0.14 g, 0.15 mmol), NaOt-Bu (0.98 g, 10.19 mmol), P(t-bu)$_3$ (0.10 g, 0.51 mmol), toluene (30 ml) were carried out in the same manner as in P-7 to give the product (2.96 g, 83%).
4. Synthesis of P-62
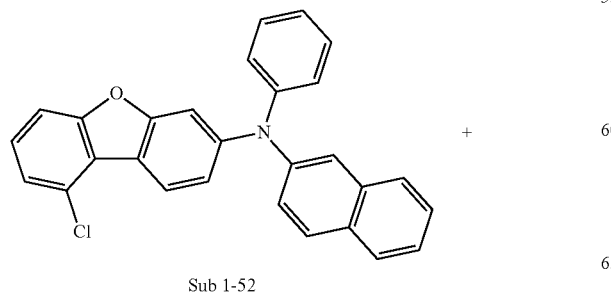
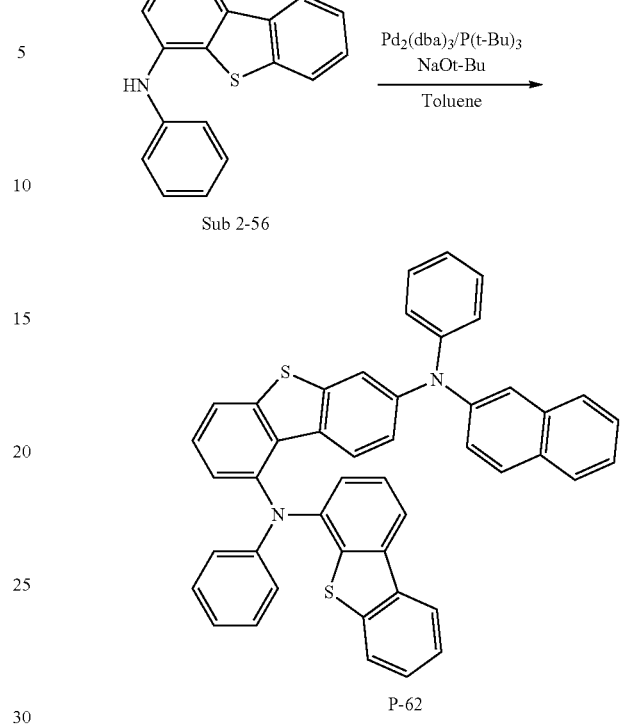
Sub 1-52 (1.70 g, 3.90 mmol), Sub 2-56 (1.07 g, 3.90 mmol), Pd$_2$(dba)$_3$ (0.11 g, 0.12 mmol), NaOt-Bu (0.75 g, 7.80 mmol), P(t-bu)$_3$ (0.08 g, 0.39 mmol), toluene (20 ml) were carried out in the same manner as in P-7 to give the product (2.32 g, 88%).
5. Synthesis of P-73
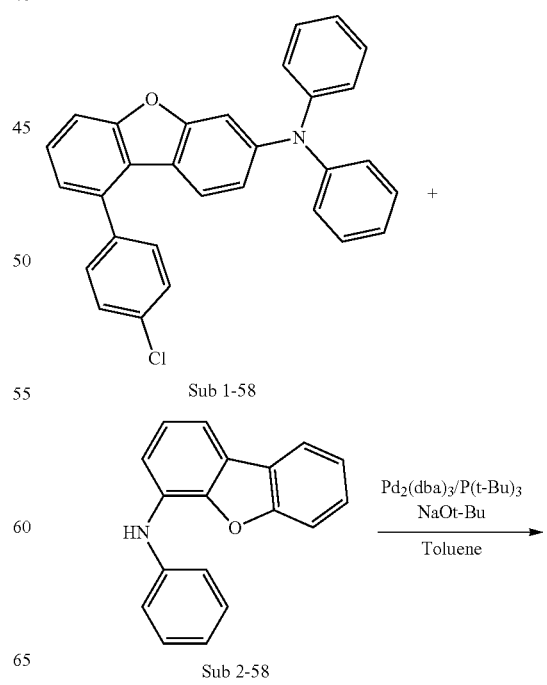

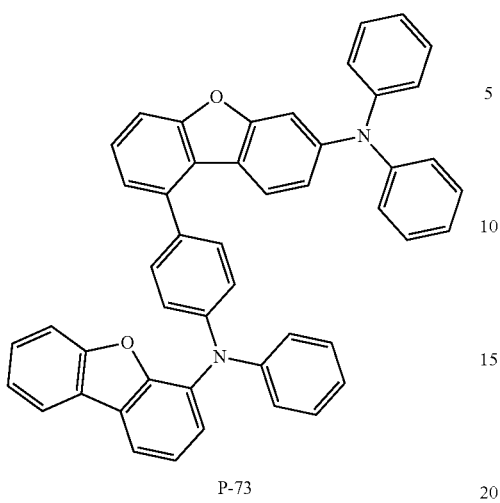

P-73

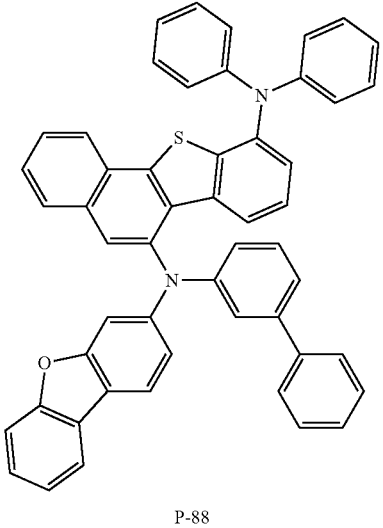

P-88

Sub 1-58 (3.00 g, 6.73 mmol), Sub 2-58 (1.74 g, 6.73 mmol), Pd$_2$(dba)$_3$ (0.18 g, 0.20 mmol), NaOt-Bu (1.29 g, 13.45 mmol), P(t-bu)$_3$ (0.14 g, 0.67 mmol), toluene (40 ml) were carried out in the same manner as in P-7 to give the product (3.78 g, 84%).

6. Synthesis of P-88

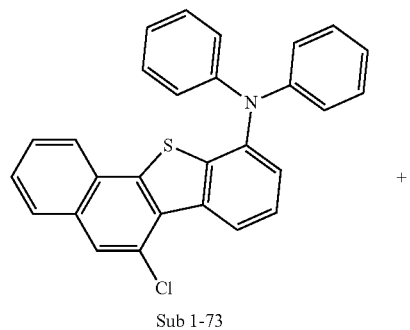

Sub 1-73

+

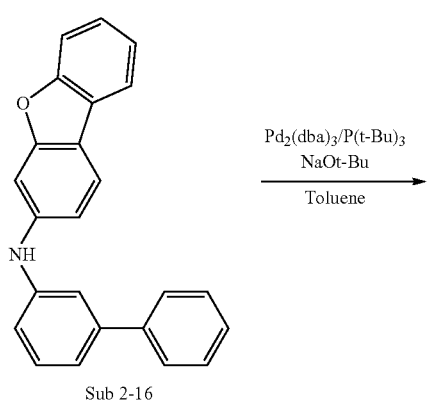

Sub 2-16

$\xrightarrow{\text{Pd}_2(\text{dba})_3/\text{P}(t\text{-Bu})_3}_{\text{NaOt-Bu}}$ Toluene Sub 1-73 (3.25 g, 7.45 mmol), Sub 2-16 (2.50 g, 7.45 mmol), Pd$_2$(dba)$_3$ (0.20 g, 0.22 mmol), NaOt-Bu (1.43 g, 14.91 mmol), P(t-bu)$_3$ (0.15 g, 0.75 mmol), toluene (35 ml) were carried out in the same manner as in P-7 to give the product (3.94 g, 72%).

TABLE 3

| compound | FD-MS | compound | FD-MS |
|---|---|---|---|
| P-4 | m/z = 624.17 (C$_{42}$H$_{28}$N$_2$S$_2$ = 624.82) | P-5 | m/z = 658.21 (C$_{46}$H$_{30}$N$_2$OS = 658.82) |
| P-7 | m/z = 700.20 (C$_{48}$H$_{32}$N$_2$S$_2$ = 700.92) | P-22 | m/z = 724.25 (C$_{51}$H$_{36}$N$_2$OS = 724.92) |
| P-24 | m/z = 642.23 (C$_{46}$H$_{30}$N$_2$O$_2$ = 642.76) | P-26 | m/z = 700.20 (C$_{48}$H$_{32}$N$_2$S$_2$ = 700.92) |
| P-28 | m/z = 700.20 (C$_{48}$H$_{32}$N$_2$S$_2$ = 700.92) | P-34 | m/z = 730.16 (C$_{48}$H$_{30}$N$_2$S$_3$ = 730.96) |
| P-38 | m/z = 700.20 (C$_{48}$H$_{32}$N$_2$S$_2$ = 700.92) | P-48 | m/z = 608.19 (C$_{42}$H$_{28}$N$_2$OS = 608.76) |
| P-53 | m/z = 698.20 (C$_{48}$H$_{30}$N$_2$O$_2$S = 698.84) | P-62 | m/z = 674.19 (C$_{46}$H$_{30}$N$_2$S$_2$ = 674.88) |
| P-67 | m/z = 730.16 (C$_{48}$H$_{30}$N$_2$S$_3$ = 730.96) | P-73 | m/z = 668.25 (C$_{48}$H$_{32}$N$_2$O$_2$ = 668.80) |
| P-79 | m/z = 780.17 (C$_{52}$H$_{32}$N$_2$S$_3$ = 781.02) | P-86 | m/z = 784.25 (C$_{56}$H$_{36}$N$_2$OS = 784.98) |
| P-88 | m/z = 734.24 (C$_{52}$H$_{34}$N$_2$OS = 734.92) | P-90 | m/z = 750.22 (C$_{52}$H$_{34}$N$_4$S$_2$ = 750.98) |

Otherwise, the synthesis examples of the present invention represented by Formulas (1) have been described, but these are all based on the Buchwald-Hartwig cross coupling reaction, Suzuki cross-coupling reaction, Miyaura boration reaction, Intramolecular acid-induced cyclization reaction (J. mater. Chem. 1999, 9, 2095), Pd(II)-catalyzed oxidative cyclization reaction (Org. Lett. 2011, 13, 5504), and those skilled in the art will readily understand that the above reaction proceeds even when, besides the substituent specified in the specific synthesis example, other substituents (X, Y, Ar$^1$ to Ar$^4$, L$^a$, L$^b$, R$^1$ to R$^9$, n and m) defined in Formula (1) are bonded. For example, Sub 1→Final Products reaction in Reaction Scheme 1, Sub 1-c→Sub 1 reaction, Sub 1-e→Sub 1 reaction in Reaction Scheme 2, starting material→Sub 2 reaction in Reaction Scheme 3 are all based on the Buchwald-Hartwig cross coupling reaction, and starting material→Sub 1-a reaction and starting material→Sub 1-d in Reaction Scheme 2 is based on the Suzuki cross-coupling reaction, and Sub 1-b→Sub 1-c reaction is based on the Intramolecular acid-induced cyclization reaction reaction (J. mater. Chem. 1999, 9, 2095.) Sub 1-d→Sub 1-e reaction is based on the Pd(II)-catalyzed oxidative cyclization reaction (Org. Lett. 2011, 13, 5504). The above reactions will proceed even if a substituent not specifically mentioned is bonded.

Evaluation of Manufacture of Organic Electric Element

[Example 1] Red Organic Light Emitting Diode (Emitting Auxiliary Layer)

An organic electric element was fabricated according to a conventional method using the compound of the present invention as an emitting auxiliary layer material. First, on an ITO layer (anode) formed on a glass substrate, 4,4',4"-Tris[2-naphthyl(phenyl)amino]triphenylamine (hereinafter will be abbreviated as 2-TNATA) was vacuum-deposited to form a hole injection layer with a thickness of 60 nm, and NPB was vacuum deposited on the hole injection layer to a thickness of 60 nm to form a hole transport layer. Subsequently, the compound P-1 of the present invention was vacuum-deposited on the hole transport layer to a thickness of 20 nm to form an emitting auxiliary layer, and on the emitting auxiliary layer, 4,4'-N,N'-dicarbazole-biphenyl (hereinafter will be abbreviated as CPB) was used as a host material, and bis-(1-phenylisoquinolyl)iridium(III)acetylacetonate (hereinafter will be abbreviated as (piq)$_2$H(acac)) was doped as a dopant material in a weight ratio of 95:5, followed by vacuum deposition to a thickness of 30 nm to form an emitting layer. Subsequently, BAlq was vacuum deposited on the emitting layer to a thickness of 5 nm to form a hole blocking layer, and Bis(10-hydroxybenzo[h]quinolinato)beryllium (hereinafter will be abbreviated as BeBq$_2$) was vacuum deposited on the hole blocking layer to a thickness of 40 nm to form an electron transport layer. After that, an alkali metal halide, LiF was vacuum deposited as an electron injection layer to a thickness of 0.2 nm, and Al was deposited to a thickness of 150 nm to form a cathode to manufacture an OLED.

[Example 2] to [Example 30] Red Organic Light Emitting Diode (Emitting Auxiliary Layer)

An organic electric element was fabricated in the same manner as in Example 1, except that the compounds P-2 to P-90 of the present invention described in Table 4 were used instead of the compound P-1 of the present invention as the emitting auxiliary layer material.

Comparative Examples 1

An organic electric element was fabricated in the same manner as in Example 1, except that no emitting auxiliary layer was formed.

[Comparative Examples 2] to [Comparative Examples 6]

An organic electric element was fabricated in the same manner as in Example 1, except that the comparative compounds 1 to 5 described in Table 4 were used instead of the compound P-1 of the present invention as the emitting auxiliary layer material.

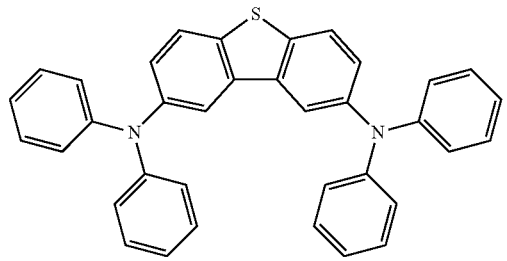

<comparative compound 1>

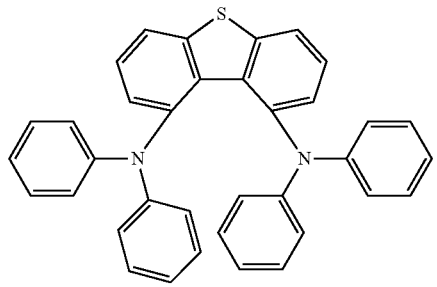

<comparative compound 2>

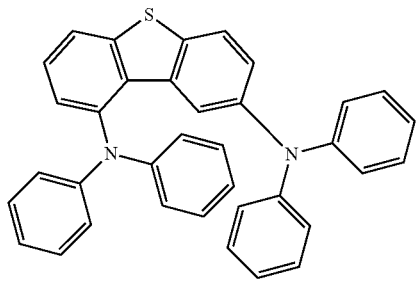

<comparative compound 3>

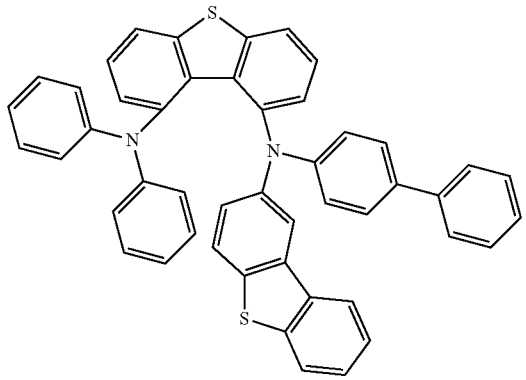

<comparative compound 4>

<comparative compound 5>

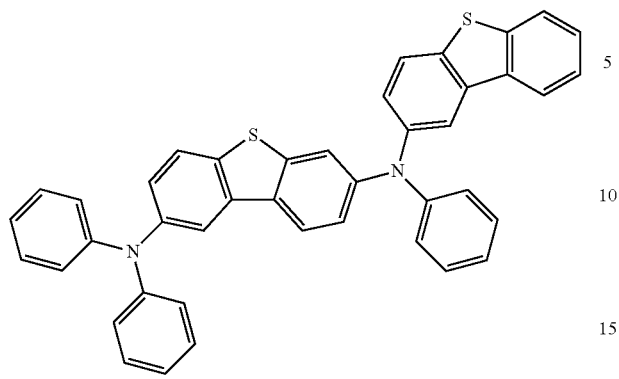

To the OLEDs which were manufactured by examples 1 to 30 and comparative examples 1 to 6 of the present invention, a forward bias direct current voltage was applied, and electroluminescent (EL) properties were measured using PR-650 of Photoresearch Co., and T95 life was measured using a life measuring apparatus manufactured by McScience Inc. with a reference luminance of 2500 cd/m$^2$, and the measurement results are shown in Table 4 below.

TABLE 4

|   | compound | Voltage (V) | Current Density (mA/cm$^2$) | Brightness (cd/m$^2$) | Efficiency (cd/A) | Lifetime T(95) | CIE x | y |
|---|---|---|---|---|---|---|---|---|
| comparative example(1) | — | 6.5 | 34.7 | 2500 | 7.2 | 62.9 | 0.66 | 0.32 |
| comparative example(2) | comparative compound 1 | 6.0 | 24.0 | 2500 | 10.4 | 84.5 | 0.67 | 0.32 |
| comparative example(3) | comparative compound 2 | 6.4 | 25.3 | 2500 | 9.9 | 81.0 | 0.66 | 0.33 |
| comparative example(4) | comparative compound 3 | 6.0 | 18.0 | 2500 | 13.9 | 91.3 | 0.66 | 0.35 |
| comparative example(5) | comparative compound 4 | 5.9 | 15.7 | 2500 | 15.9 | 96.8 | 0.66 | 0.35 |
| comparative example(6) | comparative compound 5 | 5.7 | 13.5 | 2500 | 18.5 | 118.3 | 0.66 | 0.35 |
| example(1) | compound(P-1) | 5.6 | 11.8 | 2500 | 21.1 | 115.1 | 0.66 | 0.34 |
| example(2) | compound(P-2) | 5.7 | 11.8 | 2500 | 21.2 | 116.2 | 0.66 | 0.34 |
| example(3) | compound(P-4) | 5.7 | 11.7 | 2500 | 21.4 | 118.5 | 0.66 | 0.34 |
| example(4) | compound(P-5) | 5.6 | 11.9 | 2500 | 21.0 | 116.8 | 0.66 | 0.35 |
| example(5) | compound(P-7) | 5.7 | 11.6 | 2500 | 21.6 | 118.6 | 0.66 | 0.34 |
| example(6) | compound(P-9) | 5.6 | 11.4 | 2500 | 22.0 | 120.8 | 0.66 | 0.34 |
| example(7) | compound(P-12) | 5.6 | 12.1 | 2500 | 20.6 | 111.1 | 0.66 | 0.34 |
| example(8) | compound(P-18) | 5.6 | 12.1 | 2500 | 20.6 | 111.5 | 0.66 | 0.35 |
| example(9) | compound(P-21) | 5.7 | 13.0 | 2500 | 19.2 | 109.7 | 0.66 | 0.34 |
| example(10) | compound(P-26) | 5.5 | 9.8 | 2500 | 25.5 | 129.1 | 0.66 | 0.34 |
| example(11) | compound(P-27) | 5.5 | 9.9 | 2500 | 25.3 | 128.5 | 0.66 | 0.35 |
| example(12) | compound(P-28) | 5.5 | 9.6 | 2500 | 26.0 | 133.2 | 0.66 | 0.34 |
| example(13) | compound(P-29) | 5.5 | 9.9 | 2500 | 25.3 | 129.3 | 0.66 | 0.34 |
| example(14) | compound(P-31) | 5.5 | 9.8 | 2500 | 25.6 | 128.0 | 0.66 | 0.35 |
| example(15) | compound(P-32) | 5.6 | 10.3 | 2500 | 24.2 | 125.3 | 0.66 | 0.34 |
| example(16) | compound(P-34) | 5.6 | 9.9 | 2500 | 25.3 | 129.4 | 0.66 | 0.34 |
| example(17) | compound(P-35) | 5.5 | 9.8 | 2500 | 25.6 | 128.4 | 0.66 | 0.35 |
| example(18) | compound(P-38) | 5.5 | 10.1 | 2500 | 24.8 | 123.6 | 0.66 | 0.34 |
| example(19) | compound(P-40) | 5.7 | 10.5 | 2500 | 23.8 | 122.0 | 0.66 | 0.34 |
| example(20) | compound(P-48) | 5.6 | 11.9 | 2500 | 21.0 | 116.7 | 0.66 | 0.34 |
| example(21) | compound(P-49) | 5.6 | 12.0 | 2500 | 20.8 | 111.4 | 0.66 | 0.34 |
| example(22) | compound(P-53) | 5.6 | 11.3 | 2500 | 22.1 | 120.9 | 0.66 | 0.35 |
| example(23) | compound(P-54) | 5.7 | 10.5 | 2500 | 23.7 | 122.2 | 0.66 | 0.35 |
| example(24) | compound(P-57) | 5.7 | 10.3 | 2500 | 24.2 | 124.1 | 0.66 | 0.34 |
| example(25) | compound(P-60) | 5.6 | 11.1 | 2500 | 22.5 | 119.8 | 0.66 | 0.34 |
| example(26) | compound(P-62) | 5.6 | 10.9 | 2500 | 22.8 | 122.9 | 0.66 | 0.34 |
| example(27) | compound(P-64) | 5.6 | 10.7 | 2500 | 23.3 | 122.2 | 0.66 | 0.34 |
| example(28) | compound(P-65) | 5.7 | 11.7 | 2500 | 21.4 | 118.2 | 0.66 | 0.35 |
| example(29) | compound(P-71) | 5.7 | 12.4 | 2500 | 20.2 | 112.0 | 0.66 | 0.34 |
| example(30) | compound(P-90) | 5.6 | 10.8 | 2500 | 23.2 | 122.7 | 0.66 | 0.35 |

As can be seen from the results of Table 4, when a red organic electroluminescent device is manufactured using the material for an organic electric element of the present invention as an emitting auxiliary layer material, the driving voltage of the organic electric element can be lowered and the luminous efficiency and lifetime can be remarkably improved as compared with the comparative examples in which the emitting auxiliary layer is not used or the comparative compounds 1 to 5 are used.

Comparing the results of Comparative Compounds 1 to 3, the comparative compound 3 in which diarylamine was substituted at positions 1 and 8 in the dibenzothiophene core showed the best results. Even though the same core is used, the energy level (especially the HOMO level) varies depending on the substitution position, and as the physical properties of the compound are changed, it can be seen that these different results appear as a major factor in improving the device performance in the device deposition. It can be confirmed that the compound in which diarylamine is asymmetrically substituted at positions 1 and 8 in the dibenzothiophene core has a remarkable effect as compared with symmetrically substituted compounds.

Comparing the results of Comparative Compound 3 with Examples 1 to 30, it can be confirmed that the compound of the present invention in which a specific substituent group such as dibenzothiophene or dibenzofurane is substituted in the amine group is significantly improved over the comparative compound 3 in which the diarylamine is substituted even if the substitution position is the same.

These results indicate that when dibenzothiophenes or dibenzofurans are introduced as substituents, the refractive index is significantly higher and the Tg value is higher than when the substituents of the general aryl groups are substituted.

TABLE 5

| Compound | Compound of the present invention p-28 |
|---|---|
| Structure | 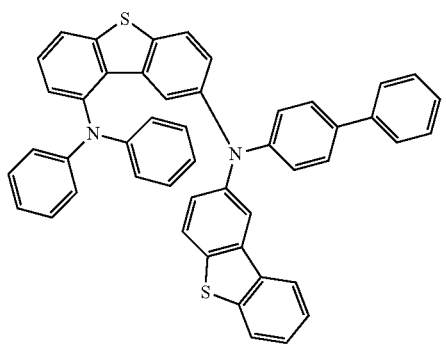 [SMILES: c1ccc(-c2ccc(N(c3ccc4sc5ccccc5c4c3)c3ccc4sc5cccc(N(c6ccccc6)c6ccccc6)c5c4c3)cc2)cc1] |
| T1(eV) | 2.7640 |

TABLE 5-continued

| Compound | Compound of the present invention p-35 |
|---|---|
| Structure | 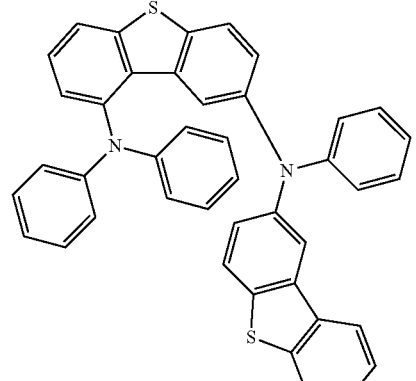 |
| T1(eV) | 2.7747 |
| Compound | Comparative Compound 4 |
| Structure | 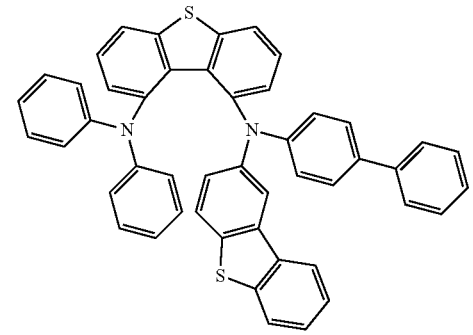 [SMILES: c1ccc(-c2ccc(N(c3ccc4sc5ccccc5c4c3)c3cccc4sc5cccc(N(c6ccccc6)c6ccccc6)c5c34)cc2)cc1] |
| T1(eV) | 2.6618 |
| Compound | Comparative Compound 5 |
| Structure | 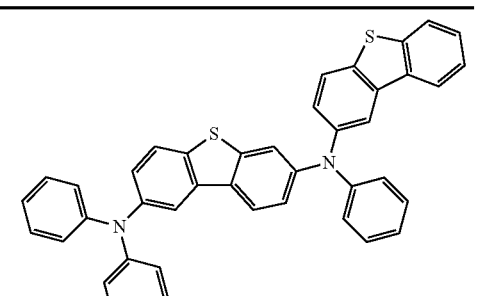 |
| T1(eV) | 2.6987 |

The results in Table 5 show that, even when the core and the specific amine substituent are the same as the dibenzothiophene, the result is different depending on the bonding position of the amine substituent.

Compounds of the present invention P-28, P-35 wherein the amine substitution positions are bonded at positions 1 and 8 have higher T1 value than Comparative compound 4 in which the amine substituent is bonded at 1 and 9 or Comparative compound 5 in which the amine substituent is bonded at 2 and 7, and as a result, the ability to block the electrons is improved, which results in easier charge balance, and thus the luminous efficiency is remarkably improved.

In addition, in the evaluation results of the above-described device manufacture, the device characteristics in which the compound of the present invention is applied only to the emitting auxiliary layer have been described. However, the compound of the present invention may be applied to the hole transport layer or both the hole transport layer and the emitting auxiliary layer.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:

1. An organic electric element comprising a first electrode, a second electrode, and an organic material layer disposed between the first electrode and the second electrode,
wherein the organic material layer comprises a hole injection layer, a hole transport layer, an emitting auxiliary layer, an emitting layer, an electron transport layer, and electron injection layer,
wherein the emitting auxiliary layer is located between the emitting layer and the hole transport layer, and the hole injection layer is located between the hole transport layer and the first electrode, and
wherein the emitting auxiliary layer comprises a compound represented by any of Formulas (2) to (7):

Formula (2)

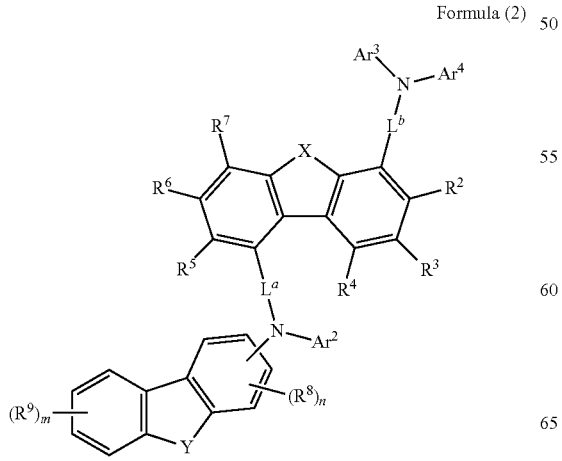

Formula (3)

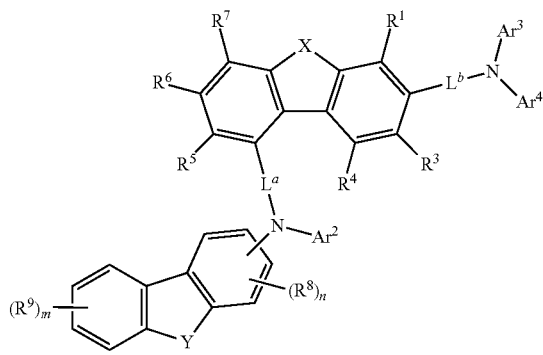

Formula (4)

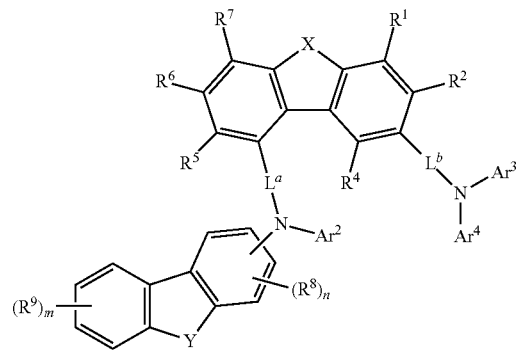

Formula (5)

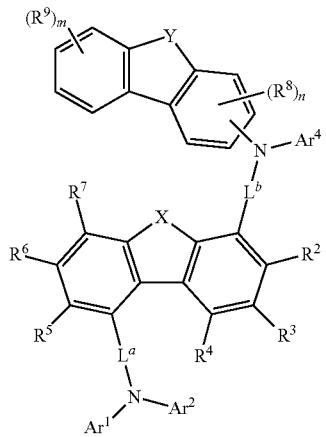

-continued

Formula (6)

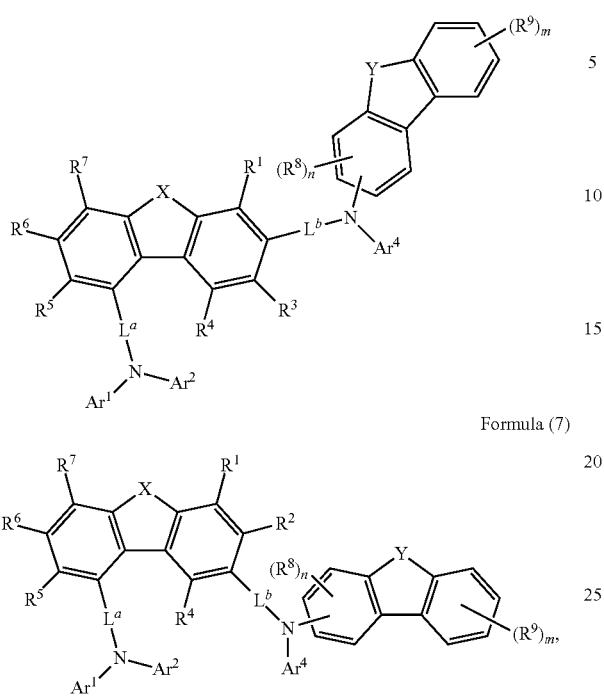

Formula (7)

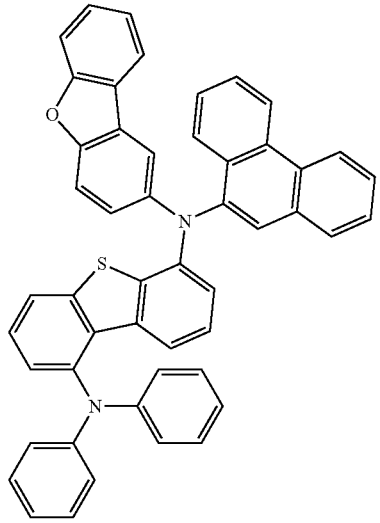

P-1

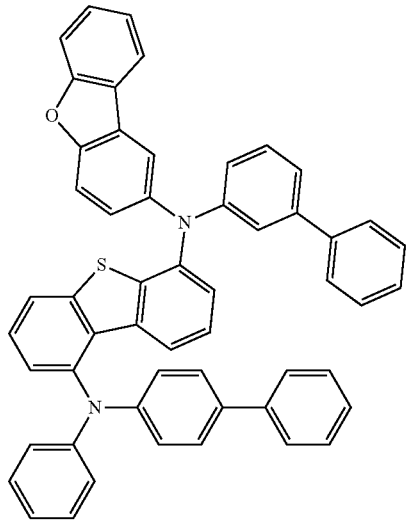

P-2

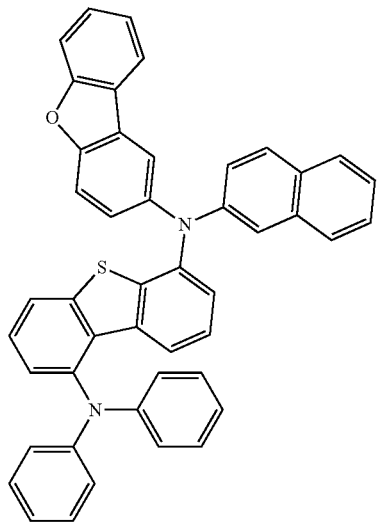

P-3 wherein:
1) X and Y are each O or S,
2) $R^1$, $R^2$ and $R^3$ are each independently selected from the group consisting of hydrogen; deuterium; a $C_6$-$C_{24}$ aryl group;
3) $R^4$, $R^5$, $R^6$ and $R^7$ are each independently selected from the group consisting of hydrogen; deuterium; a $C_6$-$C_{24}$ aryl group;
4) wherein any one of two adjacent $R^1$ and $R^2$, $R^2$ and $R^3$, $R^3$ and $R^4$, $R^5$ and $R^6$, $R^6$ and $R^7$ may be bonded to form an aromatic or heteroaromatic ring,
5) $Ar^1$, $Ar^2$, $Ar^3$ and $Ar^4$ are each independently selected from the group consisting of a $C_6$-$C_{24}$ aryl group; a fluorenyl group; a $C_2$-$C_{24}$ heterocyclic group including at least one hetero atom of O, N, S, Si or P;
6) $L^a$ and $L^b$ are each independently single bond; a $C_6$-$C_{24}$ arylene group;
7) n is an integer of 0 to 3, and m is an integer of 0 to 4,
8) $R^8$ and $R^9$ are each independently selected from the group consisting of hydrogen; deuterium; a $C_6$-$C_{24}$ aryl group; or in case n and m are 2 or more, and $R^8$ and $R^9$ are each in plural being the same or different, and a plurality of $R^8$ or a plurality of $R^9$ combine to each other to form an aromatic ring,
wherein, the aryl group, fluorenyl group, arylene group, heterocyclic group, alkyl group may be substituted with one or more substituents selected from the group consisting of deuterium; halogen; a silane group substituted or unsubstituted with $C_1$-$C_{20}$ alkyl group or $C_6$-$C_{20}$ aryl group; $C_1$-$C_{20}$ alkyl group; $C_6$-$C_{20}$ aryl group; $C_6$-$C_{20}$ aryl group substituted with deuterium.

2. The organic electric element according to claim 1 wherein at least one of $L^a$ and $L^b$ in Formulas (2) to (7) is a single bond.

3. The organic electric element according to claim 1 wherein the compound represented by Formulas (2) to (7) is any one of Compounds P-1 to P-90:

P-4
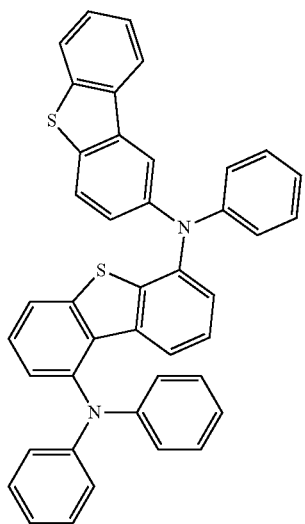
P-5
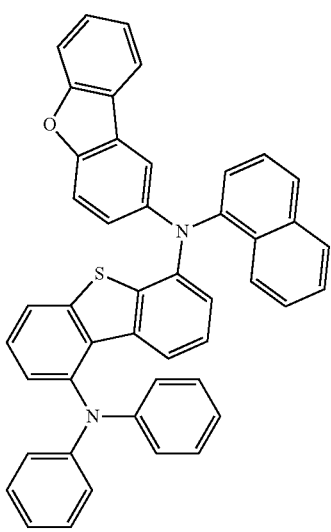
P-6
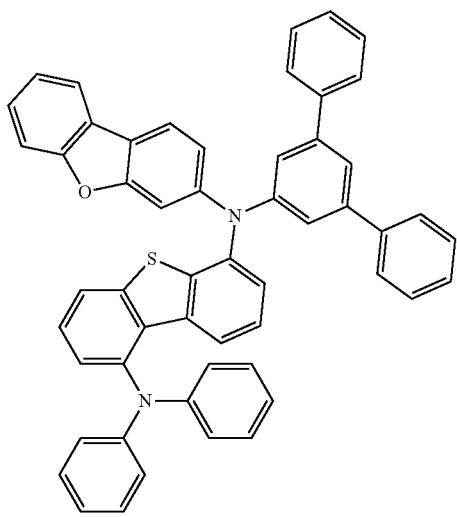
P-7
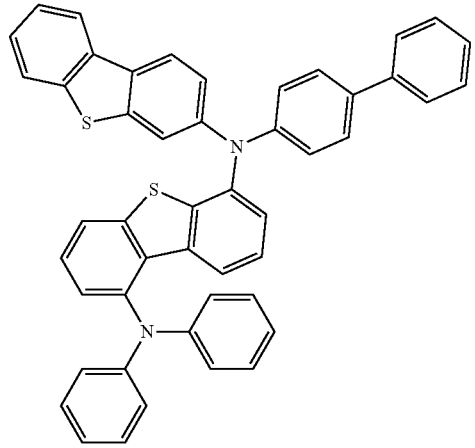
P-8
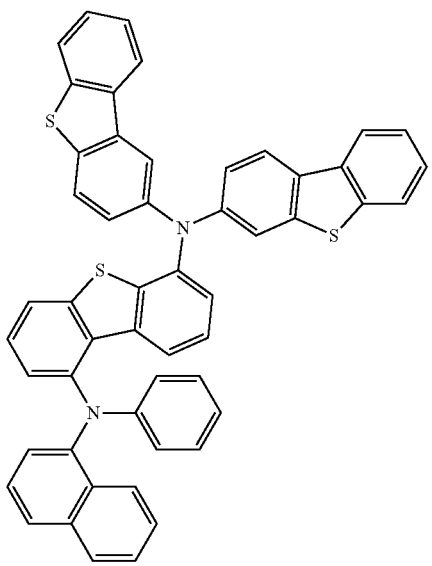
P-9
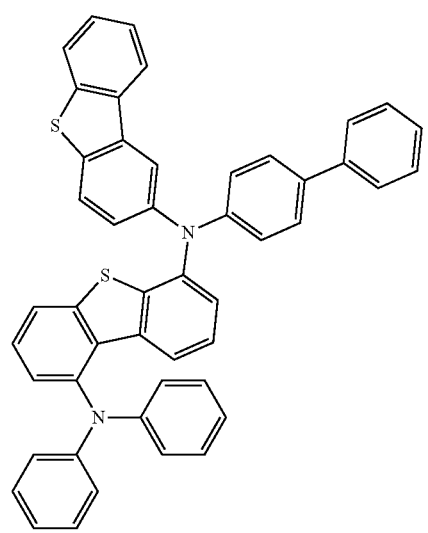

P-10
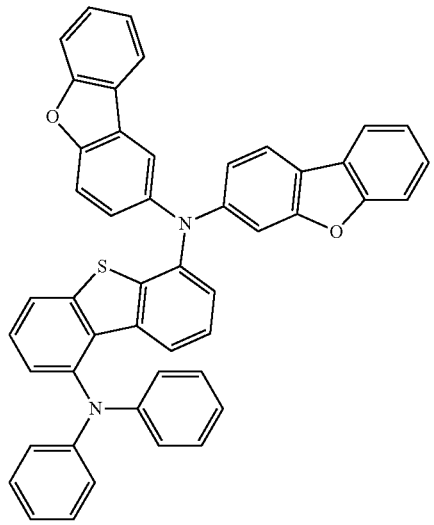
P-13
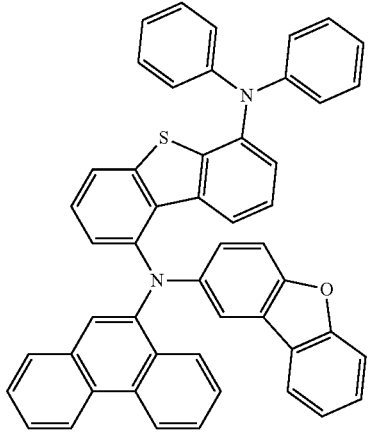
P-11
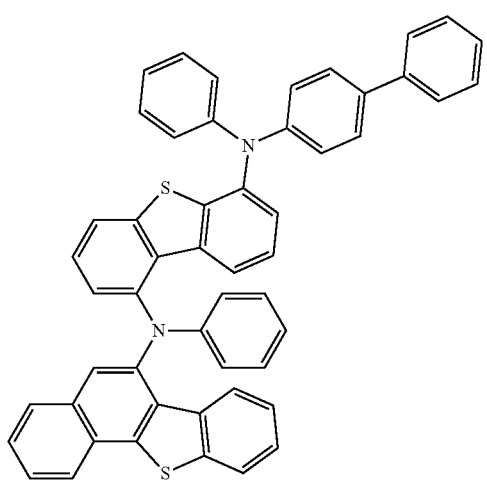
P-14
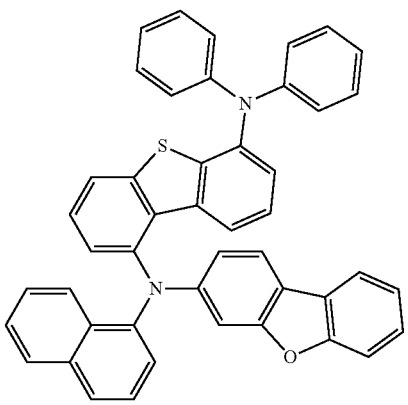
P-12
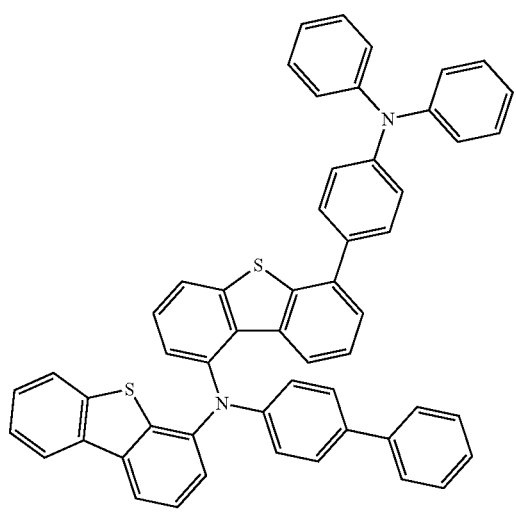
P-15
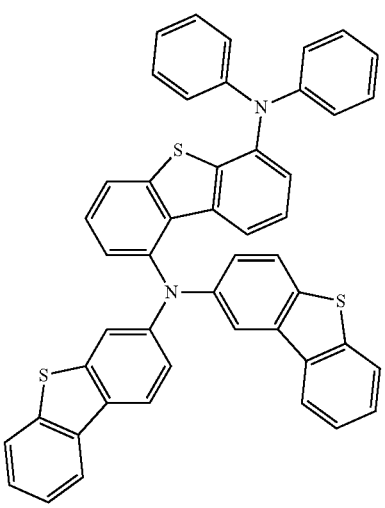

P-16
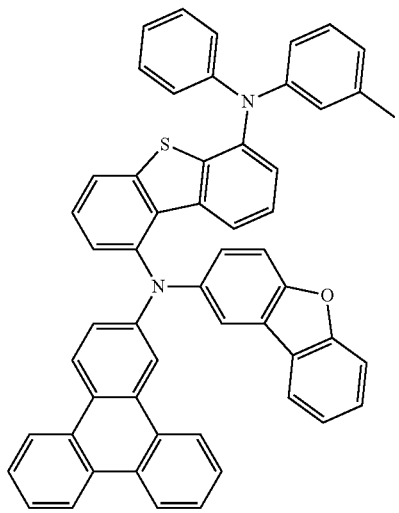
P-17
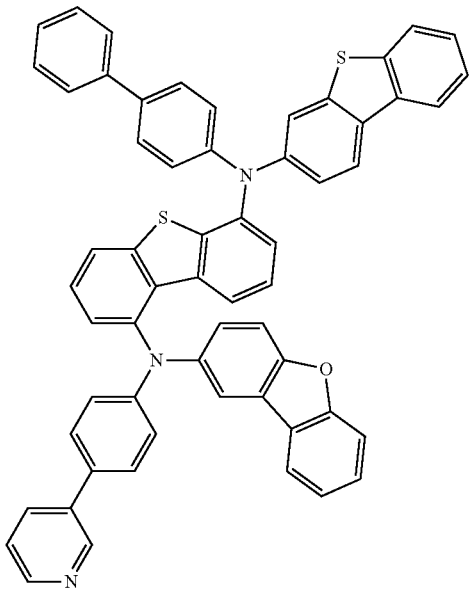
P-18
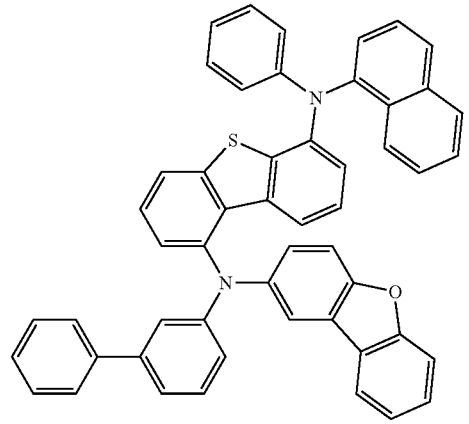
P-19
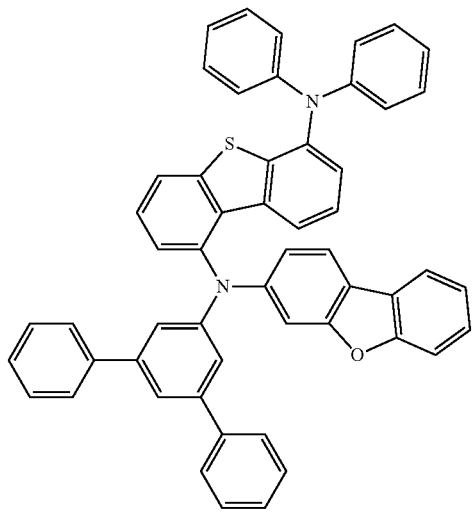
P-20
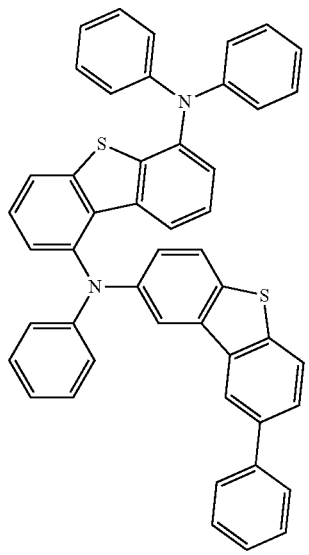
P-21
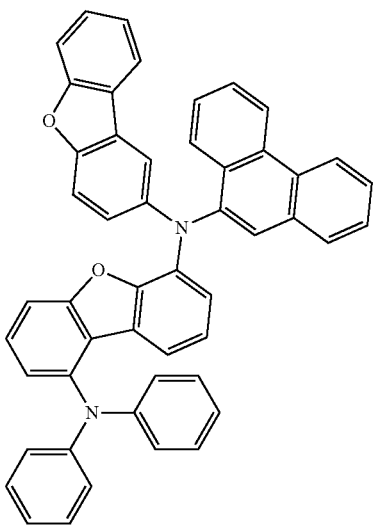

P-22
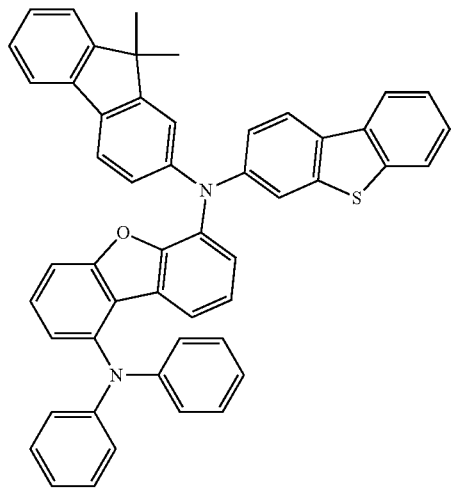
P-25
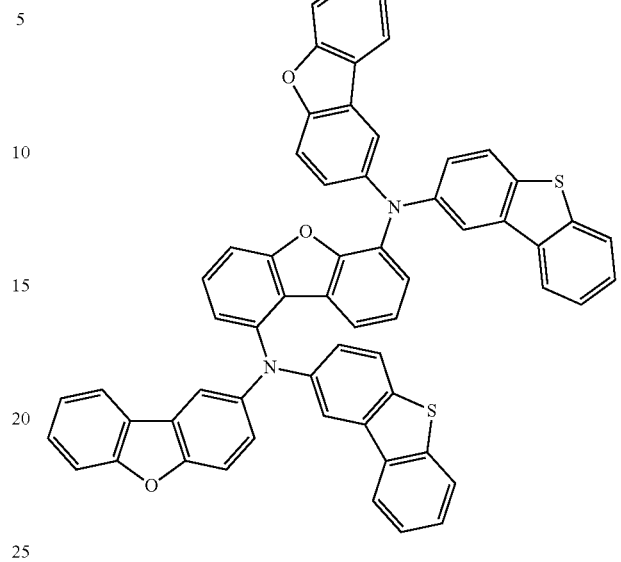
P-23
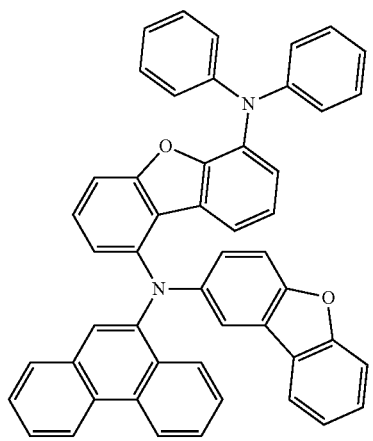
P-26
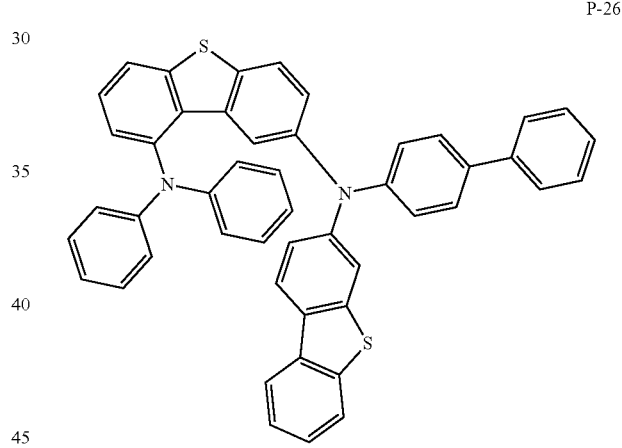
P-24
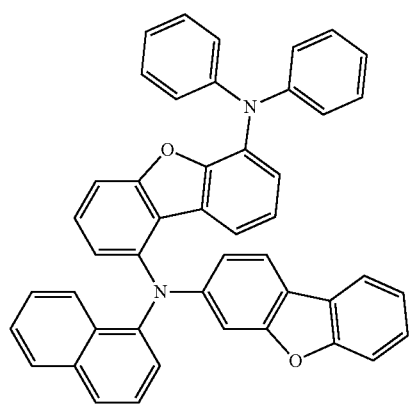
P-27
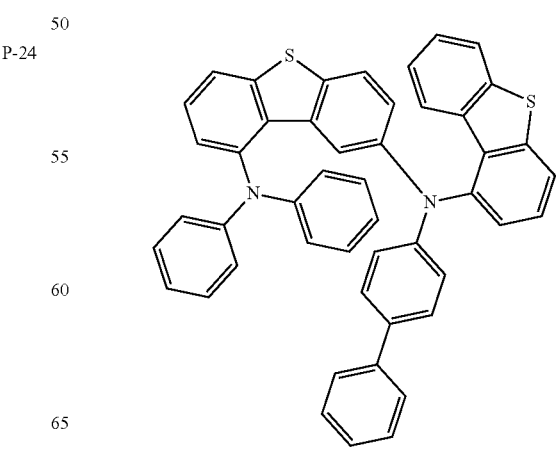

-continued
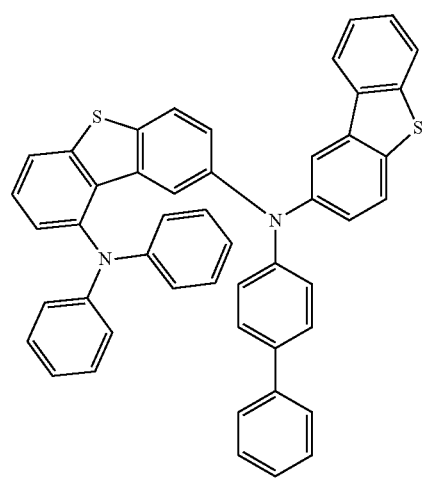
P-28
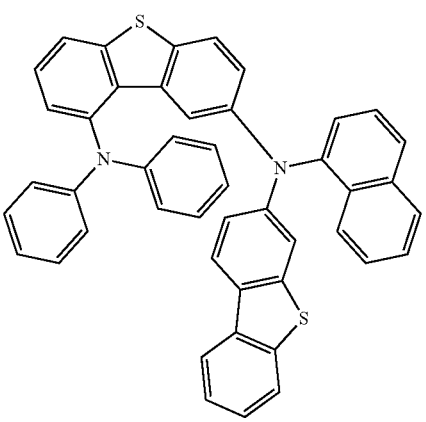
P-31
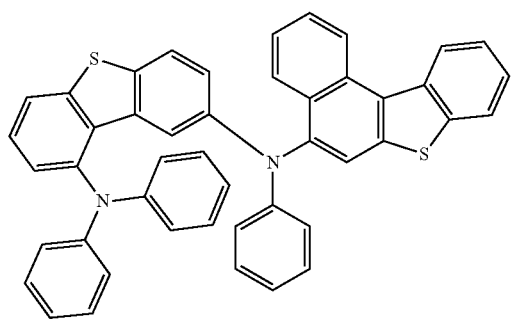
P-29
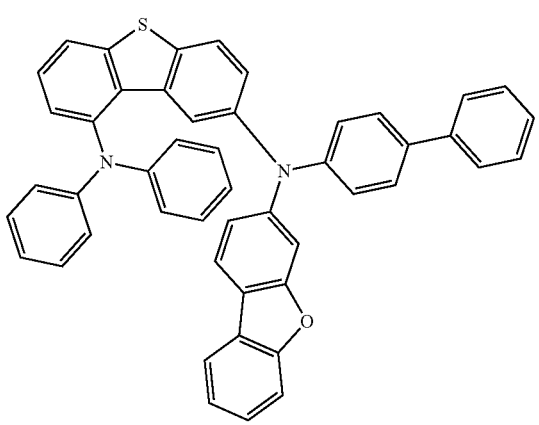
P-32
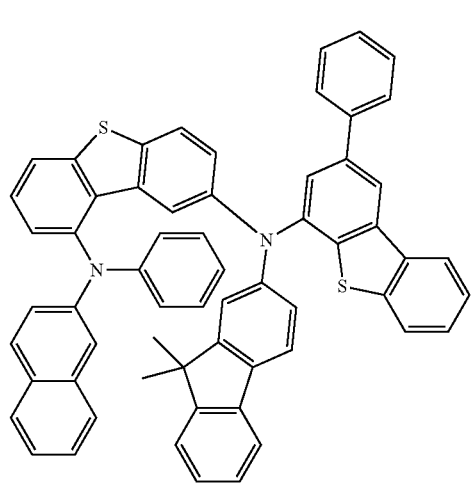
P-30
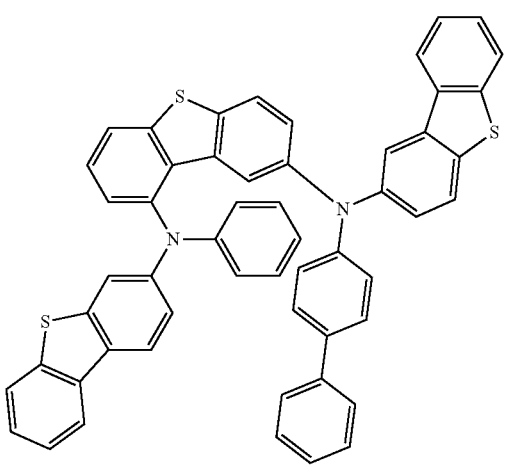
P-33

-continued
P-34
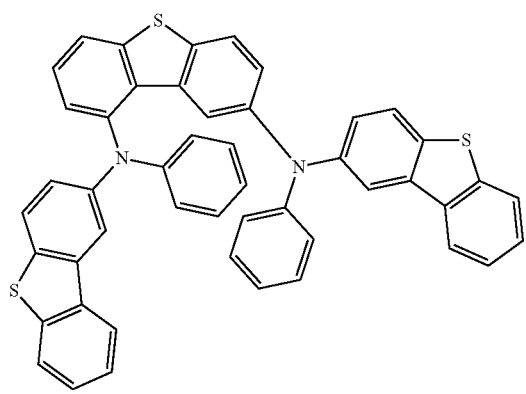
P-35
P-36
P-37
-continued
P-38
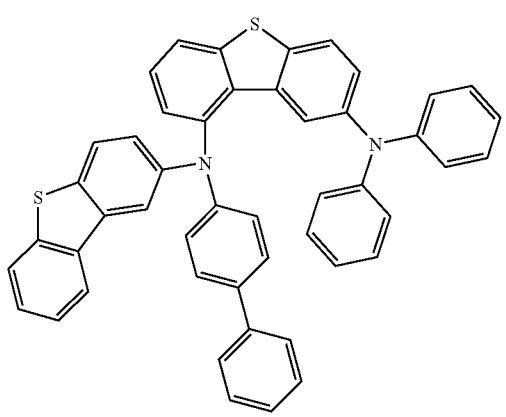
P-39
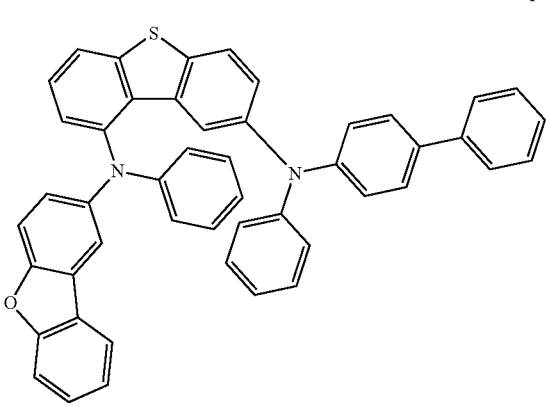
P-40
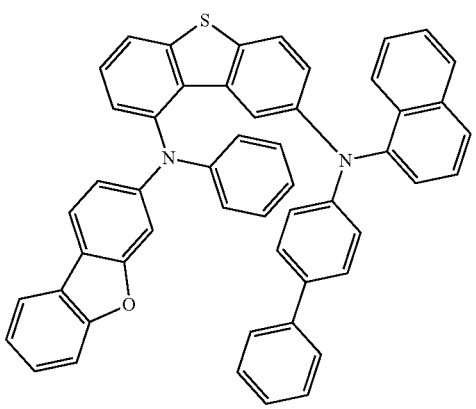
P-41
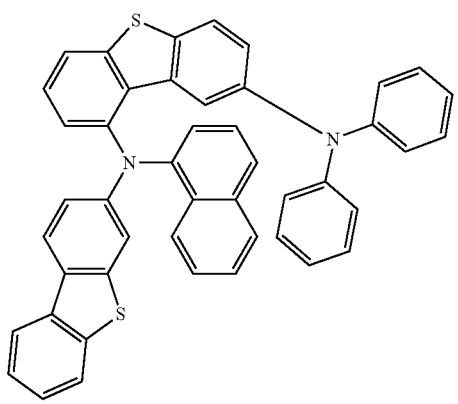

-continued
P-42
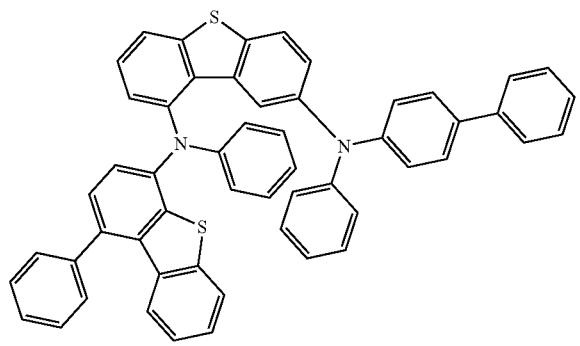
P-43
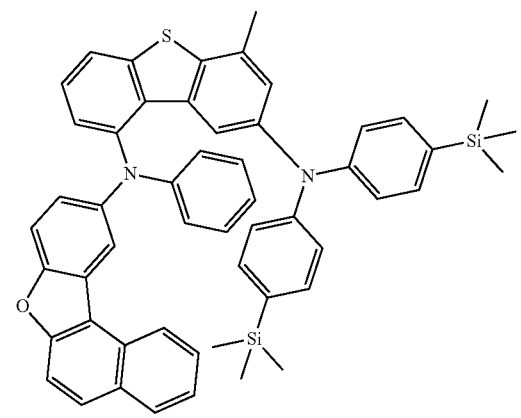
P-44
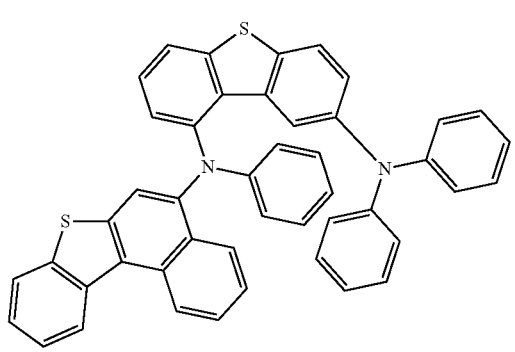
P-45
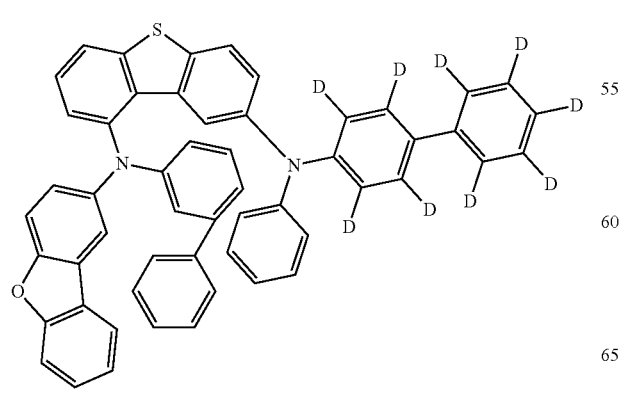
-continued
P-46
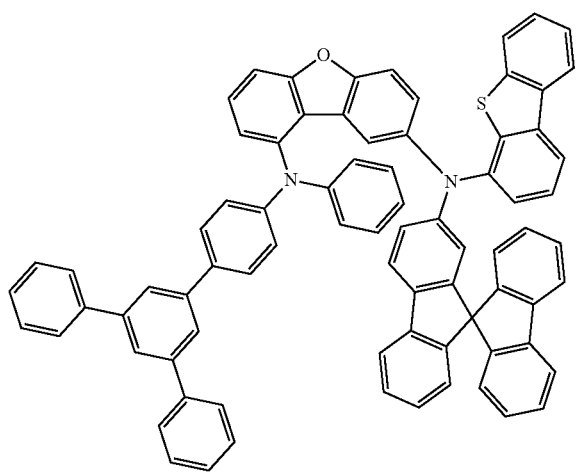
P-47
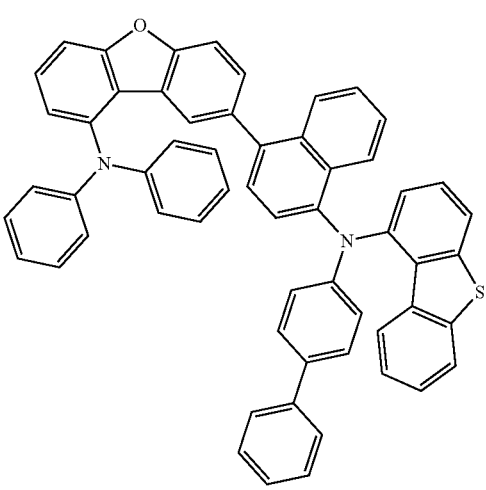
P-48
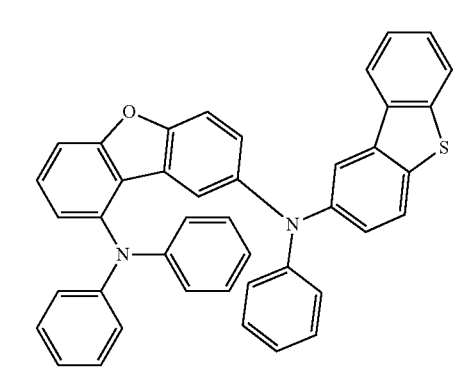

P-49
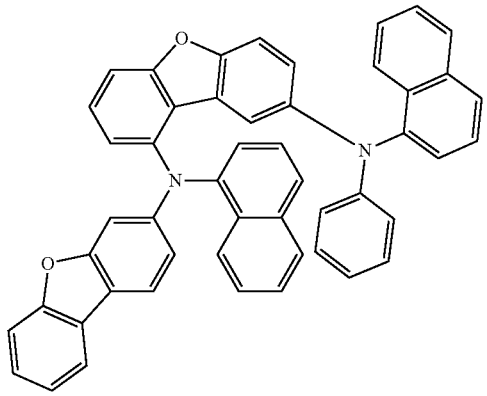
P-50
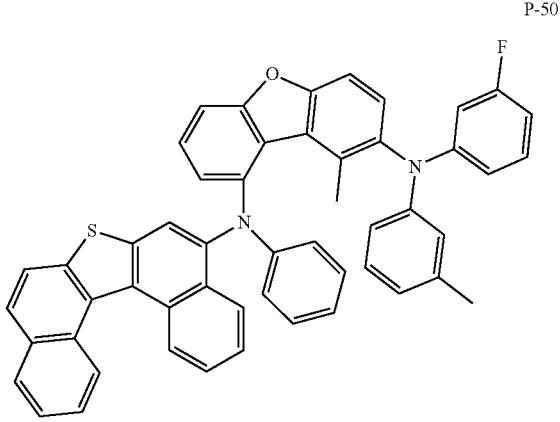
P-51
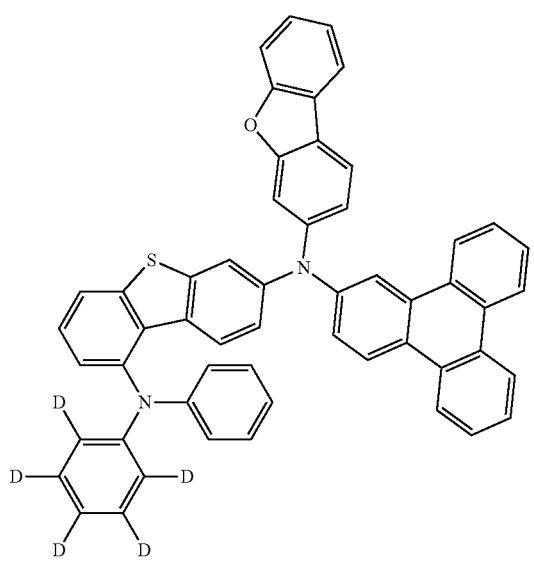
P-52
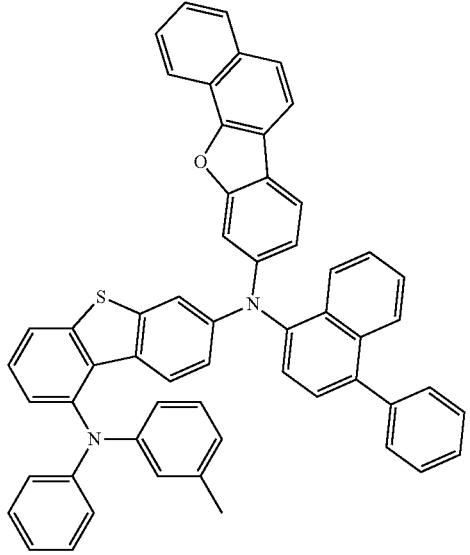
P-53
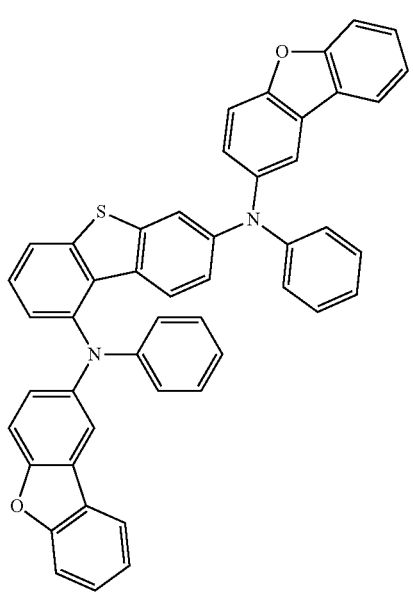
P-54
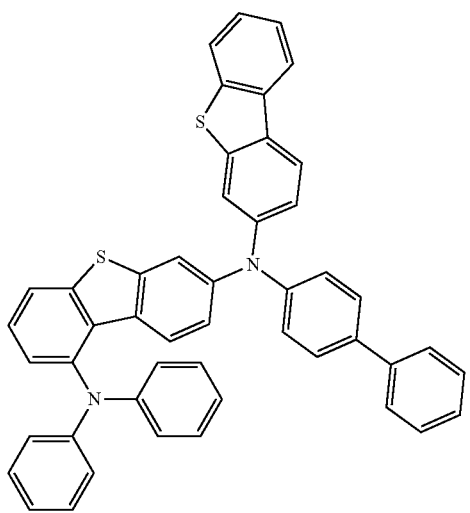

P-55
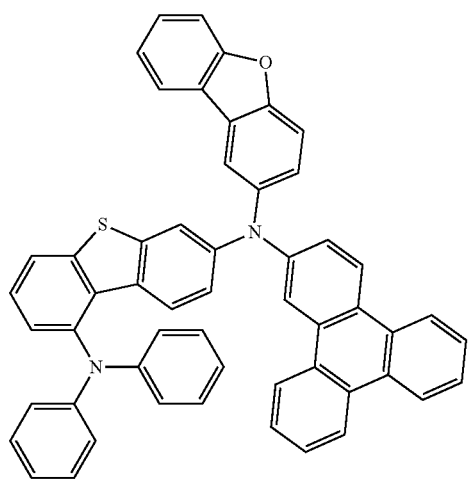
P-56
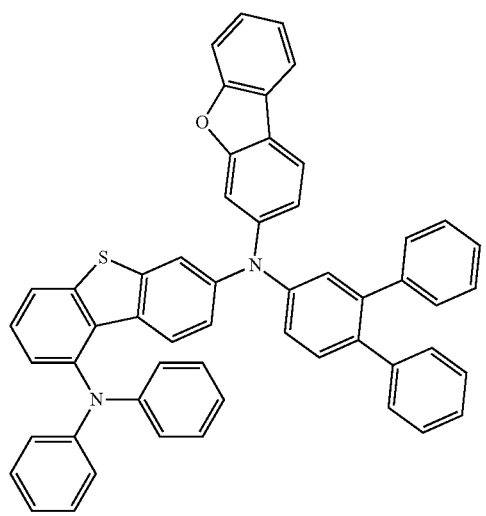
P-57
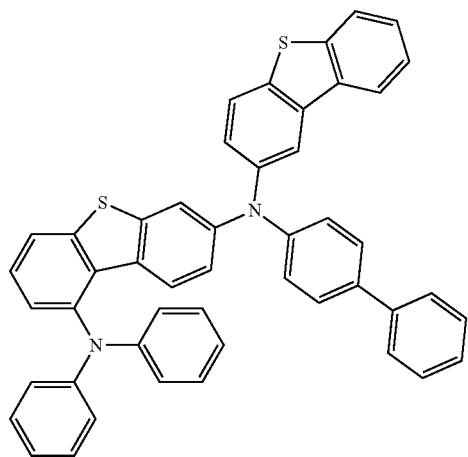
P-58
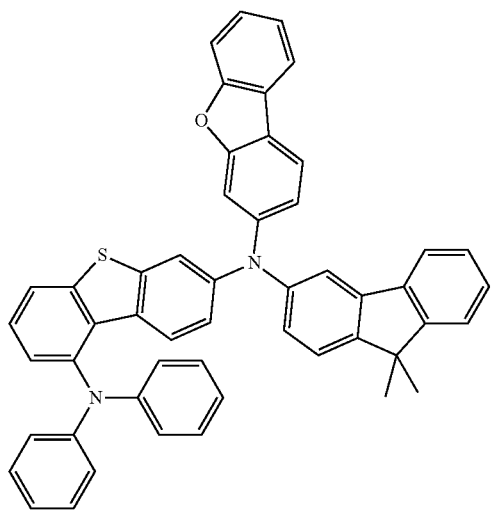
P-59
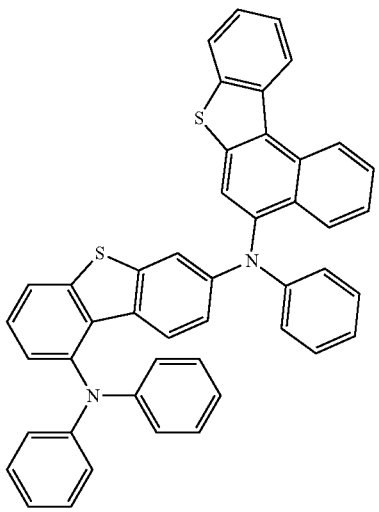
P-60
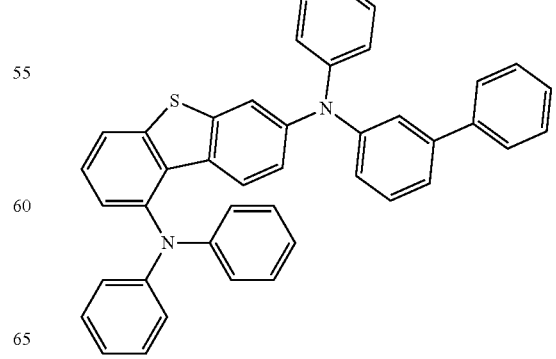

P-61
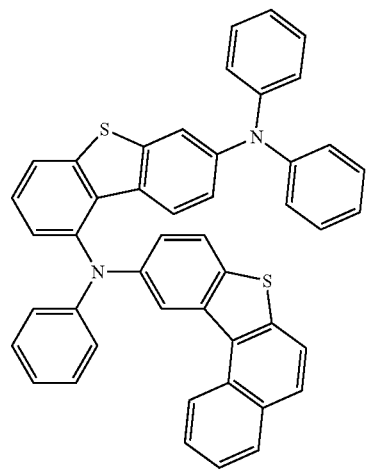
P-62
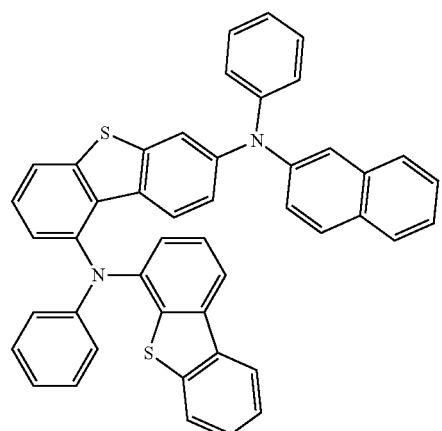
P-63
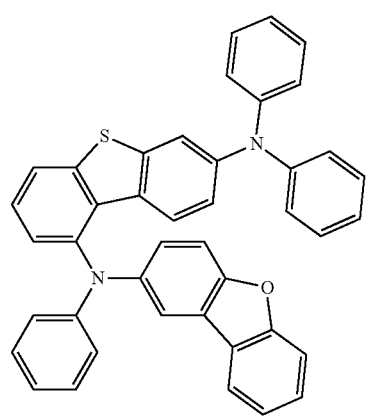
P-64
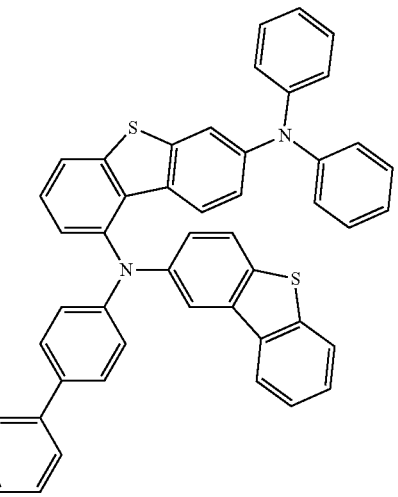
P-65
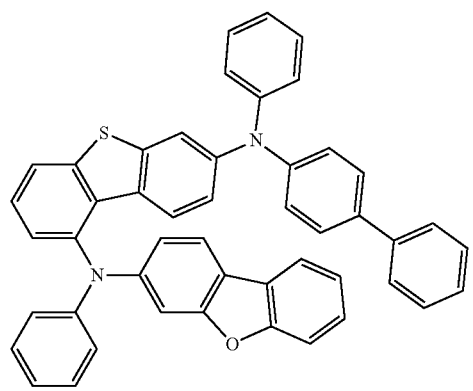
P-66
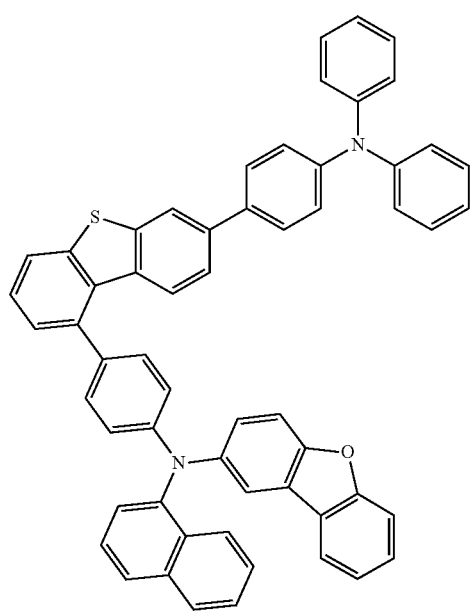

-continued
P-67
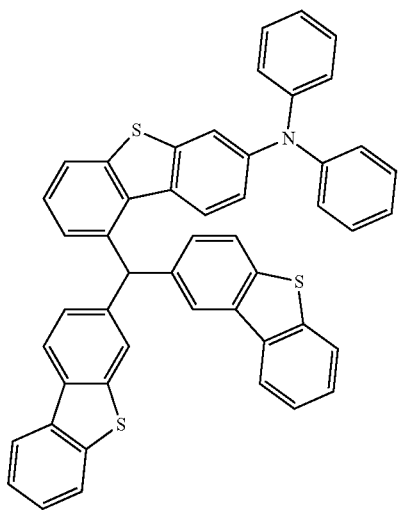
P-68
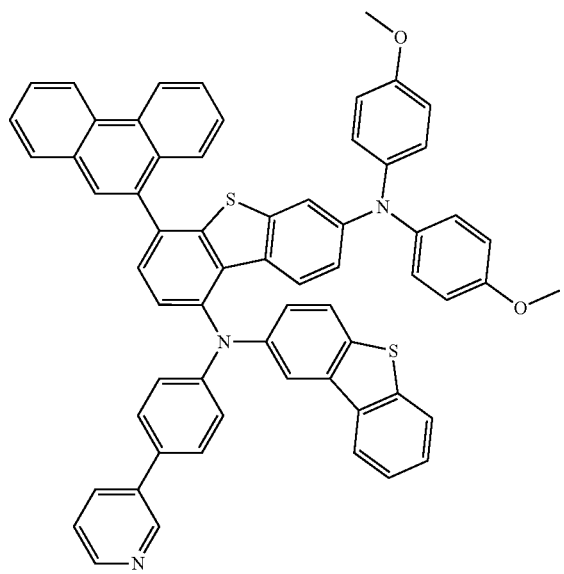
P-69
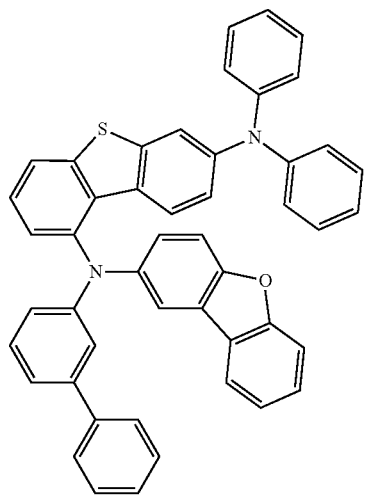
P-70
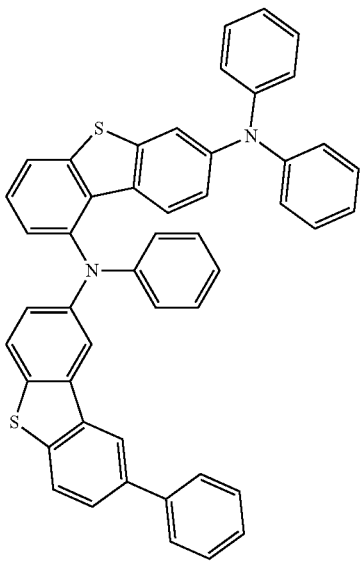
P-71
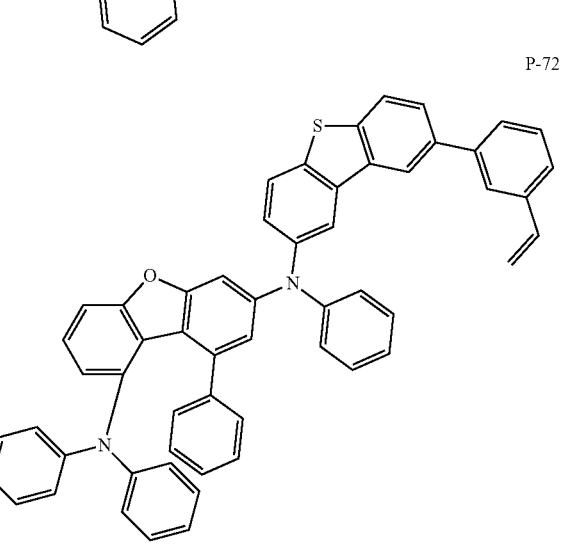
P-72

P-73
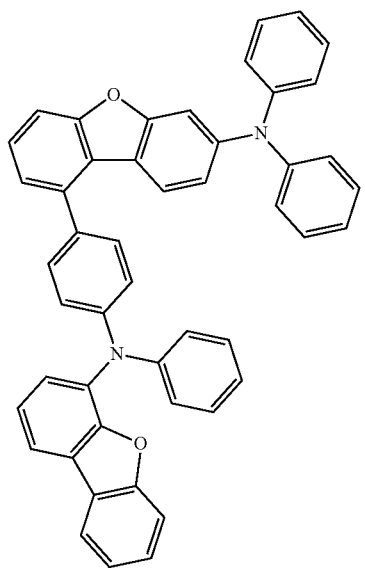
P-74
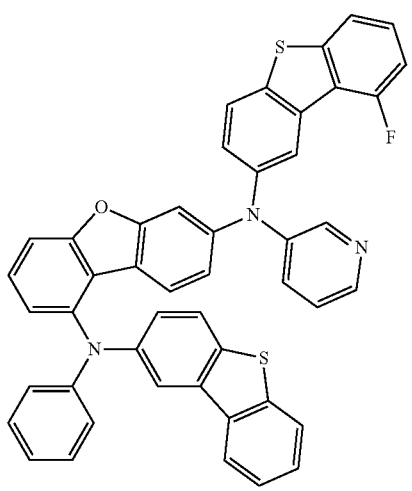
P-75
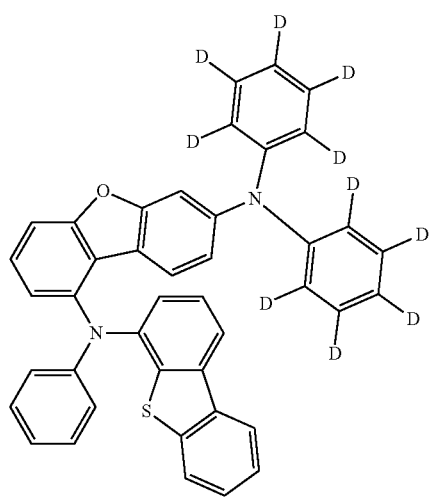
P-76
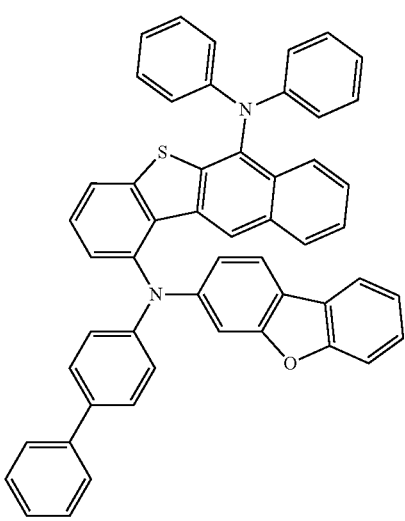
P-77
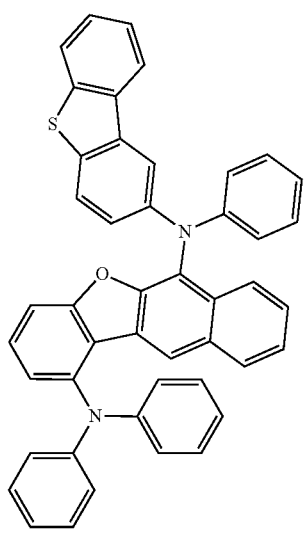
P-78
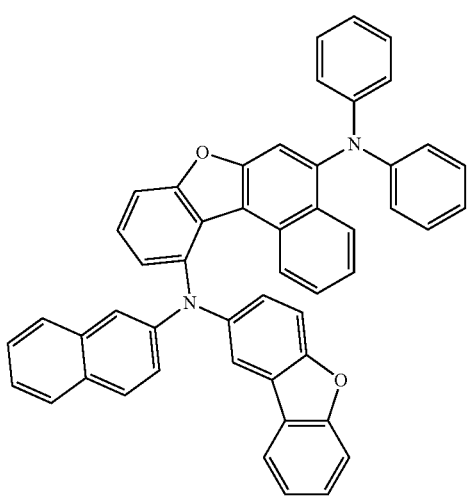

P-79
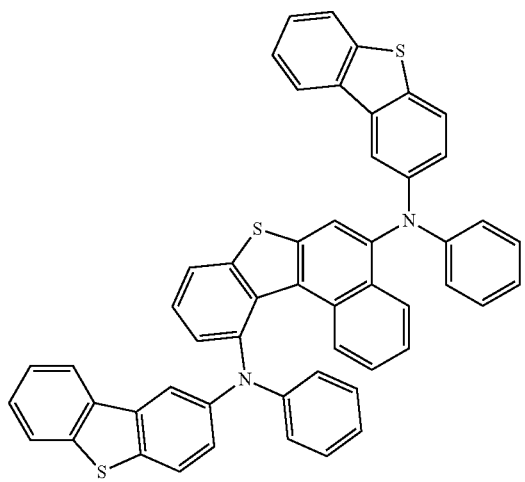
P-80
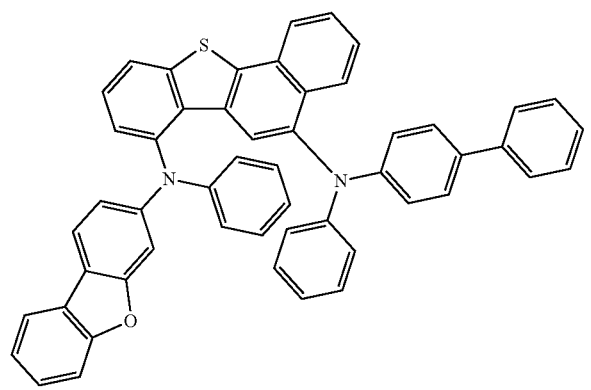
P-81
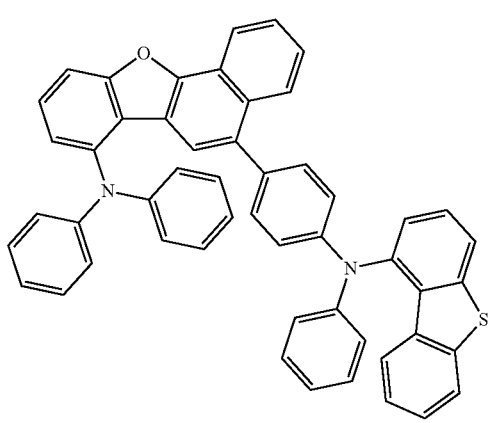
P-82
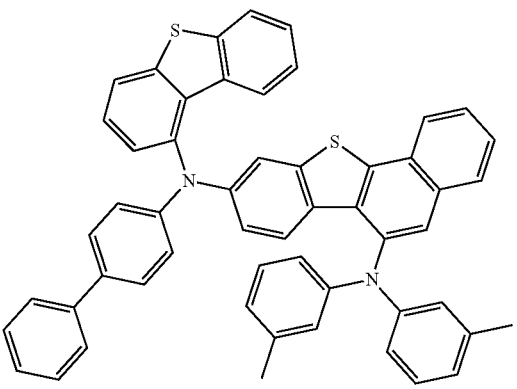
P-83
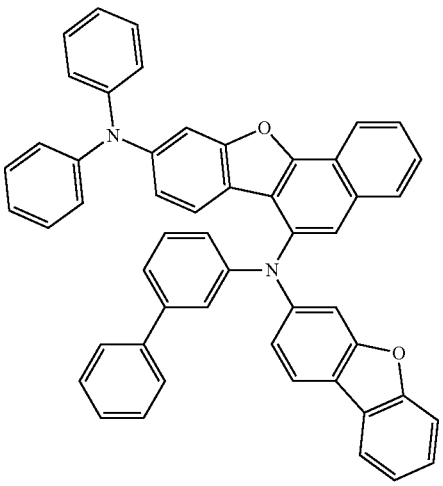
P-84
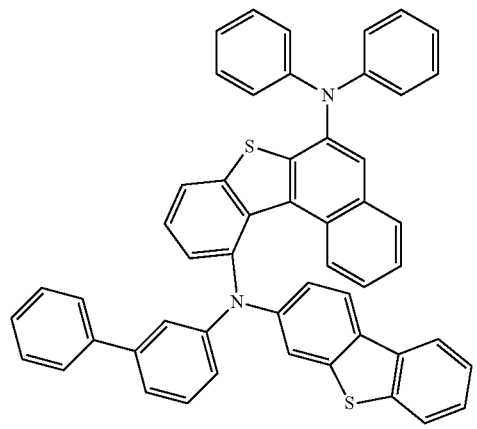

P-85

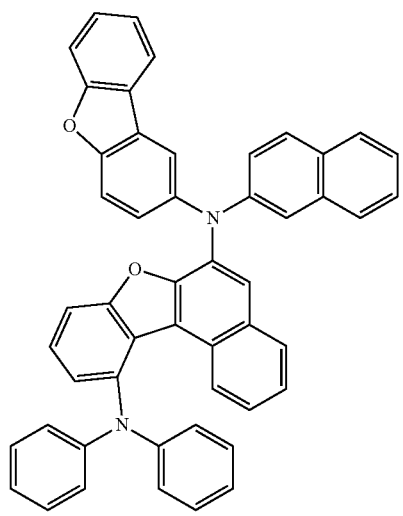

P-86

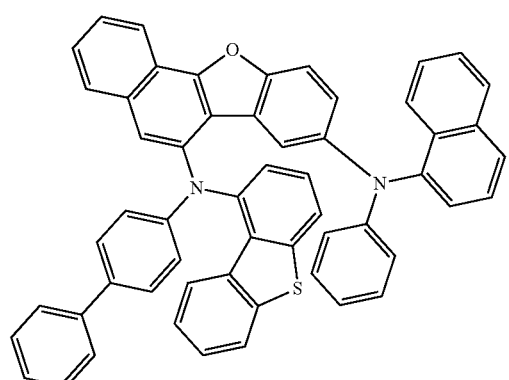

P-87

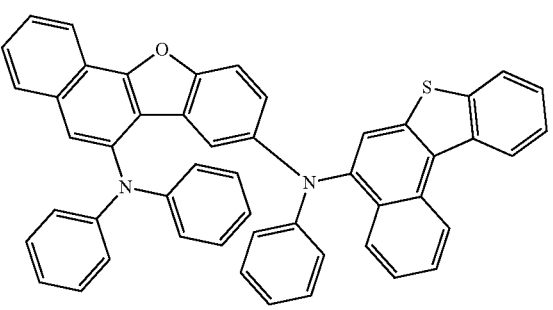

P-88

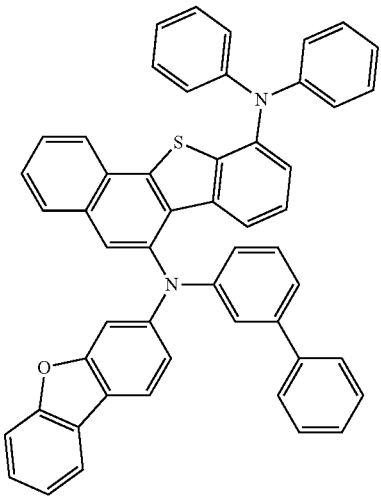

P-89 P-90

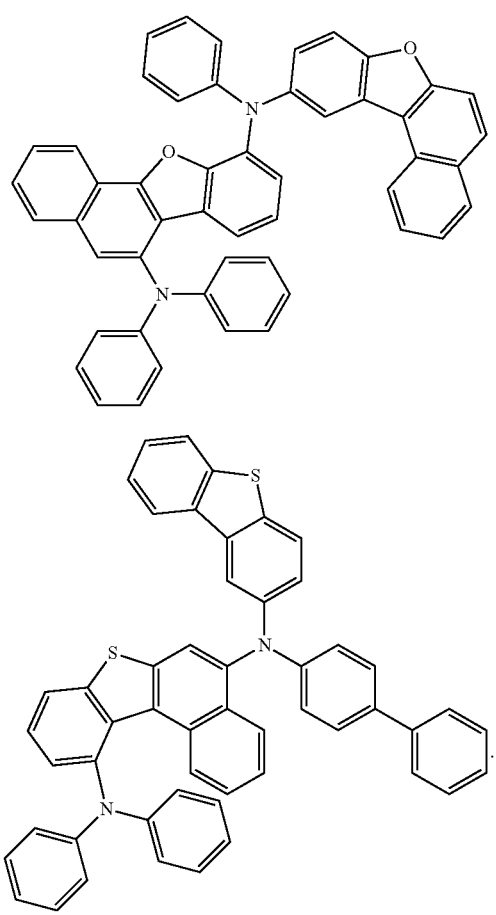

4. The organic electric element according to claim 1, further comprising a light efficiency enhancing layer formed on one side of the first electrode that is opposite to the side where the organic material layer is located and/or on one side of the second electrode that is opposite to the side where the organic material layer is located.

5. A display device comprising the organic electric element of claim 1; and a control part for driving the display device.

6. A display device according to claim 5, wherein the organic electronic element is an OLED, an organic solar cell, an organic photo conductor (OPC), organic transistor (organic TFT), or an element for monochromic or white illumination.

* * * * *